United States Patent
Prat Quinones et al.

(10) Patent No.: US 7,435,742 B2
(45) Date of Patent: Oct. 14, 2008

(54) QUINUCLIDINE DERIVATIVES AND PHARMACEUTICAL COMPOSITIONS CONTAINING THE SAME

(75) Inventors: Maria Prat Quinones, Barcelona (ES); Maria Antonia Buil Albero, Barcelona (ES); Maria Dolors Fernandez Forner, Barcelona (ES)

(73) Assignee: Laboratorios Almirall S.A., Barcelona (ES)

( * ) Notice: Subject to any disclaimer, the term of this patent is extended or adjusted under 35 U.S.C. 154(b) by 296 days.

(21) Appl. No.: 10/518,496

(22) PCT Filed: Jun. 18, 2003

(86) PCT No.: PCT/EP03/06472

§ 371 (c)(1),
(2), (4) Date: Sep. 19, 2005

(87) PCT Pub. No.: WO04/000840

PCT Pub. Date: Dec. 31, 2003

(65) Prior Publication Data

US 2006/0094751 A1     May 4, 2006

(30) Foreign Application Priority Data

Jun. 21, 2002   (ES)   ................... 200201439

(51) Int. Cl.
C07D 453/02 (2006.01)
C07D 221/02 (2006.01)
A61K 31/44 (2006.01)
A01N 43/90 (2006.01)

(52) U.S. Cl. .................. 514/299; 514/305; 546/137; 546/183

(58) Field of Classification Search .................. 546/183, 546/137; 514/299, 305
See application file for complete search history.

(56) References Cited

U.S. PATENT DOCUMENTS

| | | | |
|---|---|---|---|
| 2,762,796 A | 9/1956 | Morel et al. | |
| 3,714,357 A | 1/1973 | Gueremy et al. | |
| 6,916,828 B2 | 7/2005 | Farrerons Gallemi et al. | |
| 7,208,501 B2 * | 4/2007 | Buil Albero et al. | 514/305 |
| 7,312,231 B2 | 12/2007 | Buil Albero et al. | |
| 2004/0063950 A1 | 4/2004 | Farrerons Gallemi et al. | |
| 2004/0235887 A1 | 11/2004 | Farrerons Gallemi et al. | |
| 2004/0242629 A1 | 12/2004 | Buil Albero et al. | |
| 2004/0266816 A1 | 12/2004 | Buil Albero et al. | |
| 2005/0043349 A1 | 2/2005 | Catena Ruiz et al. | |
| 2008/0021060 A1 | 1/2008 | Buil Albero et al. | |

FOREIGN PATENT DOCUMENTS

| | | |
|---|---|---|
| CA | 2155320 | 8/1993 |
| EP | 0 424 021 A1 | 4/1991 |
| EP | 0 747 355 A1 | 12/1996 |
| EP | 0 801 067 A1 | 10/1997 |
| EP | 0 863 141 A1 | 9/1998 |
| EP | 0 930 298 A1 | 7/1999 |
| FR | 2 012 964 | 3/1970 |
| GB | 1 246 606 | 7/2005 |
| JP | 09-328469 | 12/1997 |
| WO | WO 93/15080 | 8/1993 |
| WO | WO01/04118 A2 | 1/2001 |
| WO | WO 01/04118 A3 | 1/2001 |
| WO | WO02/00652 A1 | 1/2002 |
| WO | 02/00652 * | 3/2002 |
| WO | 02/051841 * | 7/2002 |
| WO | WO02/051841 A1 | 7/2002 |
| WO | WO02/053564 A2 | 7/2002 |
| WO | 03/053966 * | 7/2003 |
| WO | WO 03/053966 A2 | 7/2003 |
| WO | WO 2004/000840 | 12/2003 |
| WO | WO 2004/005285 | 1/2004 |

OTHER PUBLICATIONS

Profita et al., Allergy, 2005, vol. 60, pp. 1361-1369.*
N.N. Godovikov, et al., "Synthesis and muscarinolytic activity of quinuclidinyl benzilate alkyl iodides", *Khim. Farm. Zh.*, vol. 19, No. 9, pp. 1060-1061, 1985.
J. Lars et al., "Some quinuclidine derivatives with potential antimalarial activity", *Acta Pharm. Suecica*, vol. 5, pp. 71-76, 1968.
L. Noronha-Blob et al., "Stereoselective antimuscarinic effects of 3-quinuclidinyl atrolactate and 3-quinuclidinyl xanthene-9-carboxylate", *European Journal of Pharmacology*, vol. 221, pp. 97-103, 1992.
S.H. Gao et al., "Stereochemistry of the Heterocyclic Alcohols Containing Piperidine Unit", *Chemical Journal of Chinese Universities*, vol. 20, No. 2, pp. 232-236, 1999.
PCT International Search Report dated Dec. 5, 2003.

(Continued)

*Primary Examiner*—D. Margaret Seaman
*Assistant Examiner*—Niloofar Rahmani
(74) *Attorney, Agent, or Firm*—Finnegan, Henderson, Farabow, Garrett & Dunner, LLP

(57) ABSTRACT

Carbamates of formula (I) or pharmaceutically acceptable salts thereof, including quaternary ammonium salts of formula (II) are disclosed; as well as processes for their preparation, pharmaceutical compositions comprising them and their use in therapy as antagonists of M3 muscarinic receptors.

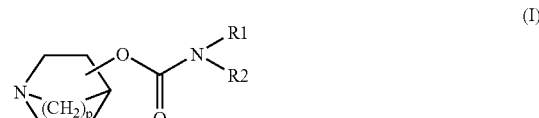

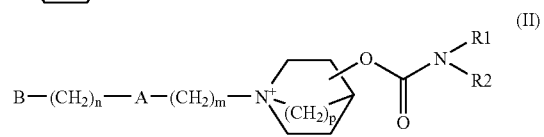

27 Claims, No Drawings

OTHER PUBLICATIONS

Abstract for Wallis, R.M. & Napier, C.M. Life Sci. 64(6-7):395-401 (1996) PMID 10069502.
Abstract for White, M.V. J. Allergy Clin. Immunol. 95(5 pt 2): 1065-68 (1995) PMID 7751523.
Brown, J.H. and Taylor, P. (2001) "Muscarinic Receptor Agonists and Antagonists," Chapter 7 in The Pharmacological Basis of Therapies. Goodmen et al. eds., McGraw Hill: 10th edition, pp. 155-173.
Eglen, R.M. and Hedge, S.S. (1997) "Muscarinic Receptor Subtypes: Pharmacology and Therapeutic Potential," Drug News Perspect. 10(8): 462-469.
Eglen, R.M. et al. "Therapeutic opportunities from muscarinic receptor research," Trends in Pharm. Sci. 22(8), Aug. 2001, 409-414.
Fryer et al., Am. J. Respir. Crit. Care Med. 158:S154-S160 (1998).
Interview Summary dated Jan. 19, 2006, from U.S. Appl. No. 10/404,395.
Interview Summary/Office Action dated Feb. 28, 2005, from U.S. Appl. No. 10/404,395.
Interview Summary/Office Action dated Feb. 28, 2005, in U.S. Appl. No. 10/193,622.
Konzett, H. and Rossler, R. (1940). "Versuchsanordnung zu Untersuchungen an der Brochialmuskulatur," Arch. Exp. Path. Pharmacol. 195: 71-74.
Notice of Allowance/Notice of Allowability, dated Jan. 19, 2006, from U.S. Appl. No. 10/404,395.
Office Action dated Feb. 3, 2005, from U.S. Appl. No. 10/404,395.
Office Action dated Feb. 3, 2005, in U.S. Appl. No. 10/193,622.
Office Action dated May 18, 2005, from U.S. Appl. No. 10/404,395.
Office Action dated May 18, 2005, in U.S. Appl. No. 10/193,622.
Office Action dated Nov. 1, 2005, in U.S. Appl. No. 10/193,622.
Rang, H.P. et al. (1995). "Cholinergic Transmission," Chapter 6 in Pharmacology. Churchill Livingstone, New York, NY. 3rd Edition, pp. 117-147.
Ringdahl, R. et al. (1979). "Facile Preparation of the Enantiomers of 3-acetoxyquinuclidine and 3-quinuclidinol," Acta Pharm Suec. 16: 281-283.
Saraswati, M. et al. (1994). "Structure Activity Studies of N,N-Dialkyl and Cycloalkyl Carbamate Esters of Dimethylethanolamine and Choline with Nicotine and Muscarinic Cholinergic Properties," Drug Development Research 31: 142-146.
Shutske, G.M. (1990) "A Novel Synthesis of the Isoxazolo[5,4,3-kl]-acridine Ring System," J. Heterocyclic Chem. 27: 1617-1621.
van Zwieten et al. Cardiovascular drugs and therapy/sponsored by the International Society of Cardiovascular Pharmacotherapy, 1995, 9(1): 159-67.
Waelbroeck, M. et al. (1990). "Binding of Selective Antagonists to Four Muscarinic Receptors (M1 to M4) in Rat Forebrain," Molecular Pharmacology. 38:267-273.
Xu et al. Chemical & Pharmaceutical Bulletin, 1998, 46(2): 231-241.
Notice of Allowance/Notice of Allowability, dated May 25, 2006, from U.S. Appl. No. 10/193,622.
Office Action dated Jul. 13, 2006, from U.S. Appl. No. 10/404,395.
Interview Summary, dated Jun. 13, 2006, from U.S. Appl. No. 10/193,622.
Notice of Allowance/Notice of Allowability, dated Jul. 27, 2006, from U.S. Appl. No. 10/193,622.
Office Action dated Nov. 8, 2006, from U.S. Appl. No. 10/404,395.
Notice of Allowance/Notice of Allowability, dated Mar. 26, 2007, from U.S. Appl. No. 10/404,395.

* cited by examiner

QUINUCLIDINE DERIVATIVES AND PHARMACEUTICAL COMPOSITIONS CONTAINING THE SAME

This application is a national stage filing under 35 U.S.C. § 371 of International Application No. PCT/EP2003/006472, filed on Jun. 18, 2003. This application claims the benefit of priority under 35 U.S.C. § 119 to Spanish Patent Application No. P200201439 filed on Jun. 21, 2002.

This invention relates to new therapeutically useful quinuclidine carbamate derivatives, to some processes for their preparation and to pharmaceutical compositions containing them.

The structures according to the invention are antimuscarinic agents with a potent and long lasting effect. In particular, these compounds show high affinity and selectivity for muscarinic M3 receptors over M2 receptors. The M3 subtype of muscarinic receptor is present in glands and smooth muscle and mediates the excitatory effects of the parasympathetic system on glandular secretion and on the contraction of visceral smooth muscle (Chapter 6, *Cholinergic Transmission*, in H. P. Rang et al., *Pharmacology*, Churchill Livingstone, New York, 1995).

M3 antagonists are therefore known to be useful for treating diseases characterised by an increased parasympathetic tone, by excessive glandular secretion or by smooth muscle contraction (R. M. Eglen and S. S. Hegde, (1997), Drug News Perspect., 10(8):462-469).

Examples of this kind of diseases are respiratory disorders such as chronic obstructive pulmonary disease (COPD), bronchitis, bronchial hyperreactivity, asthma, cough and rhinitis; urological disorders such as urinary incontinence, pollakiuria, neurogenic or unstable bladder, cystospasm and chronic cystitis; gastrointestinal disorders such as irritable bowel syndrome, spastic colitis, diverticulitis and peptic ulceration; and cardiovascular disorders such as vagally induced sinus bradycardia (Chapter 7, *Muscarinic Receptor Agonists and Antagonists, in Goodman and Gilman's The Pharmacological Basis of Therapeutics*, 10the edition, McGraw Hill, Ney York, 2001).

The compounds of the invention can be used alone or in association with other drugs commonly regarded as effective in the treatment of these diseases. For example, they can be administered in combination with $\beta_2$-agonists, steroids, anti-allergic drugs, phosphodiesterase IV inhibitors and/or leukotriene D4 (LTD4) antagonists for simultaneous, separate or sequential use in the treatment of a respiratory disease.

The present invention provides new quinuclidine carbamate derivatives with potent antagonist activity at muscarinic M3 receptors, which fall under the chemical structure described in formula (I) or are pharmaceutically acceptable salts thereof, including quaternary salts of formula (II).

Formula (I) represents a carbamate of the following general structure:

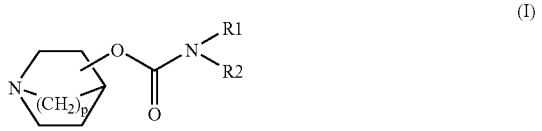

(I)

wherein
R1 represents a group selected from phenyl, 2-furyl, 3-furyl, 2-thienyl, 3-thienyl, benzyl, furan-2-ylmethyl, furan-3-ylmethyl, thiophen-2-ylmethyl, and thiophen-3-ylmethyl;

R2 represents a group selected from optionally substituted lower alkyl, optionally substituted lower alkenyl, optionally substituted lower alkynyl, saturated or unsaturated cycloalkyl, saturated or unsaturated cycloalkylmethyl, phenyl, benzyl, phenethyl, furan-2-ylmethyl, furan-3-ylmethyl, thiophen-2-ylmethyl, thiophen-3-ylmethyl, pyridyl, and pyridylmethyl; wherein the carbocyclic moieties in the cycloalkyl, cycloalkylmethyl, phenyl, benzyl or phenethyl groups can be optionally bridged or fused to another saturated, unsaturated or aromatic carbocyclic moiety or to a cyclic moiety comprising carbon atoms and 1 or 2 oxygen atoms;

the cyclic groups present in R1 and R2 being optionally substituted by one, two or three substituents selected from halogen, straight or branched, optionally substituted lower alkyl, hydroxy, straight or branched, optionally substituted lower alkoxy, —SH, straight or branched optionally substituted lower alkylthio, nitro, cyano, —NR'R", —CO$_2$R', —C(O)—NR'R", —N(R''')C(O)—R', —N(R''')—C(O)NR'R", wherein R', R" and R''' each independently represents a hydrogen atom or a straight or branched, optionally substituted lower alkyl group or R' and R" together with the atom to which they are attached form a cyclic group;

p is 1 or 2 and the carbamate group is attached at positions 2, 3 or 4 of the azabicyclic ring, and pharmaceutically acceptable salts thereof, including quaternary ammonium salts of formula (II)

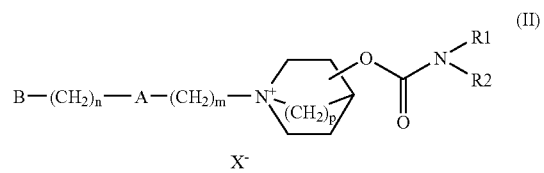

(II)

wherein R1, R2 and p are as defined above;
m is an integer from 0 to 8;
n is an integer from 0 to 4;
A represents a group selected from —CH$_2$—, —CH=CR'—, —CR=CH—, —CR'R"—, —C(O)—, —O—, —S—, —S(O)—, —S(O)$_2$— and —NR'—, wherein R' and R" are as defined above;
B represents a hydrogen atom, or a group selected from straight or branched, optionally substituted lower alkyl, hydroxy, straight or branched, optionally substituted lower alkoxy, cyano, nitro, —CH=CR'R", —C(O)OR', —OC(O)R', —SC(O)R', —P(O)NR'R", —NR'C(O)OR", —NR'C(O)NR", cycloalkyl, phenyl, naphthanelyl, 5,6,7,8-tetrahydronaphthanelyl, benzo[1,3]dioxolyl, heteroaryl or heterocyclyl; R' and R" being as defined above; and wherein the cyclic groups represented by B are optionally substituted by one, two or three substitutuents selected from halogen, hydroxy, straight or branched, optionally substituted lower alkyl, phenyl, —OR', —SR', —NR'R", —NHCOR', —CONR'R", —CN, —NO$_2$ and —COOR'; R' and R" being as defined above;
X$^-$ represents a pharmaceutically acceptable anion of a mono or polyvalent acid;
including all individual stereoisomers of formulae (I) or (II) and mixtures thereof;
with the proviso that the compound of formula (I) is not one of
Diphenylcarbamic acid 1-azabicyclo[2.2.2]oct-3-yl ester
Ethylphenylcarbamic acid 1-azabicyclo[2.2.2]oct-3-yl ester Further objectives of the present invention are to provide processes for preparing said compounds; pharmaceutical compositions comprising an effective amount of said compounds; the use of the compounds in the manufacture of a medicament for the treatment of diseases susceptible of being improved by antagonism of M3 muscarinic receptors; and methods of treatment of diseases susceptible to amelioration by antagonism of M3 muscarinic receptors, which methods comprise the administration of the compounds of the invention to a subject in need of treatment.

In the compounds of the invention it is preferred that at least one of R1 or R2 be substituted. Particularly preferred compounds of formula (I) or (II) are those wherein when the cyclic group present in R1 is unsubstituted or has only one substitutent R2 has at least one substituent. Also preferred are compounds wherein when R2 is not substituted the cyclic group present in R1 has at least two substituents.

J. L. G. Nilsson et al. describe in Acta Pharm. Suecica, 5:71-76 (1968) a group of quinuclidine carbamate derivatives having antimalarial activity, among which diphenylcarbamic acid 1-azabicyclo[2.2.2]oct-3-yl ester and ethylphenylcarbamic acid 1-azabicyclo[2.2.2]oct-3-yl ester are mentioned.

WO 02/00652 discloses a group of compounds which fall under the general structure of formula (I) or (II). The specific compounds disclosed in that application are excluded from the present invention.

Thus, in those compounds of formula (I) as described above, wherein p is 2;

the carbamate group is attached at position 3 of the azabicyclic ring;

and R1 is an unsubstituted indanyl group or a phenyl group, which is optionally substituted with one or two substitutents selected from chlorine, fluorine, bromine, methyl, hydroxy and cyano;

then R2 cannot be one of: unsubstituted cyclopropylmethyl; unsubstituted cyclobutylmethyl; unsubstituted cyclopentylmethyl; cyclohexylmethyl optionally substituted with a methyl or an isopropenyl group; unsubstituted cyclohexenyl; unsubstituted norbornenyl; unsubstituted bicyclo[2,2,1]heptanyl; unsubstituted benzo[1,3]dioxolyl; unsubstituted 2,3-dihydrobenzo[1,4]dioxinyl; unsubstituted benzyl; a benzyl group which is substituted with one or two substituents selected from fluorine, chlorine, bromine, methoxy, methyl, trifluoromethyl, ethyl, tertbutyl, hydroxy, hydroxymethyl, cyano, aminocarbonyl, trifluoromethoxy, benzyloxy, isopropyloxy; and a benzyl group which is substituted with three fluorine atoms.

Further, in those compounds of formula (II) as described above wherein p is 2;

the carbamate group is attached at position 3 of the azoniabicyclic ring having (3R)-configuration;

R1 is a phenyl group which is optionally substituted with a fluorine atom or a methyl group;

R2 is an unsubstituted cyclohexylmethyl group or a benzyl group which is optionally substituted with one or three fluorine atoms;

and X- iodine;

then, the sequence B—$(CH_2)_n$-A-$(CH_2)_m$— cannot be a methyl group.

More specifically, the following compounds are explicitly excluded from the scope of the invention:

(3R)-3-(Benzylphenylcarbamoyloxy)-1-methyl-1-azoniabicyclo[2.2.2]octane iodide (3R)-3-[(4-Fluorobenzyl)phenylcarbamoyloxy]-1-methyl-1-azoniabicyclo[2.2.2]octane iodide (3R)-3-(Benzyl-o-tolylcarbamoyloxy)-1-methyl-1-azoniabicyclo[2.2.2]octane iodide (3R)-1-Methyl-3-[o-tolyl-(2,4,5-trifluorobenzyl)carbamoyloxy]1-azoniabicyclo[2.2.2]octane iodide (3R)-3-[(4-Fluorobenzyl)-m-tolylcarbamoyloxy]-1-methyl-1-azoniabicyclo[2.2.2]octane iodide (3R)-3-[Benzyl-(2-fluorophenyl)carbamoyloxy]-1-methyl-1-azoniabicyclo[2.2.2]octane iodide (3R)-3[-Cyclohexylmethyl-(2-fluorophenyl)carbamoyloxy]-1-methyl-1-azoniabicyclo[2.2.2]octane iodide As used herein, an alkyl, alkenyl or alkynyl group or moiety can be straight or branched, and is typically a lower alkyl, alkenyl or alkynyl group. A lower alkyl group contains 1 to 8, preferably 1 to 6, carbon atoms. Examples include methyl, ethyl, propyl, including i-propyl, butyl, including n-butyl, sec-butyl and tert-butyl, 1-methylbutyl, 1-ethylpropyl, 1,2-dimethylpropyl, n-hexyl or 1-ethylbutyl groups. More preferably a lower alkyl group contains from 1 to 4 carbon atoms. A lower alkenyl or alkynyl group contains 2 to 8, preferably 2 to 6, carbon atoms. Examples include vinyl, allyl, 1-propenyl, 4-pentenyl, 1-propynyl, 2-propynyl, 1-butynyl, 2-butynyl or 3-butynyl groups. More preferably, a lower alkenyl or alkynyl group contains 2 to 4 carbon atoms.

Optionally substituted lower alkyl, alkenyl or alkynyl groups mentioned herein include straight or branched lower alkyl, alkenyl or alkynyl groups as defined above, which may be unsubstituted or substituted in any position by one or more substituents, for example by 1, 2 or 3 substituents. When two or more substituents are present, each substituent may be the same or different. The substituent(s) are typically halogen atoms, preferably fluoride atoms, and hydroxy or alkoxy groups.

Alkoxy and alkylthio groups mentioned herein are typically lower alkoxy and alkylthio groups, that is groups containing from 1 to 8, preferably 1 to 6 and more preferably 1 to 4 carbon atoms, the hydrocarbon chain being branched or straight and optionally substituted in any position by one or more substituents, for example by 1; 2 or 3 substituents. When two or more substituents are present, each substituent may be the same or different. The substituent(s) are typically halogen atoms, most preferably fluoride atoms, and hydroxy groups. Preferred optionally substituted alkoxy groups include methoxy, ethoxy, n-propoxy, i-propoxy, n-butoxy, sec-butoxy, t-butoxy, trifluoromethoxy, difluoromethoxy, hydroxymethoxy, 2-hydroxyethoxy or 2-hydroxypropoxy. Preferred optionally substituted alkylthio groups include methylthio, ethylthio, n-propylthio, i-propylthio, n-butylthio, sec-butylthio, t-butylthio, trifluoromethylthio, difluoromethylthio, hydroxymethylthio, 2-hydroxyethylthio or 2-hydroxypropylthio.

Cyclic groups mentioned herein include, unless otherwise specified, carbocyclic and heterocyclic groups. The cyclic groups can contain one or more rings. Carbocyclic groups may be aromatic or alicyclic, for example cycloalkyl groups. Heterocyclic groups also include heteroaryl groups.

Cycloalkyl groups and alicyclic groups mentioned herein, unless otherwise specified, typically contain from 3 to 7 carbon atoms. Cycloalkyl groups and alicyclic rings of 3 to 7 carbon atoms include cyclopropyl, cyclobutyl, cyclopentyl, cyclohexyl and cycloheptyl.

As used herein an aromatic group typically contains from 5 to 14, preferably 5 to 10 carbon atoms. Examples of aromatic groups include phenyl and naphthalenyl.

A heterocyclic or heteroaromatic group mentioned herein is typically a 5 to 10 membered group, such as a 5, 6 or 7 membered group, containing one or more heteroatoms selected from N, S and O. Typically, 1, 2, 3 or 4 heteroatoms are present, preferably 1 or 2 heteroatoms. A heterocyclic or heteroaromatic group may be a single ring or two or more fused rings wherein at least one ring contains a heteroatom. Examples of heterocyclic groups include piperidyl, pyrrolidyl, piperazinyl, morpholinyl, thiomorpholinyl, pyrrolyl, imidazolyl, imidazolidinyl, pyrazolinyl, indolinyl, isoindolinyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, quinuclidinyl, triazolyl, pyrazolyl, tetrazolyl and thienyl. Examples of heteroaromatic groups include pyridyl, thienyl, furyl, pyrrolyl, imidazolyl, benzothiazolyl, pyridinyl, pyrazolyl, pyrazinyl, pyrimidinyl, pyridazinyl, indolyl, indazolyl, purinyl, quinolyl, isoquinolyl, phthalazinyl, naphthyridinyl, quinoxalinyl, quinazolinyl, cinnolinyl, triazolyl and-pyrazolyl.

As used herein a halogen atom includes a fluorine, chlorine, bromine or iodine atom, typically a fluorine, chlorine or bromine atom.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, formic, mandelic, ascorbic, oxalic, succinic, tartaric, benzoic, acetic, methanesulphonic, ethanesulphonic, benzenesulphonic or p-toluenesulphonic acid.

In the quaternary ammonium compounds of the present invention, including those represented by formula (II), an equivalent of an anion ($X^-$) is associated with the positive charge of the N atom. $X^-$ may be an anion of various mineral acids such as, for example, chloride, bromide, iodide, sulphate, nitrate, phosphate, or an anion of an organic acid such as, for example, acetate, trifluoroacetate, maleate, fumarate, citrate, oxalate, succinate, tartrate, malate, mandelate, formate, methanesulfonate and p-toluenesulfonate. $X^-$ is preferably an anion selected from chloride, bromide, iodide, sulphate, nitrate, acetate, trifluoroacetate, formate, methanesulfonate, maleate, oxalate or succinate. More preferably $X^-$ is chloride, bromide, formate, trifluoroacetate or methanesulfonate.

Preferred compounds of formula (I) according to the invention as defined above are those wherein R1 represents a group selected from 2-furyl, 3-furyl, 2-thienyl, 3-thienyl, benzyl, furan-2-ylmethyl, furan-3-ylmethyl, thiophen-2-ylmethyl, thiophen-3-ylmethyl; the cyclic groups present in R1 being optionally substituted by one, two or three substituents selected from halogen, straight or branched, optionally substituted lower alkyl, hydroxy, straight or branched, optionally substituted lower alkoxy, —SH, straight or branched optionally substituted lower alkylthio, nitro, cyano, —NR'R", —CO$_2$R', —C(O)—NR'R", —N(R''')C(O)—R', —N(R''')—C(O)NR'R", wherein R', R" and R''' each independently represents a hydrogen atom or a straight or branched, optionally substituted lower alkyl group or R' and R" together with the atom to which they are attached form a cyclic group;

Also preferred are compounds of formula (I) as defined above wherein R2 represents an optionally substituted group selected from lower alkyl, lower alkenyl, lower alkynyl, saturated or unsaturated cycloalkyl, phenyl, phenethyl, furan-2-ylmethyl, furan-3-ylmethyl, thiophen-2-ylmethyl, thiophen-3-ylmethyl, pyridyl, and pyridylmethyl or a saturated or unsaturated cycloalkylmethyl group which has at least one substituent and is selected from substituted cyclopropylmethyl, substituted cyclobutylmethyl and substituted cyclopentylmethyl; the substituents of the cyclic groups present in R2 being one, two or three substituents selected from halogen, straight or branched, optionally substituted lower alkyl, hydroxy, straight or branched, optionally substituted lower alkoxy, —SH, straight or branched optionally substituted lower alkylthio, nitro, cyano, —NR'R", —CO$_2$R', —C(O)NR'R", —N(R''')C(O)—R', —N(R''')—C(O)NR'R", wherein R', R" and R''' each independently represents a hydrogen atom or a straight or branched, optionally substituted lower alkyl group or R' and R" together with the atom to which they are attached form a cyclic group;

Preferred compounds of formula (II) according to the invention as defined above are those wherein R1 represents a group selected from phenyl, 2-thienyl, 3-thienyl, thiophen-2-ylmethyl, thiophen-3-ylmethyl, furan-2-ylmethyl or furan-3-ylmethyl, the cyclic groups present in R1 being optionally substituted with one to three substitutents selected from fluorine, chlorine, bromine, methyl, methoxy, trifluoromethyl, ethyl, tert-butyl, hydroxy and cyano.

In particularly preferred embodiments R1 represents a group selected from phenyl, 2-fluorophenyl, 3-flurorophenyl, 4-fluorophenyl, 3-methylphenyl, 4-methylphenyl, 2,5-difluorophenyl, 2,6-difluorophenyl, 2,4,5-trifluorophenyl, 5-methylfuran-2-ylmethyl, 4-fluoro-2-methylphenyl, 3-fluoro-4-methoxyphenyl, 3-methyl-thiophen-2-ylmethyl, 4,5-dimethyl-thiophen-2-ylmethyl, thiophen-3-ylmethyl, 5-methyl-furan-2-ylmethyl, 5-methyl-2-trifluoromethyl-furan-3-ylmethyl, and 2,5-dimethyl-furan-3-ylmethyl, Also preferred are compounds of formula (II) as defined above wherein R2 represents a pent-4-enyl, pentyl, butyl, allyl, benzyl, thiophen-2-ylmethyl, thiophen-3-ylmethyl, furan-2-ylmethyl, furan-3-ylmethyl, phenethyl, cyclopentyl, cyclohexyl or cyclohexylmethyl group, the cyclic groups present in R2 being optionally substituted with one to three substitutents selected from fluorine, chlorine, bromine, methyl, methoxy, trifluoromethyl, ethyl, tert-butyl, hydroxy and cyano.

In particularly preferred embodiments R2 represents a group selected from 3-fluorobenzyl, 2,4,5-trifluorobenzyl, 3,4,5-trifluorobenzyl, 5-Bromothiophen-2-ylmethyl, 3,4-dimethoxyphenylethyl, 3-methylthiophen-2-ylmethyl, thiophen-3-ylmethyl, 4-bromo-5-methylthiophen-2-ylmethyl, 4,5-dimethylfuran-2-ylmethyl, furan-3-ylmethyl, 2-fluoro-4-methoxybenzyl, 2-(4-fluorophenyl)ethyl, butyl, pent-4-enyl and cyclopentyl.

Further preferred compounds of formula (II) are those wherein A is —CH2-, m and n are both 0, and B represents a group selected from straight or branched, optionally substituted lower alkyl, hydroxy, straight or branched, optionally substituted lower alkoxy, cyano, nitro, —CH═CR'R", —C(O)OR', —OC(O)R', —SC(O)R', —C(O)NR'R", —NR'C(O)OR", —NR'C(O)NR", cycloalkyl, phenyl, riaphthanelyl, 5,6,7,8-tetrahydronaphthanelyl, benzo[1,3]dioxolyl, heteroaryl or heterocyclyl; R' and R" being as defined above; and wherein the cyclic groups represented by B are optionally substituted by one, two or three substitutuents selected from halogen, hydroxy, straight or branched, optionally substituted lower alkyl, phenyl, —OR', —SR', —NR'R", —NHCOR', —CONR'R", —CN, —NO2 and —COOR'; R' and R" being as defined above;

In other embodiments of formula (II) A is —CH2-, B is as defined above and at least one of m or n is not 0.

Also preferred are compounds of formula (II) wherein B represents a thiophen-2-yl group or a phenyl group which is optionally substituted with one to three substituents selected from halogen atoms, or hydroxy, methyl, —CH2OH, —OMe, —NMe2, —NHCOMe, —CONH2, —CN, —NO2, —COOMe, or —CF3 groups. Most preferred are compounds wherein B represents a phenyl, 4-fluorophenyl, 3-hydroxyphenyl or thiophen-2-yl group.

In particularly preferred compounds of formula (II) n=0 or 1; m is an integer from 1 to 6; and A represents a —CH2-, —CH═CH—, —CO, —NMe, —O— or —S— group. Most preferred are compounds wherein m is 1, 2 or 3 and A represents a —CH2-, —CH═CH—, or —O— group.

Preferably, in compounds of formula (II) the sequence B—CH$_2$)$_n$-A-(CH$_2$)$_m$— represents a group selected from 3-phenoxypropyl, 2-phenoxyethyl, 3-phenylallyl, phenethyl, 3-phenylpropyl, 3-(3-hydroxyphenoxy)propyl, 3-(4-fluorophenoxy)propyl, 3-thiophen-2-ylpropyl, allyl, heptyl, 3-cyanopropyl and methyl.

X- represents in the preferred embodiments of formula (II) a chloride, bromide, trifluoroacetate or methanesulphonate anion.

Also preferred are compounds of formula (I) or (II) wherein p is 2 and/or wherein the azabicyclic ring is substituted in the 3-position.

The compounds of the present invention represented by formula (I) and salts thereof such as those represented by formula (II), may have one or more asymmetric carbons. All possible stereoisomers are included, such as compounds of formula (I) or (II) wherein the carbon at the 3-position of the azabicyclic ring has either R or S configuration. All single isomers and mixtures of the isomers fall within the scope of the present invention.

The following compounds of general formula (I) are intended to illustrate the general scope of the present invention.

(3-Fluorobenzyl)-(3-fluorophenyl)carbamic acid (3R)-1-azabicyclo[2.2.2]oct-3-yl ester m-Tolyl-2,4,5-trifluorobenzyl)carbamic acid (3R)-1-azabicyclo[2.2.2]oct-3-yl ester
(3-Fluorophenyl)-(3,4,5-trifluorobenzyl)carbamic acid (3R)-1-azabicyclo[2.2.2]oct-3-yl ester
Cyclohexylmethyl-(2-fluorophenyl)carbamic acid (3R)-1-azabicyclo[2.2.2]oct-3yl ester [2-(3,4-Dimethoxyphenyl)ethyl]-(5methylfuran-2-ylmethyl)carbamic acid (3R)-1-azabicyclo[2.2.2]oct-3yl ester
(5-Bromothiophen-2-ylmethyl)-(2,4,5-trifluorophenyl)carbamic acid (3R)-1-azabicyclo[2.2.2]oct-3-yl ester
(4-Fluoro-2-methylphenyl)-(3-methylthiophen-2-ylmethyl)carbamic acid (3R)-1-azabicyclo[2.2.2]oct-3-yl ester
(3-Fluoro-4-methoxyphenyl)thiophen-3-ylmethylcarbamic acid (3R)-1-azabicyclo[2.2.2]oct-3-yl ester
Thiophen-3-ylmethyl-(2,4,5-trifluorobenzyl)carbamic acid (3R)-1-azabicyclo[2.2.2]oct-3-yl ester
(4-Bromo-5-methylthiophen-2-ylmethyl)-(3-methylthiophen-2-ylmethyl)carbamic acid (3R)-1-azabicyclo[2.2.2]oct-37-yl ester
(4,5-Dimethylfuran-2-ylmethyl)-(5-methylfuran-2-ylmethyl)carbamic acid (3R)-1-azabicyclo[2.2.2]oct-3-yl ester
Furan-3-ylmethyl-(5methyl-2-trifluoromethylfuran-3-ylmethyl)carbamic acid (3R)-1-azabicyclo[2.2.2]oct-3-yl ester
(2,6-Difluorophenyl)pent-4-enylcarbamic acid (3R)-1-azabicyclo[2.2.2]oct-3-yl ester
(2,5-Dimethylfuran-3-ylmethyl)-(2-fluoro-4-methoxybenzyl)carbamic acid (3R)-1-azabicyclo[2.2.2]oct-3-yl ester
[2-(4-Fluorophenyl)ethyl]-(3-methylthiophen-2-ylmethyl)carbamic acid (3R)-1-azabicyclo[2.2.2]oct-3yl ester
Butyl-(2,5-difluorophenyl)carbamic acid (3R)-1-azabicyclo[2.2.2]oct-3yl ester
Cyclopentyl-(4,5dimethylthiophen-2-ylmethyl)carbamic acid (3R)-1-azabicyclo[2.2.2]oct-3-yl ester Benzylphenylcarbamic acid 1-azabicyclo[2.2.2]oct-3-(R)yl ester
Benzyl(4-fluorophenyl)carbamic acid 1-azabicyclo[2.2.2]oct-(R)yl ester
Benzyl-p-tolylcarbamic acid 1-azabicyclo[2.2.2]oct-3-(R)yl ester
Butylphenylcarbamic acid 1-azabicyclo[2.2.2]oct-3-(R)yl ester
Phenylthiophen-2-ylmethylcarbamic acid 1-azabicyclo[2.2.2]oct-3-(R)yl ester
Phenethylphenylcarbamic acid 1-azabicyclo[2.2.2]oct-3-(R)yl ester
Pentylphenylcarbamic acid 1-azabicyclo[2.2.2]oct-3-(R)yl ester
Pent-4-enylphenylcarbamic acid 1-azabicyclo[2.2.2]oct-3-(R)yl ester
Phenylthiophen-3-ylmethylcarbamic acid 1-azabicyclo[2.2.2]oct-3-(R)yl ester
Butylthiophen-2-ylmethylcarbamic acid 1-azabicyclo[2.2.2]oct-3-(R)yl ester
Bis-thiophen-2-ylmethylcarbamic acid 1-azabicyclo[2.2.2]oct-3-(R)yl ester
Furan-2-ylmethyl-2-thiophen-2-ylmethylcarbamic acid 1-azabicyclo[2.2.2]oct-3-(R)yl ester
Allylthiophen-2-ylmethylcarbamic acid 1-azabicyclo[2.2.2]oct-3-(R)yl ester
Cyclopentylthiophen-2-ylmethylcarbamic acid 1-azabicyclo[2.2.2]oct-3-(R)yl ester
Furan-2-ylmethylphenylcarbamic acid 1-azabicyclo[2.2.2]oct-3-(R)yl ester
Bis-furan-2-ylmethylcarbamic acid 1-azabicyclo[2.2.2]oct-3-(R)yl ester
Benzylphenylcarbamic acid 1-azabicyclo[2.2.1]hept-4-yl ester
Benzylphenylcarbamic acid 1-azabicyclo[2.2.2]oct-4-yl ester
(5-Ethylthiophen-2-ylmethyl)-(3methylthiophen-2-ylmethyl)carbamic acid (3R)-1-azabicyclo[2.2.2]oct-3-yl ester
Cyclopentyl-(5ethylthiophen-2-ylmethyl)carbamic acid (3R)-1-azabicyclo[2.2.2]oct-3-yl ester and pharmaceutically acceptable salts thereof.

The following salts of general formula (II) are intended to illustrate the general scope of the present invention.

(3R)-3-[(3-Fluorobenzyl)-(3-fluorophenyl)carbamoyloxy]-1-(2-phenoxyethyl)-1-azoniabicyclo[2.2.2]octane bromide
(3R)-3-[(3-Fluorobenzyl)-(3-fluorophenyl)carbamoyloxy]-1-(3-phenylpropyl)-1-azoniabicyclo[2.2.2]octane bromide
(3R)-1-(2-Phenoxyethyl)-3-[m-tolyl-(2,4,5trifluorobenzyl)carbamoyloxy]-1-azoniabicyclo[2.2.2]octane bromide
(3R)-1-(3-Phenylpropyl)-3-[m-tolyl-2,4,5-trifluorobenzyl)carbamoyloxy]-1-azoniabicyclo[2.2.2]octane bromide
(3R)-3-[(3-Fluorophenyl)-(3,4,5-trifluorobenzyl)carbamoyloxy]-1-(2-phenoxyethyl)-1-azoniabicyclo[2.2.2]octane bromide
(3R)-3-[Cyclohexylmethyl-(2-fluorophenyl)carbamoyloxy]-1-(2-phenoxyethyl)-1-azoniabicyclo[2.2.2]octane bromide
(3R)-3-[Cyclohexylmethyl-(2-fluorophenyl)carbamoyloxy]-1-(3-phenylpropyl)-1-azoniabicyclo[2.2.2]octane bromide
(3R)-1-Allyl-3-[[2-(3,4dimethoxyphenyl)ethyl]-(5-methylfuran-2-ylmethyl)carbamoyloxy]-1-azoniabicyclo[2.2.2]octane bromide (3R)-3-[(5-Bromothiophen-2-ylmethyl)-(2,4,5-trifluorophenyl)carbamoyloxy]-1-(3-phenoxypropyl)-1-azoniabicyclo[2.2.2]octane trifluoroacetate
(3R)-3-[[2-(3,4-dimethoxyphenyl)ethyl-(5-methylfuran-2-ylmethyl)carbamoyloxy]-1-(4-ethoxycarbonylbutyl)-1-azoniabicyclo[2.2.2]octane trifluoroacetate
(3R)-3-[[2-(3,4-dimethoxyphenyl)ethyl]-(5-methylfuran-2-ylmethyl)carbamoyloxy]-1-(4-ethoxycarbonylbutyl)-1-azoniabicyclo[2.2.2]octane formate
(3R)-3-[(4-Fluoro-2-methylphenyl)-(3-methylthiophen-2-ylmethyl)carbamoyloxy]-1-(2-phenoxyethyl)-1-azoniabicyclo[2.2.2]octane trifluoroacetate
(3R)-3-[(4-Fluoro-2-methylphenyl)-(3-methylthiophen-2-ylmethyl)carbamoyloxy]-1-(2-phenoxyethyl)-1-azoniabicyclo[2.2.2]octane bromide
(3R)-3-[(3-Fluoro-4-methoxyphenyl)thiophen-3-ylmethylcarbamoyloxy]-1-(3-phenylallyl)-1-azoniabicyclo[2.2.2]octane trifluoroacetate
(3R)-3-[(3-Fluoro-4-methoxyphenyl)thiophen-3-ylmethylcarbamoyloxy]1-(3-phenylallyl)-1-azoniabicyclo[2.2.2]octane bromide
(3R)-1-Phenethyl-3-[thiophen-3-ylmethyl-(2,4,5-trifluorobenzyl)carbamoyloxy]-1-azoniabicyclo[2.2.2]octane trifluoroacetate
(3R)-3-[(4-Bromo5-methylthiophen-2-ylmethyl)-(3-methylthiophen-2-ylmethyl)carbamoyloxy]-1-(3-phenylpropyl)-1-azoniabicyclo[2.2.2]octane trifluoroacetate
(3R)-3-[(4,5-Dimethylfuran-2-ylmethyl)-5-methylfuran-2-ylmethyl)carbamoyloxy]-1-[3-(3-hydroxyphenoxy)propyl]-1-azoniabicyclo[2.2.2]octane trifluoroacetate
(3R)-1-[3-(4-Fluorophenoxy)propyl]-3-[furan-3-ylmethyl-(5-methyl-2-trifluoromethylfuran-3-ylmethyl)carbamoyloxy]-1-azoniabicyclo[2.2.2]octane trifluoroacetate
(3R)-3-[(2,5-Dimethylfuran-3-ylmethyl)-(2-fluoro-4-methoxybenzyl)carbamoyloxy]-1-(3-thiophen-2-ylpropyl)-1-azoniabicyclo[2.2.2]octane trifluoroacetate
(3R)-1-Allyl-3-[2-(4-fluorophenyl)ethyl]-(3-methylthiophen-2-ylmethyl)carbamoyloxy]-1-azoniabicyclo[2.2.2]octane trifluoroacetate
(3R)-1-Allyl-3-[2-(4-fluorophenyl)ethyl]-(3-methylthiophen-2-ylmethyl)carbamoyloxy]-1-azoniabicyclo[2.2.2]octane bromide
(3R)-3-[Butyl-(2,5-difluorophenyl)carbamoyloxy]-1-heptyl-1-azoniabicyclo[2.2.2]octane trifluoroacetate
(3R)-1-(3-cyanopropyl)-3-[(2,6-difluorophenyl)pent-4-enylcarbamoyloxy]-1-azoniabicyclo[2.2.2]octane trifluoroacetate
(3R)-3-[Cyclopentyl-(4,5-dimethylthiophen-2-ylmethyl)carbamoyloxy]-1-methyl-1-azoniabicyclo[2.2.2]octane trifluoroacetate
3-(R)(Benzylphenylcarbamoyloxy)-1-(3-phenylallyl)-1-azoniabicyclo[2.2.2]octane; bromide
1-Allyl-3-(R)(benzylphenylcarbamoyloxy)-1-azoniabicyclo[2.2.2]octane; bromide
3-(R)(Benzylphenylcarbamoyloxy)-1-phenethyl-1-azoniabicyclo[2.2.2]octane; bromide
3-(R)(Benzylphenylcarbamoyloxy)-1-(3-thiophen-2-ylpropyl)-1-azoniabicyclo[2.2.2]octane; bromide
3-(R)(Benzylphenylcarbamoyloxy)-1-(3-phenylpropyl)-1-azoniabicyclo[2.2.2]octane; bromide
3-(R)(Benzylphenylcarbamoyloxy)-1-(2-phenoxyethyl)-1-azoniabicyclo[2.2.2]octane; bromide
3-(R)(Butylphenylcarbamoyloxy)-1-(3-phenylallyl)-1-azoniabicyclo[2.2.2]octane; bromide
1-Allyl-3-(R)(butylphenylcarbamoyloxy)-1-azoniabicyclo[2.2.2]octane; bromide
3-(R)(Butylphenylcarbamoyloxy)-1-(2-phenoxyethyl)-1-azoniabicyclo[2.2.2]octane; bromide
3-(R)(Butylphenylcarbamoyloxy)-1-[3-(3-hydroxyphenoxy)propyl]-1-azoniabicyclo[2.2.2]octane; bromide
3-(R)(Butylphenylcarbamoyloxy)-1-[3-(4-fluorophenoxy)propyl]-1-azoniabicyclo[2.2.2]octane; bromide
3-(R)(Butylphenylcarbamoyloxy)-1-(3-thiophen-2-ylpropyl)-1-azoniabicyclo[2.2.2]octane; bromide
3-(R)(Butylphenylcarbamoyloxy)-1-(3-phenylpropyl)-1-azoniabicyclo[2.2.2]octane; bromide
3-(R)(Phenylthiophen-2-ylmethylcarbamoyloxy)-1-(3-thiophen-2-ylpropyl)-1-azoniabicyclo[2.2.2]octane; bromide
1-(2-Phenoxy-ethyl)-3-R)-(phenyl-thiophen-2-ylmethyl-carbamoyloxy)-1-azoniabicyclo[2.2.2]octane; bromide
1-Allyl-3-(R)(phenylthiophen-2-ylmethylcarbamoyloxy)-1-azoniabicyclo[2.2.2]octane; bromide
3-(R)(Phenethylphenylcarbamoyloxy)-1-(2-phenoxyethyl)-1-azoniabicyclo[2.2.2]octane; trifluoroacetate
1-Heptyl-3-(R)(pent-4-enylphenylcarbamoyloxy)-1-azoniabicyclo[2.2.2]octane; trifluoroacetate
1-Allyl-3-R-(phenyl-thiophen-3-ylmethyl-carbamoyloxy)-1-azonia-bicyclo[2.2.2]octane; trifluoroacetate
3-(R)(phenylthiophen-3-ylmethylcarbamoyloxy)-1-(3-thiophen-2-ylpropyl)-1-azoniabicyclo[2.2.2]octane; bromide
1-(2-Phenoxyethyl)-3-(R)(phenylthiophen-3-ylmethylcarbamoyloxy)-1-azoniabicyclo[2.2.2]octane; bromide
3-(R)(Bis-thiophen-2-ylmethylcarbamoyloxy)-1-3-phenyl-propyl)-1-azoniabicyclo[2.2.2]octane; bromide
3-(R)(Bis-thiophen-2-ylmethylcarbamoyloxy)-1-(3-thiophen-2-ylpropyl)-1-azoniabicyclo[2.2.2]octane; bromide
1-Allyl-3-(R)(allylthiophen-2-ylmethylcarbamoyloxy)-1-azoniabicyclo[2.2.2]octane; trifluoroacetate
3-(R)(Cyclopentylthiophen-2-ylmethylcarbamoyloxy-1-3-phenylpropyl)-1-azonia bicyclo[2.2.2]octane; trifluoroacetate
3-(R)(Furan-2-ylmethylphenylcarbamoyloxy)-1-(3-phenylpropyl)-1-azoniabicyclo[2.2.2]octane; trifluoroacetate
1-Allyl-3-(R)(bis-furan-2-ylmethylcarbamoyloxy)-1-azoniabicyclo[2.2.2]octane; trifluoroacetate
(3R)-3-[(3-Fluorophenyl)-(3,4,5-trifluorobenzyl)carbamoyloxy]-1-(3-phenylpropyl)-1-azoniabicyclo[2.2.2]octane bromide
(3R)-3-[(5-Ethylthiophen-2-ylmethyl)-(3-methylthiophen-2-ylmethyl)carbamoyloxy]-1-(3-phenylpropyl)-1-azoniabicyclo[2.2.2]octane bromide
(3R)-3-[Cyclopentyl-(5-ethylthiophen-2-ylmethyl)carbamoyloxy]-1-methyl-1-azoniabicyclo[2.2.2]octane bromide Particularly preferred individual compounds of formula (I) include:
[2-(3,4-Dimethoxyphenyl)ethyl]-(5-methylfuran-2-ylmethyl)carbamic acid (3R)-1-azabicyclo[2.2.2]oct-3-yl ester
(5-Bromothiophen-2-ylmethyl)-(2,4,5-trifluorophenyl)carbamic acid (3R)-1-azabicyclo[2.2.2]oct-3-yl ester
(4-Fluoro-2-methylphenyl)-(3-methylthiophen-2-ylmethyl)carbamic acid (3R)-1-azabicyclo[2.2.2]oct-3-yl ester
(3-Fluoro-4-methoxyphenyl)thiophen-3-ylmethylcarbamic acid (3R)1-azabicyclo[2.2.2]oct-3-yl ester
Thiophen-3-ylmethyl-(2,4,5-trifluorobenzyl)carbamic acid (3R)-1-azabicyclo[2.2.2]oct-3-yl ester
(4-Bromo-5-methylthiophen-2-ylmethyl)-(3-methylthiophen-2-ylmethyl)carbamic acid (3R)-1-azabicyclo[2.2.2]oct-3-yl ester (4,5-Dimethylfuran-2-ylmethyl)-(5-methylfuran-2-ylmethyl)carbamic acid (3R)-1-azabicyclo[2.2.2]oct-3-yl ester Furan-3-ylmethyl-(5methyl-2-trifluoromethylfuran-3-ylmethyl)carbamic acid (3R)-1-azabicyclo[2.2.2]oct-3-yl ester (2,5-Dimethylfuran-3-ylmethyl)-(2-fluoro-4-methoxybenzyl)carbamic acid (3R)-1-azabicyclo[2.2.2]oct-3-yl ester

[2-(4-Fluorophenyl)ethyl]-(3-methylthiophen-2-ylmethyl) carbamic acid (3R)-1-azabicyclo[2.2.2]oct-3-yl ester Butyl-(2,5-difluorophenyl)carbamic acid (3R)-1-azabicyclo[2.2.2]oct-3-yl ester (2,6-Difluorophenyl)pent-4-enylcarbamic acid (3R)-1-azabicyclo[2.2.2]oct-3yl ester Cyclopentyl-(4,5-dimethylthiophen-2-ylmethyl)carbamic acid (3R)-1-azabicyclo[2.2.2]oct-3-yl ester (5-Ethylthiophen-2-ylmethyl)-(3-methylthiophen-2-ylmethyl)carbamic acid (3R)-1-azabicyclo[2.2.2]oct-3yl ester Particularly preferred individual compounds of formula (II) include:

(3R)-3-[(3-Fluorobenzyl)-(3-fluorophenyl)carbamoyloxy]-1-(2-phenoxyethyl)-1-azoniabicyclo[2.2.2]octane bromide (3R)-3-[(3-Fluorobenzyl)-(3-fluorophenyl)carbamoyloxy]-1-(3-phenylpropyl)-1-azoniabicyclo[2.2.2]octane bromide (3R)-1-(2-Phenoxyethyl)-3-[m-tolyl-(2,4,5-trifluorobenzyl)carbamoyloxy]-1-azoniabicyclo[2.2.2]octane bromide (3R)-1-(3Phenylpropyl)-3-[m-tolyl-(2,4,5-trifluorobenzyl)carbamoyloxy]-1-azoniabicyclo[2.2.2]octane bromide (3R)-3-[(3-Fluorophenyl)-(3,4,5-trifluorobenzyl)carbamoyloxy]-1-(2-phenoxyethyl)-1-azoniabicyclo[2.2.2]octane bromide (3R)-1-Allyl-3-[[2-(3,4-dimethoxyphenyl)ethyl]-(5-methylfuran-2-ylmethyl)carbamoyloxy]-1-azoniabicyclo[2.2.2]octane bromide (3R)-3-[(5-Bromothiophen-2-ylmethyl)-2,4,5-trifluorophenyl)carbamoyloxy]1-(3-phenoxypropyl)-1-azoniabicyclo[2.2.2]octane trifluoroacetate (3R)-3-[[2-(3,4-dimethoxyphenyl)ethyl[-(5-methylfuran-2-ylmethyl)carbamoyloxy]-1-(4-ethoxycarbonylbutyl)-1-azoniabicyclo[2.2.2]octane trifluoroacetate (3R)-3-[(4-Fluoro-2-methylphenyl)-(3-methylthiophen-2-ylmethyl)carbamoyloxy]-1-(2-phenoxyethyl)-1-azoniabicyclo[2.2.2]octane trifluoroacetate (3R)-3-[(3-Fluoro-4-methoxyphenyl)thiophen-3-ylmethylcarbamoyloxy]-1-(3-phenylallyl)-1-azoniabicyclo[2.2.2]octane trifluoroacetate (3R)-1-Phenethyl-3-[thiophen-3-ylmethyl-(2,4,5-trifluorobenzyl)carbamoyloxy]-1-azoniabicyclo[2.2.2]octane trifluoroacetate (3R)-3-[(4-Bromo-5-methylthiophen-2-ylmethyl)-(3-methylthiophen-2-ylmethyl)carbamoyloxy]-1-(3-phenylpropyl)-1-azoniabicyclo[2.2.2]octane trifluoroacetate (3R)-3-[(4,5-Dimethylfuran-2-ylmethyl)-(5-methylfuran-2-ylmethyl)carbamoyloxy]-1-[3-(3-hydroxyphenoxy)propyl]-1-azoniabicyclo[2.2.2]octane trifluoroacetate (3R)-1-[3-(4-Fluorophenoxy)propyl]-3-[furan-3-ylmethyl-(5-methyl-2-trifluoromethylfuran-3-ylmethyl)carbamoyloxy]-1-azoniabicyclo[2.2.2]octane trifluoroacetate (3R)-3-[(2,5-Dimethylfuran-3-ylmethyl)-(2-fluoro-4-methoxybenzyl)carbamoyloxy]-1-(3-thiophen-2-ylpropyl)-1-azoniabicyclo[2.2.2]octane trifluoroacetate (3R)-1-Allyl-3-[2-(4-fluorophenyl)ethyl]-(3-methylthiophen-2-ylmethyl)carbamoyloxy]-1-azoniabicyclo[2.2.2]octane trifluoroacetate (3R)-3-[Butyl-(2,5-difluorophenyl)carbamoyloxy]-1-heptyl-1-azoniabicyclo[2.2.2]octane trifluoroacetate (3R)-1-(3-cyanopropyl)-3-[(2,6-difluorophenyl)pent-4-enylcarbamoyloxy]-1-azoniabicyclo[2.2.2]octane trifluoroacetate (3R)-3-[Cyclopentyl-(4,5-dimethylthiophen-2-ylmethyl) carbamoyloxy]-1-methyl-1-azoniabicyclo[2.2.2]octane trifluoroacetate (3R)-3-[(3-Fluorophenyl)-(3,4,5-trifluorobenzyl)carbamoyloxy]-1-(3-phenylpropyl)-1-azoniabicyclo[2.2.2]octane bromide (3R)-3-[(5-Ethylthiophen-2-ylmethyl)-(3-methylthiophen-2-ylmethyl)carbamoyloxy]-1-3-phenylpropyl)-1-azoniabicyclo[2.2.2]octane bromide (3R)-3-[[2-(3,4-dimethoxyphenyl)ethyl]-(5-methylfuran-2-ylmethyl)carbamoyloxy]-1-(4-ethoxycarbonylbutyl)-1-azoniabicyclo[2.2.2]octane formate (3R)-3-[(4-Fluoro-2-methylphenyl)-(3-methylthiophen-2-ylmethyl)carbamoyloxy]-1-(2-phenoxyethyl)-1-azoniabicyclo[2.2.2]octane bromide (3R)-3-[(3-Fluoro-4-methoxyphenyl)thiophen-3-ylmethylcarbamoyloxy]-1-(3-phenylallyl)-1-azoniabicyclo[2.2.2] octane bromide (3R)-1-Allyl-3-[2-(4-fluorophenyl)ethyl]-(3-methylthiophen-2-ylmethyl)carbamoyloxy]-1-azoniabicyclo [2.2.2]octane bromide The present invention also provides processes for preparing compounds of formulas (I) and (II).

Compounds of general formula (I) may be prepared by method (a) illustrated in the following scheme and detailed in the experimental section.

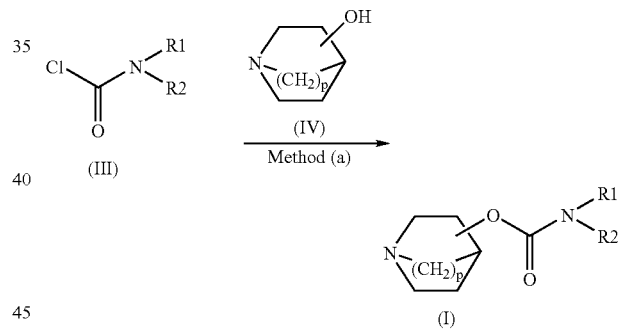

In formulas (I), (III) and (IV), R1, R2 and p are as defined above.

Compounds of general formula (III) may be prepared from the corresponding secondary amines following the standard method (b) described in literature.

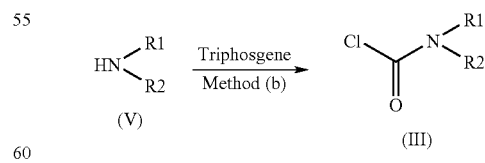

Amines of general formula (V) that are not commercially available may be prepared by synthesis according to standard methods, such as alkylation of anilines or reductive alkylation. For example, amines wherein R1 is a substituted thiophen-2-ylmethyl or a substituted furan-2-ylmethyl and R2 is as defined above, may be obtained by reductive alkylation. The corresponding aldehyde is treated with the corresponding primary amine to form the imine, which is reduced with sodium borohydride in MeOH to obtain the secondary amine.

The carbamates of formula (I) may be converted to pharmaceutically acceptable salts by methods known in the art. Typically, a carbamate of formula (I) is treated with an inorganic or organic acid such as fumaric, tartaric, formic, succinic or hydrochloric acid.

The quaternary ammonium derivatives of general formula (II), may be prepared by reaction of an alkylating agent of general formula (VI) with compounds of general formula (I), as described in the following scheme. In formulas (I), (II) and (V(I), R1, R2, A, B, X, n, m and p are as defined above.

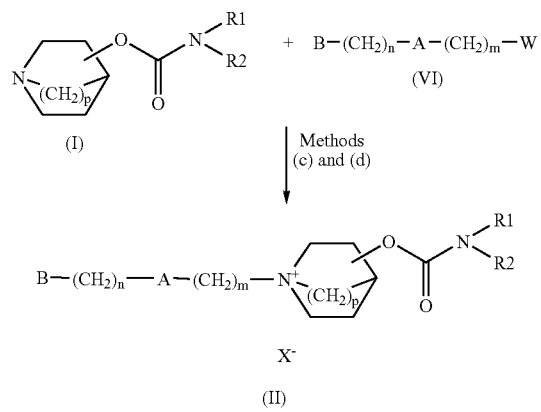

In formula (VI), W represents any suitable leaving group, such as a group X as defined above. Preferably, W represents a group X.

This alkylation reaction may be carried out by two different experimental procedures, (c) and (d) which are described in the experimental section below. In particular method (d) provides a new experimental process, using solid phase extraction methodologies that allow the parallel preparation of several compounds. If W represents a group other than X, the quaternary ammonium salt of formula (II) is produced from the product of method (c) or (d) by carrying out an exchange reaction according to standard methods to replace the anion with the desired anion $X^-$.

Methods (c) and (d) are described in the experimental section. Compounds of general formula (VI) which are not commercially available have been prepared by synthesis according to standard methods. For example, compounds wherein n=0 and A=-O—, —S— or —NR4, wherein R4 is as defined above, were obtained by reaction of the corresponding alcohol, thiol or amine derivative or its sodium or potassium salt with an alkylating agent of general formula Y—(CH$_2$)m-W, wherein W may be a halogen and Y may be a halogen or a sulphonate ester. In other examples, compounds of general formula (V), where n>=1 were synthesised from the corresponding alcohol derivative of general formula (VII) by known methods.

Compounds of formula (IV) could be:
4-hydroxy-1-azabicyclo[2.2.1]heptane, described in WO93/15080
4-hydroxy-1-azabicyclo[2.2.2]octane, described in Grob, C. A. et. al. Helv. Chim. Acta (1958), 41, 1184-1190
(3R)-3-hydroxy-1-azabicyclo[2.2.2]octane or (3S)-3-hydroxy-1-azabicyclo[2.2.2]octane, described in Ringdahl, R. Acta Pharm Suec. (1979), 16, 281-283 and commercially available from CU Chemie Uetikon GmbH.

The structures of the prepared compounds were confirmed by $^1$H-NMR and MS. The NMR were recorded using a Varian 300 MHz instrument and chemical shifts are expressed as parts per million (δ) from the internal reference tetramethyl silane. Their purity was determined by HPLC, using reverse phase chromatography on a Waters instrument. Molecular ions were obtained by electrospray ionization mass spectrometry on a Hewlett Packard instrument. HPLC-MS experiments were performed on a Gilson instrument equipped with a binary pump (Gilson piston pump 321); a vacuum degasser (Gilson 864); an injector-fraction collector (Gilson liquid handler 215); two injection modules, analytical and preparative (Gilson 819); a valve (Gilson Valvemate 7000); a 1/1000 splitter (Acurate by LC Packings); a make-up pump (Gilson 307); a diode array detector (Gilson 170) and a MS detector (a Thermoquest Finnigan aQa, a quadrupole mass spectrometer with ES an APCI ionisation modes). The HPLC-MS instrument was controlled by an IBM PC.

Method (a)

EXAMPLE 1

Preparation of butylphenylcarbamic acid (3R)-1-azabicyclo[2.2.2]oct-3-yl ester 0.65 g (28.50 mmol) of sodium was added to 70 ml of dry toluene. The suspension was refluxed with vigorous stirring. When all the sodium was melted, 3.60 g (28.30 mmol) of (3R)-3-hydroxy-1-azabicyclo[2.2.2]octane was added and stirring continued for 2 hours, by which time all the sodium had reacted to form the alcoholate. 6.00 g (28.30 mmol) of Phenylbutylcarbamoyl chloride (Intermediate I-1) dissolved in 30 ml of toluene was then slowly added. The mixture was refluxed for one hour, and then the reaction was stirred overnight at room temperature. The suspension was filtered and the filtrate evaporated. Ether was added to the residue and stirred for 10 min. The suspension was filtered and the filtrate concentrated in vacuo to obtain 7.18 g of brown oil. This product was purified by column chromatography (silica gel, chloroform/ethanol/ammonia 140:8:1) to yield 1.78 g (5.89 mmol) (22%) of a pure product, structure confirmed by $^1$H-NMR.

$^1$H-NMR (300 MHz, CDCl3): δ 0.9 (m, 3H), 1.3 (m, 4H), 1.5 (m, 4H), 1.9 (s, 1H), 2.7 (m, 5H), 3.2 (m, 1H), 3.7 (m, 2H), 4.7 (m, 1H), 7.2-7.4 (m, 5H); MS [M+1]$^+$: 303.

EXAMPLE 2

Preparation of cyclopentylthiophen-2-ylmethylcarbamic acid (3R)-1-azabicyclo[2.2.2]oct-3-yl ester 0.57 g (24.59 mmol) of sodium was added to 70 ml of dry toluene. The suspension was refluxed with vigorous stirring. When all the sodium was melted, 3.11 g (24.42 mmol) of (3R)-3-hydroxy-1-azabicyclo[2.2.2]octane was added and stirred for 2 hours, by which time all the sodium had reacted to form the alcoholate. 4.96 g (20.35 mmol) of cyclopentylthiophen-2-ylmethylcarbamoyl chloride (Intermediate I-2) dissolved in 30 ml of toluene was then slowly added. The mixture was refluxed for five hours, and then the reaction was stirred overnight at room temperature. The suspension was filtered and the filtrate washed with water. The organic layer was extracted with 20 % HCl and the aqueous layer basified with 8N NaOH and extracted with ethyl acetate. The organic layer was washed with water, dried over anhydrous $Na_2SO_4$ and evaporated. The oil obtained (4.50 g) was purified by column chromatography (silica gel, chloroform/ethanol/ammonia 225:8:1) to obtain 2.25 g (6.73 mmol) (33%) of a pure product, structure confirmed by $^1$H-NMR.

1H-NMR (300 MHz, DMSO-$d_6$): δ 1.20-1.40 (m, 1H), 1.45-1.72 (m, 11H), 1.89 (bs, 1H), 2.45-2.62 (m, 5H), 3.03-3.10 (m, 1H), 4.22 (bs, 1H), 4.50-4.63 (m, 3H), 6.93-6.99 (m, 2H), 7.38 (m, 1H).; MS [M+1]$^+$: 335.

EXAMPLE 3

Preparation of Benzylphenylcarbamic acid 1-azabicyclo[2.2.1]hept-4-yl ester

In a two necked flask under nitrogen, 3 ml of THF and 150 mg (1.33 mmoles) of 4-hydroxy-1-azabicyclo[2.2.1]heptane were placed. The suspension was cooled to −60° C. and 0.7 ml (1.46 mmoles) of LDA was added dropwise. After the addition the temperature was allowed to rise to 0° C. and was kept during two hours. A solution of 295 mg (1.20 mmoles) of benzylphenylcarbamoyl chloride in 2 ml of THF was added in 30 minutes. The reaction mixture was allowed to slowly warm to room temperature and stirred for 18 hours. The suspension was filtered and the filtrate concentrated under reduced pressure. The residue was extracted with dichloromethane and water. The organic layer was extracted with 2N HCl and the aqueous layer basified with 8N NaOH and extracted with dichloromethane. The organic layers were dried over anhydrous $Na_2SO_4$ and evaporated. The oil obtained (162 mg) was purified by HPLC-MS to obtain 4.86 mg (0.015 mmoles) 1.3% of a pure product as a formate, structure confirmed by $^1$H-NMR.

1H-NMR (300 MHz, DMSO-$d_6$): δ 1.86 (m, 4H), 2.65 (s, 2H), 2.77 (bs, 2H), 3.03 (bs, 2H), 4.84 (s, 2H), 7.14-7.32 (m, 10H). 8.19 (s, 1H); MS [M-HCOO]$^-$: 323.

EXAMPLE 4

Preparation of m-tolyl-(2,4,5-trifluorobenzyl)carbamic acid (3R)-1-azabicyclo[2.2.2]oct-3-yl ester 0.69 g (30 mmol) of sodium (in small portions) were added to 140 ml of dry toluene and the suspension was refluxed with vigorous stirring. When all the sodium was melted, 3.78 g (29.73 mmol) of (3R)-3-hydroxy-1-azabicyclo[2.2.2]octane were added in five portions, and the-suspension obtained was refluxed for 2 hours, by which time all the sodium had reacted to form the alcoholate. A solution of 8.11 g (25.85 mmol) of m-Tolyl-(2,4,5-trifluorobenzyl)carbamoyl chloride (Intermediate I-3) in 60 ml of toluene was then slowly added. The mixture obtained was refluxed for 3 hours, and stirred at room temperature for 64 more hours. After this time, the reaction mixture was filtered and the solution obtained was extracted with HCl 2N (2×125 ml). The aqueous layers were combined, basified with solid $K_2CO_3$ and extracted with $CHCl_3$. The organic layer was dried over anhydrous $MgSO_4$, filtered and evaporated. The oil obtained (6.30 g) was purified by column chromatography (silica gel, chloroform/ethanol 5:1) to obtain 3.05 g (29.2%) of a pure product as an oil, structure confirmed by $^1$H-NMR.

$^1$H-NMR (CDCl$_3$): δ 1.22-1.40 (m, 1H), 1.40-1.60 (m, 2H), 1.60-1.75 (m, 1H), 2.0 (m, 1H), 2.32 (s, 3H), 2.60-2.90 (m, 5H), 3.17-3.26 (m, 1H), 4.78-4.83 (m, 1H), 4.86 (s, 2H), 6.82-7.0 (m, 3H), 7.03-7.07 (m, 1H), 7.15-7.25 (m, 2H). MS [M+1]$^+$: 405

EXAMPLE 5

Preparation of [2-(4-Fluorophenyl)ethyl]-(3-methylthiophen-2-ylmethyl)carbamic acid (3R)-1-azabicyclo[2.2.2]oct-3-yl ester A mixture of 0.7 g (0.018 mol) of sodium hydride (60% dispersion in mineral oil) and 1.8 g (0.014 mol) of (3R)-3-hydroxy-1-azabicyclo[2.2.2]octane in 70 ml of toluene were refluxed for two hours in order to form the alcoholate. A suspension of a white solid was obtained. A solution of 4.5 g (0.014 mol) of [2-(4-Fluorophenyl)ethyl]-(3-methylthiophen-2-ylmethyl)carbamoyl chloride in 30 ml of toluene was then slowly added. The mixture obtained was refluxed for 2 hours, and stirred at room temperature for 64 hours more. After this time, the reaction mixture was cooled to 0-5° C., and 75 ml of water were carefully added under stirring. The organic phase was separated and extracted with HCl 2N (2×75 ml). The aqueous phases were combined, basified with NaOH 2N and extracted with toluene (2×75 ml). The organic layers were combined and the solution was concentrated to dryness. The oil obtained (1.80 g) was combined with 0.3 g from a previous preparation and purified by column chromatography (silica gel, $CH_2Cl_2$/MeOH/NH$_4$OH 90:10:1 as eluent) to obtain 1.1 g (13.7% global yield) of the title product as an oil, structure confirmed by $^1$H-NMR.

$^1$H-NMR (DMSO-$d_6$): δ 1.33 (m, 1H), 1.48 (m, 1H), 1.60 (m, 2H), 1.89 (m, 1H), 2.18 (s, 3H), 2.35-2.85 (m, 7H), 3.07 (m, 1H), 3.20-3.45 (m, 2H), 4.45-4.65 (m, 3H), 6.84 (m, 1H), 7.05-7.30 (m, 4H), 7.33 (m, 1H). MS [M+1]$^+$: 403.

[2-(4-Fluorophenyl)ethyl]-(3-methylthiophen-2-ylmethyl)carbamoyl chloride was prepared according to method (b) starting from the corresponding amine.

Method (b)

Carbamoyl chlorides of general formula (III) were prepared according to procedures described in the literature: M. Saraswati et al. Drug Development Research (1994), 31, 142-146; G. M. Shutske et al. J. Heterocycl. Chem. (1990), 27, 1617; GB 1246606; U.S. Pat. No. 2,762,796.

Preparation 1

Intermediate I-1—Preparation of butylphenylcarbamoyl chloride

To a solution of 6.72 g (45 mmol) of butylphenylamine in 50 ml of methylene chloride cooled to 10° C. was added slowly with stirring 6.67 g (22.5 mmol) of triphosgene in 40 ml of methylene chloride. The reaction was allowed to continue at room temperature for 27 hours. The solvent was evaporated and the residue extracted twice with n-hexane. The organic solution was concentrated in vacuo to yield 9.11 g (43.03 mmol) of a yellow oil (96%). $^1$H-NMR (CDCl$_3$): δ 0.9 (m, 3H), 1.3 (m, 2H), 1.6 (m, 2H), 3.7 (m, 2H), 7.2-7.4 (m, 5H).

Preparation 2

Intermediate I-2—Preparation of cyclopentylthiophen-2-ylmethylcarbamoyl chloride To a solution of 5.0 g (27.58 mmol) of cyclopentylthiophen-2-ylmethylamine in 40 ml of methylene chloride at 10° C. was added slowly with stirring 4.09 g (13.79 mmol) of triphosgene in 35 ml of methylene chloride. The reaction was allowed to continue stirring at room temperature for 64 hours, refluxed for 4 hours and 25 hours more at room temperature. The solvent was evaporated and the residue extracted with n-hexane. The organic solution was concentrated to yield 4.96 g (20.34 mmol) of a brown oil (74%). $^1$H-NMR (CDCl$_3$): δ 1.4 (m, 8H), 4.2 (bs, 1H), 4.5 (m, 2H), 6.8-7.3 (m, 3H).

Preparation 3

Intermediate I-3—Preparation of m-tolyl-(2,4,-trifluorobenzyl)carbamoyl chloride To a solution of 6.5 g (25.87 mmol) of m-tolyl-(2,4,5-trifluorobenzyl)amine (Intermediate I-7) in 45 ml of methylene chloride, cooled at −10° C., was added slowly with stirring a solution of 3.84 g (12.94 mmol) of triphosgene in 25 ml of methylene chloride. The reaction was allowed to warm to room temperature, stirred for 2 hours at this temperature and then refluxed for 10 hours. After this time the solid formed during the process was dissolved. The solvent was evaporated and the residue treated with n-hexane at −25° C. The soluble part was separated and filtered. The filtrate was concentrated in vacuo to yield 8.2 g of an oil. The structure was confirmed by $^1$H-NMR.

$^1$H-NMR (CDCl$_3$): δ 2.30 (s, 3H), 4.85 (s, 2H), 6.70-7.10 (m, 3H), 7.10-7.40 (m, 3H).

Preparation 4

Intermediate I-4—Preparation of 3-fluorophenyl-(3,4,5-trifluorobenzyl)carbamoyl chloride To a solution of 3.4 g (13.30 mmol) of 3-fluorophenyl-(3,4,5-trifluorobenzyl)amine (Intermediate I-8) in 25 ml of methylene chloride, cooled at −10° C., was added slowly with stirring a solution of 2.0 g (6.70 mmol) of triphosgene in 15 ml of methylene chloride. The reaction was allowed to warm to room temperature and stirred for 17 hours at this temperature. After this time the solid formed during the process was filtered and the filtrate was concentrated in vacuo. The obtained residue was treated with n-hexane at −25° C. The soluble part was separated and filtrated. The filtrate was concentrated in vacuo to dryness to give 2.65 g (62.8%) of the tide product as an oil. The structure was confirmed by $^1$H-NMR.

$^1$H-NMR (CDCl$_3$): δ 4.80 (s, 2H), 6.70-7.0 (m, 4H), 7.0-7.20 (m, 1H), 7.25-7.45 (m, 1H).

Preparations 5-12

Some other examples of compounds of formula (III) that have been prepared in the present invention according to method (b) are:

(3-Fluorobenzyl)-(3-fluorophenyl)carbamoyl chloride
Cyclohexylmethyl-(2-fluorophenyl)carbamoyl chloride
[2-(3,4-Dimethoxyphenyl)ethyl]-(5-methylfuran-2-ylmethyl)carbamoyl chloride
(5-Bromothiophen-2-ylmethyl)-(2,4,5-trifluorophenyl)carbamoyl chloride
(4-Fluoro-2-methylphenyl)-(3-methylthiophen-2-ylmethyl)carbamoyl chloride
(3-Fluoro-4-methoxyphenyl)thiophen-3-ylmethylcarbamoyl chloride
(4,5-Dimethylfuran-2-ylmethyl)-(5-methylfuran-2-ylmethyl)carbamoyl chloride
[2-(4-Fluorophenyl)ethyl]-(3-methylthiophen-2-ylmethyl)carbamoyl chloride

Preparation 13

Intermediate I-5—Preparation of [2-(3,4-Dimethoxyphenyl)ethyl]-(5-methylfuran-2-ylmethyl)amine To a solution of 4.82 g (26.6 mmol) of 2-(3,4-dimethoxyphenyl)ethylamine and 3.0 g (27.2 mmol) of 5-methylfuran-2-carbaldehyde in 65 ml of EtOH, 18.3 g of molecular sieves (0.3 nm) were added and the mixture was refluxed for 4 hours. After this time the reaction mixture was cooled to room temperature and filtered. The solution obtained was concentrated in vacuo to obtain an oil. This oil was dissolved in 65 ml of MeOH and 1.01 g (26.6 mmol) of NaBH$_4$ were added in small portions, maintaining the temperature of the reaction at room temperature. The mixture was stirred at this temperature for 16 hours more. After this time the solvent was evaporated in vacuo and the residue was treated with 150 ml of water and extracted twice with ether.

The organic layers were combined, washed with brine, dried over anhydrous MgSO$_4$, filtered and evaporated to dryness to give 6.05 g (82.6%) of the title product as an oil.

MS [M+1]$^+$: 276 $^1$H-NMR (CDCl$_3$): δ 2.25 (s, 3H), 2.70-2.95 (m, 4H), 3.75 (s, 2H), 3.85 (two singlets, 6H), 5.85 (m, 1H), 6.02 (m, 1H), 6.70-6.85 (m, 3H).

Preparation 14

Intermediate I-6—Preparation of (5-Bromothiophen-2-ylmethyl)-(2,4,5-trifluorophenyl)amine To a solution of 2 g (13.6 mmol) of 2,4,5-trifluorophenylamine and 2.66 g (13.9 mmol) of 5-bromothiophene-2-carbaldehyde in 30 ml of EtOH, 9.4 g of molecular sieves (0.3 nm) were added and the mixture was refluxed for 20 hours. After this time the reaction mixture was cooled to room temperature, filtered and the solvent was evaporated in vacuo. The oil obtained was dissolved in 30 ml of MeOH and 0.51 g (13.6 mmol) of NaBH$_4$ were added in small portions, maintaining the temperature of the reaction at room temperature. The mixture was stirred at this temperature for 20 more hours. After this time the solvent was evaporated in vacuo and the residue was treated with 100 ml of water and extracted twice with ether. The organic layers were combined, washed with brine, dried over anhydrous MgSO$_4$, filtered and evaporated to dryness to give 3.2 g of an oil. This 3.2 g were combined with 3.5 g obtained in a subsequent preparation and the total product obtained (6.7 g) was purified by chromatography on silica gel using mixtures of hexane/AcOEt 5:1→1:1 as eluent Appropriate fractions were combined to give 0.95 g of the title product as an oil. (global yield 8.2%).

MS [M+1]$^+$: 321,323 $^1$H-NMR (CDCl$_3$): δ 4.10 (bs, NH, 1H), 4.40 (s, 2H), 6.40-6.65 (m, 1H), 6.75-7.10 (m, 3H).

Preparation 15

Intermediate I-7—Preparation of m-Tolyl-(2,4,5-fluorobenzyl)amine

To a solution of m-tolylamine (3.26 g, 3.27 ml, 30.5 mmol) and 2,4,5-trifluorobenzaldehyde (5.0 g, 31.2 mmol) in 60 ml of EtOH, 21 g of molecular sieves (0.3 nm) were added and the mixture was refluxed for 3 hours. After this time the reaction mixture was cooled to room temperature and filtered. The solution obtained was concentrated in vacuo to obtain an oil. This oil was dissolved in 60 ml of MeOH and 1.15 g (30.5 mmol) of NaBH$_4$ were added in small portions, maintaining the temperature of the reaction at room temperature. The mixture was stirred at this temperature for 16 hours more. After this time the solvent was evaporated in vacuo and the residue was treated with 100 ml of water and extracted twice with ether. The organic layers were combined, washed with brine, dried over anhydrous MgSO$_4$, filtered and concentrated in vacuo to dryness to give 6.5 g (84.8%) of the title product as an oil (that solidified at low temperature). The structure was confirmed by $^1$H-RMN and MS.

GC/MS: [M]$^+$: 251 $^1$H-NMR (CDCl$_3$): δ 2.25 (s, 3H), 4.0 (bs, 1H), 4.35 (s, 2H), 6.35-6.65 (m, 3H), 6.85-7.40 (m, 3H).

Preparation 16

Intermediate I-8—Preparation of (3-Fluorophenyl)-(3,4,5trifluorobenzyl)amine A mixture of 3.7 g (3.2 ml, 33.3 mmol) of 3-fluorophenylamine, 2.5 g (11.1 mmol) of 5-(bromomethyl)-1,2,3-trifluorobenzene and 1.53 g (11.1 mmol) of K$_2$CO$_3$ in 30 ml of toluene, was refluxed during 5 h and stirred at room temperature during 16 hours more. After this time the mixture of reaction was filtered and the solid obtained was washed with toluene. The toluene solutions were combined, washed with water and brine, dried over MgSO$_4$, and concentrated in vacuo to dryness to give 5.0 g of an oily residue. This oil was treated with diethyl ether and the obtained solid was separated by filtration and discarded. The filtrate was concentrated to dryness and purified by Kugelrohr distillation at reduced pressure. After distillation of the excess of 3-fluorophenylamine (0.15 mm Hg, 100° C. oven), 2.40 g (84.8%) of the title product were distilled (0.15 mm Hg, 175-200° C. oven). Structure confirmed by MS and $^1$H-RMN.

GC/MS: [M]$^+$: 255 $^1$H-NMR (CDCl$_3$): δ 4.30 (s, 2H), 4.0-4.50 (bs, 1H), 6.20-6.55 (m, 3H), 6.80-7.25 (m, 3H).

3-fluorophenyl-(3,4,5-trifluorobenzyl)amine has also been prepared by reductive alkylation starting from 3,4,5-trifluorobenzaldehyde and 3-fluorophenylamine.

Preparations 17-22

Some other examples of compounds of formula (V) that have been prepared in the present invention are:
(3-Fluorobenzyl)-(3-fluorophenyl)amine
Cyclohexylmethyl-(2-fluorophenyl)amine
(4-Fluoro-2-methylphenyl)-(3-methylthiophen-2-ylmethyl)amine
(3-Fluoro-4-ethoxyphenyl)thiophen-3-ylmethylamine
(4,5-Dimethylfuran-2-ylmethyl)-(5-methylfuran-2-ylmethyl)amine
[2-(4-Fluorophenyl)ethyl](3-methylthiophen-2-ylmethyl)amine

Method (c)

EXAMPLE 6

Preparation of (3R)-3-(bis-thiophen-2-ylmethylcarbamoyloxy)-1-(3-thiophen-2-ylpropyl)-1-azoniabicyclo[2.2.2]octane, bromide 0.54 g (1.5 mmol) of bis-thiophen-2-ylmethylcarbamic add (3R)-1-azabicyclo[2.2.2]oct-3-yl ester, 7.5 ml of tetrahydrofuran and 0.46 g (2.25 mmol) of 2-(3-bromopropyl)thiophene were mixed. The solution was refluxed for 4 hours and stirred at room temperature for 116 hours. Ether was added and the suspension was stirred for 30 min. The solvent was extracted and more ether was added. This procedure was repeated several times in order to eliminate the alkylating agent. Finally the suspension was filtered and the residue dried in the vacuum oven. The yield was 0.69 g (1.22 mmol) (81%).

$^1$H-NMR (DMSO-d$_6$): 1.78-2.10 (m, 6H), 2.34 (bs, 1H), 2.82 (m, 2H), 3.21-3.46 (m, 7H), 3.89 (m, 1H), 4.54 (m, 4H), 5.06 (m, 1H), 6.95-7.01 (m, 4H), 7.07-7.11 (m, 2H), 7.38-7.49 (m, 3H); MS [M-Br]$^+$: 487; mp: 143° C.

EXAMPLE 7

Preparation of (3R)-1-(2-phenoxyethyl)-3-[m-tolyl-(2,4,5-trifluorobenzyl)carbamoyloxy]-1-azoniabicyclo[2.2.2]octane bromide 0.300 g (0.742 mmol) of m-tolyl-(2,4,5-trifluorobenzyl)carbamic add (3R)-1-azabicyclo[2.2.2]oct-3-yl ester, 7.0 ml of tetrahydrofuran and 0.253 g (1.258 mmol) of (2-bromoethoxy)benzene were mixed. The solution-was refluxed for 55 hours and allowed to continue stirring at room temperature during 16 more hours. After this time the solvent was evaporated in vacuo. Ether was added and the mixture stirred to obtain a solid. This solid was treated with ether several times in order to eliminate the residual alkylating agent. Finally the suspension was filtered and the solid obtains washed with ether and dried. The yield was 0.34 g (75.5%).

m.p.: 137.3-139.1° C. MS [M-Br]$^+$: 525 $^1$H-NMR(DMSO-d$_6$): δ 1.40-1.70 (m, 1H), 1.70-2.05 (m, 3H), 2-20 (m, 1H), 2.25 (s, 3H), 3.25-3.40 (m, 1H), 3.40-3.80 (m, 6H), 3.95-4.10 (m, 1H), 4.44 (m, 2H), 4.90 (m, 2H), 5.01 (m, 1H), 6.95-7.30 (m, 7H), 7.30-7.60 (m, 4H).

EXAMPLE 8

Preparation of (3R)-1-Allyl-3-[[2-(3,4-dimethoxyphenyl)ethyl]-(5-methylfuran-2-ylmethyl)carbamoyloxy]-1-azoniabicyclo[2.2.2]octane bromide 0.300 g (0.7 mmol) of [2-(3,4-Dimethoxyphenyl)ethyl]-(5-methylfuran-2-ylmethyl)carbamic acid (3R)-1-azabicyclo[2.2.2]oct-3-yl ester were dissolved in 5 ml of CHCl$_3$ and 3.5 ml of acetonitrile. To this solution 0.30 ml (0.423 g, 3.5 mmol) of allyl bromide were added and the mixture was stirred during 21 hours at room temperature under N$_2$ atmosphere. Solvents were evaporated. The residue was treated with ether several times to obtain an oil, which was redissolved in CHCl$_3$ and evaporated to dryness to give 0.365 g (94.8%) of the title product.

MS [M-Br]$^+$: 469

Method (d)

EXAMPLE 9

Preparation of (3R)-1-heptyl-3-(phenylthiophen-3-ylmethylcarbamoyloxy)-1-azoniabicyclo[2.2.2]octane; trifluoroacetate 30 mg (0.08 mmols) of phenylthiophen-3-yl methyl carbamic add (3R)-1-azabicyclo[2.2.2]oct-3-yl ester were dissolved in 1 ml of DMSO. To this solution 75 mg (0.40 mmol) of heptyl bromide were added. After stirring overnight at room temperature, the mixture was purified by solid phase extraction with a cation exchange Mega Bond Elut cartridge, previously conditioned at pH=7.5 with 0.1 M $NaH_2PO_4$ buffer. The reaction mixture was applied to the cartridge and washed first with 2 ml of DMSO and then three times with 5 ml of $CH_3CN$, rinsing away all starting materials. The ammonium derivative was eluted with 5 ml of 0.03 M TFA solution in $CH_3CN:CHCl_3$ (2:1). This solution was neutralized with 300 mg of poly(4-vinylpyridine), filtered and evaporated to dryness.

The yield was 12 mg (34%) of title compound. $^1$H-NMR (DMSO-$d_6$): δ 0.88 (m, 3H), 1.28 (m, 8H), 1.60-2.19 (m, 7H), 3.00-3.41 (m, 7H), 3.83 (m, 1H), 4.88 (s, 2H), 5.99 (m, 1H), 7.01 (m, 1H), 7.21-7.39 (m, 6H), 7.49-7.52 (m, 1H); MS [M-$CF_3COO$]$^+$: 441

Also included within the scope of the present invention are pharmaceutical compositions which comprise, as the active ingredient, at least one quinuclidine derivative of general formula (I) or (II) in association with a pharmaceutically acceptable carrier or diluent. Preferably the composition is made up in a form suitable for oral administration.

The pharmaceutically acceptable carrier or diluents which are mixed with the active compound or compounds, to form the composition of this invention are well-known per se and the actual excipients used depend inter alia on the intended method of administration of the composition.

Compositions of this invention are preferably adapted for oral administration. In this case, the composition for oral administration may take the form of tablets, film-coated tablets, liquid inhalant, powder inhalant and inhalation aerosol; all containing one or more compounds of the invention; such preparations may be made by methods well-known in the art.

The diluents which may be used in the preparations of the compositions include those liquid and solid diluents which are compatible with the active ingredient, together with colouring or flavouring agents, if desired. Tablets or film-coated tablets may conveniently contain between 0.1 mg and 500 mg, preferably from 0.5 to 200 mg of active ingredient. The inhalant compositions may contain between 1 μg and 1,000 μg, preferably from 10 to 800 μg of active ingredient In human therapy, the dose of the compound of general formula (I) or (II) will depend on the desired effect and duration of treatment; adult doses are generally between 0.5 mg and 300 mg per day as tablets and 10 μg and 800 μg per day as inhalant composition.

The compounds of the present invention, or pharmaceutical compositions containing them, may be used together with a $β_2$ agonist, steroid, antiallergic drug and/or phosphodiesterase IV inhibitor, for simultaneous, separate or sequential use in the treatment of a respiratory disease.

Pharmacological Action

The following examples demonstrate the excellent pharmacological activities of the compounds of the present invention. The results on human muscarinic receptor binding and in the test on bronchospasm in guinea pig, were obtained as described below.

Human Muscarinic Receptor Studies.

The binding of [$^3$H]-NMS to human muscarinic receptors was performed according to Waelbroeck et al (1990), Mol. Pharmacol., 38: 267-273. Assays were carried out at 25° C. Membrane preparations from stably transfected Chinese hamster ovary-K1 cells (CHO) expressing the genes for the human muscarinic M3 receptors were used.

For determination of $IC_{50}$, membrane preparations were suspended in DPBS to a final concentration of 89 μg/ml for the M3 subtype. The membrane suspension was incubated with the tritiated compound for 60 min. After incubation the membrane fraction was separated by filtration and the bound radioactivity determined. Non specific binding was determined by addition of $10^{-4}$ M atropine. At least six concentrations were assayed in duplicate to generate individual displacement curves. Our results show that the compounds of the present invention have high affinities for muscarinic M3 receptors. Preferred compounds of the invention have an $IC_{50}$ (nM) value for M3 receptors of less than 35 nM, most preferably less than 10 nM.

The preferred compounds of the invention also show high selectivity for M3 receptors with respect to M2 receptors. Thus, the ratio $IC_{50}$ M2/$IC_{50}$ M3 is higher than 5, preferably higher than 10, most preferable higher than 15.

Test on Bronchospasm in Guinea Pig

The studies were performed according to H. Konzett and F. Rössler (1940), Arch. Exp. Path. Pharmacol. 195, 71-74. Aqueous solutions of the agents to be tested were nebulized and inhaled by anaesthetized ventilated male guinea pigs (Dunkin-Hartley). Bronchial response to intravenous acetylcholine challenge was determined before and after drug administration and changes in pulmonary resistance at several time-points were expressed as percent of inhibition of bronchospasm.

The compounds of the present invention showed bronchodilator activity with high potency and a long duration of action.

From the above described results one of ordinary skill in the art can readily understand that the compounds of the present invention have excellent antimuscarinic activity (M3) and thus are useful for the treatment of diseases in which the muscarinic M3 receptor is implicated, including respiratory diseases such as chronic obstructive pulmonary disease, bronchitis, asthma, bronchial hyper reactivity and rhinitis; urinary diseases such as urinary incontinence, pollakiuria, neurogenic bladder, nocturnal enuresis, unstable bladder, cystospasm and chronic cystitis; gastrointestinal diseases such as irritable bowel syndrome, spastic colitis, diverticulitis and peptic ulceration; and cardiovascular disorders such as vagally induced sinus bradicardia. For example, the compounds of the present invention are useful for the treatment of respiratory diseases such as chronic obstructive pulmonary disease, chronic bronchitis, asthma, and rhinitis; urinary diseases such as urinary incontinence and pollakinuria in neuripenia pollakinuria, neurogenic bladder, nocturnal enuresis, unstable bladder, cytospasm and chronic cystitis; and gastrointestinal diseases such as irritable bowel syndrome, spastic colitis and diverticulitis.

The present invention further provides a compound of formula (I) or (II) or a pharmaceutically acceptable composition comprising a compound of formula (I) or (II) for use in a method of treatment of the human or animal body by therapy, in particular for the treatment of respiratory, urinary or gastrointestinal disease.

The present invention further provides the use of a compound of formula (I) or (II) or a pharmaceutically acceptable composition comprising a compound of formula (I) or (I) for the manufacture of a medicament for the treatment of respiratory, urinary or gastrointestinal disease.

Further, the compounds of formula (I) or (II) and pharmaceutical compositions comprising a compound of formula (I) or (II) can be used in a method of treating respiratory, urinary or gastrointestinal disease, which method comprises administering to a human or animal patient in need of such treatment an effective amount of a compound of formula (I) or (II) or a pharmaceutical composition comprising a compound of formula (I) or (II).

Further, the compounds of formula (I) or (II) and pharmaceutical compositions comprising a compound of formula (I) or (II) can be used in combination with other drugs effective in the treatment of these diseases. For example with $\beta_2$ agonists, steroids, antiallergic drugs, phosphodiesterase IV inhibitors and/or leukotriene D4 (LTD4) inhibitors, for simultaneous, separate or sequential use in the treatment of a respiratory disease.

The present invention therefore provides a combination product comprising (i) a compound according to the invention; and
(ii) another compound effective in the treatment of a respiratory, urological or gastrointestinal disease or disorder for simultaneous, separate or sequential use.

The compound (ii) which is effective in the treatment of a respiratory, urological or gastrointestinal disease or disorder may be a $\beta_2$ agonist, steroid, antiallergic drug, phosphodiesterase IV inhibitor and/or leukotriene D4 (LTD4) antagonist Preferably, the product is for simultaneous, separate or sequential use in the treatment of a respiratory disease.

The present invention will be further illustrated by the following examples. The examples are given by way of illustration only and are not to be construed as limiting.

EXAMPLE 10

(3-Fluorobenzyl)-(3-fluorophenyl)carbamic acid (3R)-1-azabicyclo[2.2.2]oct-3-yl ester The title compound was synthesised according to method a. The yield was 3.0 g, 39.1%.

MS [M+1]$^+$: 373 $^1$H-NMR(CDCl$_3$): $\delta$ 1.20-1.35 (m, 1H), 1.35-1.50 (m, 1H), 1.5-1.60 (m, 1H), 1.60-1.75 (m, 1H), 2.0 (m, 1H), 2.55-2.85 (m, 5H), 3.18-3.27 (m, 1H), 4.79-4.90 (m, 1H), 4.90 (s, 2H), 6.85-7.10 (m, 5H), 7.22-7.35 (m, 3H).

EXAMPLE 11

(3R)-3-[(3-Fluorobenzyl)-3-fluorophenyl)carbamoyloxy]-1-(2-phenoxyethyl)-1-azoniabicyclo[2.2.2]octane bromide The title compound was synthesised according to methods a and c. The yield of the final step was 0.32 g, 69.2%.

m.p.: 142.8-143.6° C. MS [M-Br]$^+$: 493 $^1$H-NMR(DMSO-d$_6$): $\delta$ 1.50-1.70 (m, 1H), 1.70-1.85 (m, 1H), 1.85-2.05 (m, 2H), 2.23 (m, 1H), 3.25-3.40 (m, 1H), 3.40-3.75 (m, 6H), 3.95-4.10 (m, 1H), 4.44 (m, 2H), 4.90-5.10 (m, 3H), 6.90-7.25 (m, 8H), 7.25-7.45 (m, 5H).

EXAMPLE 12

(3R)-3-[(3-Fluorobenzyl)-3-fluorophenyl)carbamoyloxy]-1-(3-phenylpropyl)-1-azoniabicyclo[2.2.2] octane bromide The title compound was synthesised according to methods a and c. The yield of the final step was 0.24 g, 52.1%.

m.p.: 64.5-66.0° C. MS [M-Br]$^+$: 491 $^1$H-NMR(DMSO-d$_6$): $\delta$ 1.50-1.65 (m, 1H), 1.65-1.80 (m, 1H), 1.80-2.10 (m, 4H), 2.20 (m, 1H), 2.60 (t, 2H), 3.05-3.55 (m, 7H), 3.80-3.90 (m, 1H), 4.90-5.10 (m, 3H), 7.05-7.45 (m, 13H).

EXAMPLE 13

(3R)-1-(3-Phenylpropyl)-3-[m-tolyl-(2,4,5-trifluorobenzyl)carbamoyloxy]-1-azoniabicyclo[2.2.2]octane bromide The title compound was synthesised according to methods a and c. The yield of the final step was 0.32 g, 72.5%.

m.p.: 113.1-114.8° C. MS [M-Br]$^+$: 523 $^1$H-NMR(DMSO-d$_6$): $\delta$ 1.40-1.60 (m, 1H), 1.60-1.80 (m, 1H), 1.80-2.10 (m, 4H), 2.18 (m, 1H), 2.26 (s, 3H), 2.60 (t, 2H), 3.05-3.55 (m, 7H), 3.80-3.90 (m, 1H), 4.90 (m, 2H), 4.98 (m, 1H), 7.0-7.15 (m, 2H), 7.15-7.40 (m, 7H), 7.40-7.60 (m, 2H).

EXAMPLE 14

(3-Fluorophenyl)-(3,4,5-trifluorobenzyl)carbamic acid (3R)-1-azabicyclo[2.2.2]oct-3-yl ester The title compound was synthesised according to method a. The yield was 0.33 g, 8.8%.

MS [M+1]$^+$: 409 $^1$H-NMR(CDCl$_3$): $\delta$1.20-1.80 (m, 4H), 2.02 (m, 1H), 2.60-3.05 (m, 5H), 3.25-3.40 (m, 1H), 4.70-4.82 (m, 2H), 4.85-4.90 (m, 1H), 6.80-7.10 (m, 4H), 7.20-7.40 (m, 2H).

EXAMPLE 15

(3R)-3-[(3-Fluorophenyl)-(3,4,5-trifluorobenzyl) carbamoyloxy]-1-(2-phenoxyethyl)-1-azoniabicyclo [2.2.2]octane bromide The title compound was synthesised according to methods a and c. The yield of the final step was 0.16 g, 75%.

m.p.: 173.9-175.5° C. MS [M-Br]$^+$: 529 $^1$H-NMR(DMSO-d$_6$): $\delta$ 1.50-2.05 (m, 4H), 2.24 (m, 1H), 3.25-3.85 (m, 7H), 4.03 (m, 1H), 4.45 (m, 2H), 4.95 (m, 2H), 5.04 (m, 1H), 6.95-7.15 (m, 4H), 7.20-7.45 (m, 7H).

EXAMPLE 16

Cyclohexylmethyl-(2-fluorophenyl)carbamic acid (3R)-1-azabicyclo[2.2.2]oct-3-yl ester The title compound was synthesised according to method a. The yield was 3.15 g, 42.3%.

MS [M+1]$^+$: 361 $^1$H-NMR(CDCl$_3$): $\delta$ 0.80-1.05 (m, 2H), 1.05-1.80 (m, 13H), 2.0 (m, 1H), 2.55-3.05 (m, 5H), 3.15-3.30 (m, 1H), 3.40-3.60 (m, 2H), 4.70-4.85 (m, 1H), 7.05-7.35 (m, 4H).

EXAMPLE 17

(3R)-3-[Cyclohexylmethyl-(2-fluorophenyl)carbamoyloxy]-1-(2-phenoxyethyl)-1-azoniabicyclo[2.2.2]octane bromide The title compound was synthesised according to methods a and c. The yield of the final step was 0.38 g, 81.4%.

m.p.: 73.1-74.5° C. MS [M-Br]$^+$: 481 $^1$H-NMR(DMSO-$d_6$): δ 0.80-1.0 (m, 2H), 1.0-1.20 (m, 3H), 1.20-1.45 (m, 1H), 1.45-1.80 (m, 6H), 1.80-2.20 (m, 4H), 3.05-3.20 (m, 1H), 3.30-3.85 (m, 8H), 3.90-4.10 (m, 1H), 4.35-4.50 (m, 2H), 4.90-5.10 (m, 1H), 6.95-7.10 (m, 3H), 7.20-7.55 (m, 6H).

EXAMPLE 18

(3R)-3-[Cyclohexylmethyl-(2-fluorophenyl)carbamoyloxy]-1-(3-phenylpropyl)-1-azoniabicyclo[2.2.2]octane bromide The title compound was synthesised according to methods a and c. The yield of the final step was 0.34 g, 73%.

m.p.: 73.3-74.1° C. MS [M-Br]$^+$: 479 $^1$H-NMR(DMSO-$d_6$): δ 0.80-1.45 (m, 6H), 1.50-2.20 (m, 12H), 2.57 (m, 2H), 2.90-3.0 (m, 1H), 3.10-3.65 (m, 8H), 3.75-3.95 (m, 1H), 4.90-5.05 (m, 1H); 7.20-7.55 (m, 9H).

EXAMPLE 19

[2-(3,4-Dimethoxyphenyl)ethyl]-(5-methylfuran-2-ylmethyl)carbamic acid (3R)-1-azabicyclo[2.2.2]oct-3-yl ester The title compound was synthesised according to method a. The yield was 3.5 g, 61.2%.

MS [M+1]$^+$: 429 $^1$H-NMR(CDCl$_3$): δ 1.34-1.50 (m, 1H), 1.50-1.64 (m, 1H), 1.64-1.78 (m, 1H), 1.78-1.94 (m, 1H), 2.05 (m, 1H), 2.27 (two singlets, 3H), 2.64-2.84 (m, 5H), 2.84-2.98 (m, 2H), 3.20-3.30 (m, 1H), 3.35-3.60 (m, 2H), 3.82 (s, 6H), 4.28 (m, 1H), 4.36 (m, 1H), 4.76 (m, 1H), 5.89 (m, 1H), 6.03-6.13 (m, 1H), 6.60-6.82 (m, 3H).

EXAMPLE 20

(3R)-3-[[2-(3,4-Dimethoxyphenyl)ethyl]-(5-methylfuran-2-ylmethyl)carbamoyloxy]-1-(4-ethoxycarbonylbutyl)-1-azoniabicyclo[2.2.2]octane formate The title compound was synthesised according to methods a and c. The alkylating agent used in method c was ethyl 5-bromopentanoate.

A portion of 270 mg of the obtained product was purified by preparative HPLC/MS to give 53 mg of the pure product as a formate.

MS [M-HCOO]$^+$: 557 $^1$H-NMR (DMSO-$d_6$): δ 1.16-1.23 (m, 3H), 1.45-1.75 (m, 4H), 1.75-2.10 (m, 4H), 2.14-2.28 (m, 1H), 2.24 (s, 3H); 2.38 (m, 2H), 2.68 (m, 2H), 3.0-3.90 (m, 10H), 3.71 and 3.73 (two singlets, 6H), 4.03-4.10 (m, 2H), 4.31-4.48 (m, 2H), 4.80-5.0 (m, 1H), 6.03 (m, 1H); 6.27 (m, 1H), 6.64-6.88 (m, 3H), 8.34 (s, 1H). Conditions used in the purification HPLC-MS: Column: Symmetry C18, 100 A, 5 μm 19×100 mm, Waters. Mobile phase: A (H$_2$O 0.1% HCOONH$_4$, pH=3) and B (AcN 0.1% HCOONH$_4$, pH=3), B: 19%→34%.

EXAMPLE 21

(5-Bromothiophen-2-ylmethyl)-(2,4,5-trifluorophenyl)carbainic acid (3R)-1-azabicyclo[2.2.2]oct-3-yl ester The title compound was synthesised according to method a.

A portion of 158 mg of the obtained product was purified by preparative HPLC/MS to give 16 mg of pure product as a formate.

MS [M+1]$^+$: 475, 477 Conditions used in the purification HPLC-MS: Column: Symmetry C18, 100 A, 5 μm 19×100 mm, Waters. Mobile phase: A (H$_2$O 0.1% HCOONH$_4$, pH=3) and B (AcN 0.1% HCOONH$_4$, pH=3), B: 10%→35%.

EXAMPLE 22

(4-Fluoro-2-methylphenyl)-(3-methylthiophen-2-ylmethyl)carbamic acid (3R)-1-azabicyclo[2.2.2]oct-3-yl ester The title compound was synthesised according to method a. The yield of the final step was 0.8 g, 10.8%.

MS [M+1]$^+$: 389 $^1$H-NMR (CDCl$_3$): δ 1.10-1.25 (m, 2H), 1.45-1.70 (m, 2H), 1.70-1.85 (m, 1H), 1.87 (s, 3H), 2.0-2.05 (two singlets, 3H), 2.40-3.0 (m, 5H), 3.10-3.40 (m, 1H), 4.65-5.0 (m, 3H), 6.72 (m, 1H), 6.80-6.95 (m, 3H), 7.12 (m, 1H).

EXAMPLE 23

(3R)-3-[(4-Fluoro-2-methylphenyl)-(3-methylthiophen-2-ylmethyl)carbamoyloxy]-1-(2-phenoxyethyl)-1-azoniabicyclo[2.2.2]octane bromide The title compound was synthesised according to methods a and c. The yield of the final step was 0.5 g, 84.7%.

MS [M-Br]$^+$: 509 $^1$H-NMR(DMSO-$d_6$): δ 1.15-1.45 (m, 1H), 1.60-2.20 (m, 10H), 2.90-3.10 (m, 1H), 3.30-3.85 (m, 6H), 3.90-4.20 (m, 1H), 4.30-4.55 (m, 2H), 4.75-5.15 (m, 3H), 6.78 (m, 1H), 6.90-7.20 (m, 6H), 7.35 (m, 3H).

EXAMPLE 24

(3-Fluoro-4-methoxyphenyl)thiophen-3-ylmethylcarbamic acid (3R)-1-azabicyclo[2.2.2]oct-3-yl ester The title compound was synthesised according to method a The yield of the final step was 1.9 g, 25.7%.

MS [M+1]$^+$: 391 $^1$H-NMR (CDCl$_3$): δ 1.20-1.90 (m, 4H), 2.01 (m, 1H), 2.55-2.90 (m, 5H), 3.22 (m, 1H), 3.88 (s, 3H), 4.70-4.90 (m, 3H), 6.70-6.95 (m, 3H), 6.95-7.15 (m, 2H), 7.26 (m, 1H).

EXAMPLE 25

(3R)-3-[(3-Fluoro-4-methoxyphenyl)thiophen-3-ylmethylcarbamoyloxy]-1-(3-phenylallyl)-1-azoniabicyclo[2.2.2]octane bromide The title compound was synthesised according to methods a and c. The yield of the final step was 1.9 g, 97.1%

MS [M-Br]$^+$: 507 $^1$H-NMR(DMSO-$d_6$): δ 1.40-1.65 (m, 1H), 1.65-2.05 (m, 3H), 2.10-2.30 (m, 1H), 3.10-3.30 (m, 1H), 3.30-3.60 (m, 4H), 3.78 (s, 3H), 3.80-3.95 (m, 1H), 3.95-4.10 (m, 2H), 4.80 (m, 2H), 5.0 (m, 1H), 6.42 (m, 1H), 6.85 (m, 1H), 6.90-7.15 (m, 3H), 7.20-7.50 (m, 7H), 7.58 (m, 1H).

EXAMPLE 26

(4,5-Dimethylfuran-2-ylmethyl)-(5-methylfuran-2-ylmethyl)carbamic acid (3R)-1-azabicyclo[2.2.2]oct-3-yl ester The title compound was synthesised according to method a. 200 mg of the obtained product were purified by column chromatography (silica gel, $CHCl_3$/EtOH 5:1 as eluent) to obtain 34 mg of a pure sample.

MS $[M+1]^+$: 373 $^1$H-NMR ($CDCl_3$): δ 1.20-1.40 (m, 1H), 1.40-1.55 (m, 1H), 1.55-1.70 (m, 1H), 1.70-1.80 (m, 1H), 1.85-2.05 (m, 1H), 1.90 (s, 3H), 2.16 (s, 3H), 2.25 (s, 3H), 2.70-3.05 (m, 5H), 3.25-3.32 (m, 1H), 4.20-4.50 (m, 4H), 4.85 (m, 1H), 5.85-6.15 (m, 3H).

EXAMPLE 27

(3R)-1-Allyl-3-[2-(4-fluorophenyl)ethyl]-(3-methylthiophen-2-ylmethyl)carbamoyloxy]-1-azoniabicyclo[2.2.2]octane bromide The title compound was synthesised according to methods a and c. The yield of the final step was 0.4 g, 51.3%.

MS $[M-Br]^+$: 443 $^1$H-NMR(DMSO-$d_6$) δ 1.80-2.10 (m, 4H), 2.20 (s, 3H), 2.25-2.30 (m, 1H), 2.77 (m, 2H), 3.15-3.70 (m, 7H), 3.82 (m, 1H), 3.90 (m, 2H), 4.45-4.65 (m, 2H), 4.85-5.05 (m, 1H), 5.56-5.66 (m, 2H), 5.90-6.10 (m, 1H), 6.87 (m, 1H), 7.10-7.30 (m, 4H), 7.36 (m, 1H).

EXAMPLE 28

Benzylphenylcarbamic acid 1-azabicyclo[2.2.2]oct-3-(R)yl ester

The title compound was synthesised according to method a. The yield of the final step was 1000 mg, 18%. $^1$H-NMR ($CDCl_3$): δ 1.3-1.7 (m, 4H), 1.9 (s, 1H), 2.5-2.8 (m, 5H), 3.2 (m, 1H), 4.8 (m, 1H), 4.9 (s, 2H), 7.1-7.4 (m, 10H); MS $[M+1]^+$: 337.

EXAMPLE 29

3-(R)(Benzylphenylcarbamoyloxy)-1-methyl-1-azoniabicyclo[2.2.2]octane, trifluoroacetate The title compound was synthesised according to method d. The yield of the final step was 20 mg, 34%. $^1$H-NMR (DMSO-$d_6$): δ 1.54-1.90 (m, 4H), 2.17 (s, 1H), 2.95 (s, 3H), 3.22-3.52 (m, 5H), 3.84 (m, 1H), 4.92 (s, 2H), 4.99 (m, 1H), 7.12-7.37 (m, 10H); MS $[M-CF_3COO]^+$: 351.

EXAMPLE 30

3-(R)(Benzylphenylcarbamoyloxy)-1-(4-methylpent-3-enyl)-1-azoniabicyclo[2.2.2]octane, trifluoroacetate The title compound was synthesised according to method d. The yield of the final step was 18 mg, 25%. MS $[M-CF_3COO]^+$: 419.

EXAMPLE 31

3-(R)(Benzylphenylcarbamoyloxy)-1-(3-phenoxypropyl)-1-azoniabicyclo[2.2.2]octane; trifluoroacetate The title compound was synthesised according to method d. The yield of the final step was 21 mg, 26%. $^1$H-NMR (DMSO-$d_6$): δ 1.56-1.91 (m, 4H), 2.11-2.20 (m, 3H), 3.12 (m, 1H), 3.34-3.51 (m, 6H), 3.86 (m, 1H), 4.06 (m, 2H), 4.93 (s, 2H), 5.02 (m, 1H), 6.97 (m, 3H), 7.20-7.38 (m, 12H); MS $[M-CF_3COO]^+$: 471.

EXAMPLE 32

3-(R)(Benzylphenylcarbamoyloxy)-1-(3-phenylallyl)-1-azoniabicyclo[2.2.2]octane; bromide The title compound was synthesised according to method c. The yield of the final step was 220 mg, 70%. $^1$H-NMR (DMSO-$d_6$): δ 1.55-1.92 (m, 4H), 2.21 (s, 1H), 3.15 (m, 1H), 3.34-3.50 (m, 5H), 3.90 (m, 1H), 4.1 (m, 2 H), 4.02 (s, 2 H), 5.05 (m, 1H), 6.49 (m, 1H), 6.85-6.90 (d, 1H), 7.20-7.59 (m, 12H), 7.59-7.61 (m, 2H); MS $[M-Br]^+$: 453; mp: 129° C.

EXAMPLE 33

1-Allyl-3-(R)(benzylphenylcarbamoyloxy)-1-azoniabicyclo[2.2.2]octane; bromide

The title compound was synthesised according to method c. The yield of the final step was 230 mg, 85%. $^1$H-NMR (DMSO-$d_6$): δ 1.58-1.91 (m, 4H), 2.20 (s, 1H), 3.10 (m, 1H), 3.27-3.41 (m, 4H), 3.79-3.90 (m, 3H), 4.92 (s, 2H), 5.03 (m, 1H), 5.61 (m, 2H), 5.98 (m, 1H), 7.20-7.38 (m, 10H); MS $[M-Br]^+$: 377; mp: 70° C.

EXAMPLE 34

3-(R)(Benzylphenylcarbamoyloxy)-1-(2-hydroxyethyl)-1-azoniabicyclo[2.2.2]octane; trifluoroacetate The title compound was synthesised according to method d. The yield of the final step was 12 mg, 19%. MS $[M-CF_3COO]^+$: 381.

EXAMPLE 35

3-(R)(Benzylphenylcarbamoyloxy)-1-isopropyl-1-azoniabicyclo[222]octane; trifluoroacetate The title compound was synthesised according to method d. The yield of the final step was 17 mg, 26%. $^1$H-NMR (DMSO-$d_6$): δ 1.24 (m, 6H), 1.64-1.89 (m, 4H), 2.20 (s,1H), 2.78 (m,1H), 3.23-3.32 (m,4 H), 3.50 (m, 1H), 3.76 (m, 1H), 4.92 (s, 2H), 5.06 (m, 1H), 7.20-7.38 (m, 10H); MS $[M-CF_3COO]^+$: 379.

EXAMPLE 36

3-(R)(Benzylphenylcarbamoyloxy)-1-propyl-1-azoniabicyclo[2.2.2]octane; trifluoroacetate The title compound was synthesised according to method d. The yield of the final step was 16 mg, 25%. $^1$H-NMR (DMSO-$d_6$): δ 0.88 (m, 3H), 1.57-1.68 (m, 4H), 1.89 (m, 2H), 2.18 (s, 1H), 2.99-3.14 (m, 3H), 3.26-3.40 (m, 4H), 3.83 (m, 1H), 4.92 (s, 2H), 5.01 (m, 1H), 7.20-7.37 (m, 10H); MS $[M-CF_3COO]^+$: 379.

EXAMPLE 37

3-(R)(Benzylphenylcarbamoyloxy)-1-(3-cyanopropyl)-1-azoniabicyclo[2.2.2]octane; trifluoroacetate The title compound was synthesised according to method d: The yield of the final step was 13 mg, 19%. $^1$H-NMR (DMSO-$d_6$): δ 1.67-2.07 (m, 6H), 2.19 (s, 1H), 2.60 (m,2H), 3.07 (m, 1H), 3.21-3.48 (m, 6H), 3.85 (m,1H), 4.92 (s, 2H), 5.01 (m, 1H), 7.20-7.37 (m, 10); MS [M-CF$_3$COO]$^+$: 404.

EXAMPLE 38

3-(R)(Benzylphenylcarbamoyloxy)-1-cyclopropylmethyl-1-azoniabicyclo[2.2.2]octane; trifluoroacetate The title compound was synthesised according to method d. The yield of the final step was 9 mg, 14%. MS [M-CF$_3$COO]$^+$: 391.

EXAMPLE 39

3-(R)(Benzylphenylcarbamoyloxy)-1-(2-ethoxyethyl)-1-azoniabicyclo[2.2.2]octane; trifluoroacetate The title compound was synthesised according to method d. The yield of the final step was 22 mg, 32%. $^1$H-NMR (DMSO-$d_6$): δ 1.12 (m, 3H): 1.58-1.90 (m, 4H), 2.19 (s, 1H), 3.12-3.15 (m, 1H), 3.28-3.53 (m, 8H), 3.75 (m, 2H), 3.90 (m, 1H), 4.91 (s, 2H), 5.02 (m, 1H), 7.20-7.37 (m, 10H); MS [M-CF$_3$COO]$^+$: 409.

EXAMPLE 40

3-(R)(Benzylphenylcarbamoyloxy)-1-(4-ethoxycarbonylbutyl)-1-azoniabicyclo[2.2.2]octane; trifluoroacetate The title compound was synthesised according to method d. The yield of the final step was 14 mg, 18%. $^1$H-NMR (DMSO-$d_6$): δ 1.19 (m, 3H), 1.50-1.67 (m, 4H), 1.85-1.88 (m, 2H), 2.18 (s,1H), 2.38 (m, 2H), 3.99 (m, 1H), 3.16-3.42 (m, 8H), 3.82 (m, 1H), 4.06 (m, 2H), 4.92 (s, 2H), 5.02 (m, 1H), 7.19-7.37 (m, 10H); MS [M-CF$_3$COO]$^+$: 465.

EXAMPLE 41

3-(R)(Benzylphenylcarbamoyloxy)-1-(4-phenylbutyl)-1-azoniabicyclo[2.2.2]octane; trifluoroacetate The title compound was synthesised according to method d. The yield of the final step was 14 mg, 18%. $^1$H-NMR (DMSO-$d_6$): δ 1.57-1.65 (m, 6H), 1.88 (m, 2H), 2.18 (s, 1H), 2.63 (m, 2H), 3.00 (m, 1H), 3.18-3.42 (m, 6H), 3.79-3.86 (m, 1H), 4.94 (s, 2H), 5.00 (m, 1H), 7.18-7.37 (m, 15H); MS [M-CF$_3$COO]$^+$: 469.

EXAMPLE 42

3-(R)(Benzylphenylcarbamoyloxy)-1-[3-(4-fluorophenoxy)propyl]-1-azoniabicyclo[2.2.2]octane; trifluoroacetate The title compound was synthesised according to method d. The yield of the final step was 21 mg, 25%. $^1$H-NMR (DMSO-$d_6$): δ 1.55-1.91 (m, 4H), 2.10-2.20 (m,3H), 3.10 (m, 1H), 3.28-3.50 (m, 6H), 3.88 (m, 1H), 4.02 (m, 2H), 4.93 (s, 2H), 5.02 (m, 1H), 6.95-7.12 (m, 2H), 7.12-7.38 (m,12H); MS [M-CF$_3$COO]$^+$: 489.

EXAMPLE 43

3-(R)(Benzylphenylcarbamoyloxy)-1-(3-hydroxypropyl)-1-azoniabicyclo[2.2.2]octane; trifluoroacetate The title compound was synthesised according to method d. The yield of the final step was 12 mg, 18%. $^1$H-NMR (DMSO-$d_6$): δ 1.54-1.88 (m, 6H), 2.18 (s, 1H), 3.09 (m, 1H), 3.23-3.49 (m, 8H), 3.85 (m, 1H), 4.84 (m,OH), 4.92 (s, 2H), 5.02 (m, 1H), 7.19-7.37 (m, 10H); MS [M-CF$_3$COO]$^+$: 395.

EXAMPLE 44

1-(4-Acetoxybutyl)-3-(R)(benzylphenylcarbamoyloxy)-1-azoniabicyclo[2.2.2]octane; trifluoroacetate The title compound was synthesised according to method d. The yield of the final step was 9 mg, 12%. $^1$H-NMR (DMSO-$d_6$): δ 1.40-1.70 (m, 5H), 1.81-1.91 (m, 3H), 2.02 (m, 3H), 2.19 (s, 1H), 3.03 (m, 1H), 3.19 (m, 2H), 3.26-3.46 (m, 4H), 3.80-3.84 (m, 1H), 4.04 (m, 2H), 4.92 (s, 2H), 5.01-5.02 (m, 1H), 7.19-7.37 (m, 10H); MS [M-CF$_3$COO]$^+$: 451.

EXAMPLE 45

3-(R)(Benzylphenylcarbamoyloxy)-1-(4-oxo-4-thiophen-2-ylbutyl)-1-azoniabicyclo[2.2.2]octane; trifluoroacetate The title compound was synthesised according to method d. The yield of the final step was 16 mg, 19%. $^1$H-NMR (DMSO-$d_6$): δ 1.55-1.69 (m, 2H), 1.87-2.05 (m, 4H), 2.19 (s, 1H), 3.09 (m, 3H), 3.22 (m, 2H), 3.29-3.46 (m, 4H), 3.88 (m, 1H), 4.93 (s, 2H), 5.02 (m, 1H), 7.19-7.38 (m, 11H), 7.98-8.06 (m, 2H); MS [M-CF$_3$COO]$^+$: 489.

EXAMPLE 46

3-(R)(Benzylphenylcarbamoyloxy)-1-[3-(3-hydroxyphenoxy)propyl]-1-azoniabicyclo[2.2.2]octane; trifluoroacetate The title compound was synthesised according to method d. The yield of the final step was 17 mg, 21%. $^1$H-NMR (DMSO-$d_6$): δ 1.57-1.68 (m, 2H), 1.90 (m, 2H), 2.08-2.19 (m, 3H), 3.11 (m, 1H), 3.28-3.50 (m, 6H), 3.88 (m, 1H), 3.97 (m, 2H), 4.93 (s, 2H), 5.02 (m, 1H), 6.33-6.40 (m, 3H), 7.04 (m, 1H), 7.20-7.38 (m, 10H), 9.5 (s, OH); MS [M-CF$_3$COO]$^+$: 487.

EXAMPLE 47

3-(R)(Benzylphenylcarbamoyloxy)-1-heptyl-1-azoniabicyclo[2.2.2]octane; trifluoroacetate The title compound was synthesised according to method d. The yield of the final step was 17 mg, 23%. $^1$H-NMR (DMSO-$d_6$): δ 0.88 (m, 3H), 1.28 (m, 8H), 1.62 (m, 4H), 1.85-1.88 (m, 2H), 2.18 (s, 1H), 3.02 (m, 1H), 3.15 (m, 2H), 3.26-3.40 (m, 4H), 3.83 (m, 1H), 4.92 (s, 2H), 5.01 (m, 1H), 7.20-7.37 (m, 10H); MS [M-CF$_3$COO]$^+$: 435.

EXAMPLE 48

1-(2-Benzyloxyethyl)-3-(R)(benzylphenylcarbamoyloxy)-1-azoniabicyclo[2.2.2]octane; trifluoroacetate The title compound was synthesised according to method d. The yield of the final step was 20 mg, 25%. $^1$H-NMR (DMSO-$d_6$): δ 1.54-1.94 (m, 4H), 2.20 (s, 1H), 3.17 (m, 1H), 3.28-3.55 (m, 6H), 3.85 (m, 2H), 9.92-3.99 (m, 1H), 4.53 (s, 2H), 4.91 (s, 2H), 5.02 (m, 1H), 7.18-7.40 (m, 15H); MS [M-CF$_3$COO]$^+$: 471.

EXAMPLE 49

Benzyl-(4-fluorophenyl)carbamic acid 1-azabicyclo[2.2.2]oct-3(R)yl ester

The title compound was synthesised according to method a. The yield of the final step was 1110 mg, 13%. $^1$H-NMR (DMSO-$d_6$): δ 1.16-1.52 (m, 4H), 1.81 (s, 1H), 2.42-2.57 (m, 5H), 2.99-3.07 (m, 1H), 4.63 (m, 1H), 4.84 (s, 2H), 7.10-7.32 (m, 9H); MS [M+1]: 355.

EXAMPLE 50

1-Allyl-3-(R)[benzyl-(4-fluorophenyl)carbamoyloxy]-1-azoniabicyclo[2.2.2]octane; trifluoroacetate The title compound was synthesised according to method d. The yield of the final step was 10mg, 23%. MS [MC-F$_3$COO]$^+$: 395.

EXAMPLE 51

3-(R)[Benzyl-(4-fluorophenyl)carbamoyloxy]-1-(3-phenylpropyl)-1azoniabicyclo[2.2.2]octane; trifluoroacetate The title compound was synthesised according to method d. The yield of the final step was 13 mg, 25%. MS [MC-F$_3$COO]$^+$: 473.

EXAMPLE 52

Benzyl-p-tolylcarbamic acid 1-azabicyclo[2.2.2]oct-3-(R)yl ester

The title compound was synthesised according to method a. The yield of the final step was 1070 mg, 11%. $^1$H-NMR (DMSO-$d_6$): δ 1.18-1.30 (m, 2H), 1.45-1.55 (m, 2H), 1.83 (s, 1H), 2.25 (s, 3H), 2.43-2.59 (m,5H), 3.01-3.10 (m, 1H), 4.64 (m, 1H), 4.85 (s, 2H), 7.12-7.34 (m, 9H); MS [M+1]$^+$: 351.

EXAMPLE 53

1-Allyl-3-(R)(benzyl-p-tolyl-carbamoyloxy)-1-azoniabicyclo[2.2.2]octane; trifluoroacetate The title compound was synthesised according to method d. The yield of the final step was 9 mg, 19%. MS [M-CF$_3$COO]$^+$: 391.

EXAMPLE 54

3-R)(Benzyl-p-tolylcarbamoyloxy)-1-(3-phenylpropyl)-1-azoniabicyclo[2.2.2]octane; trifluoroacetate The title compound was synthesised according to method d. The yield of the final step was 13 mg, 25%. MS [M-CF$_3$COO]$^+$: 469.

EXAMPLE 55

3-(R)(Benzylphenylcarbamoyloxy)-1-[2-2-methoxyethoxy)ethyl]-1-azoniabicyclo[2.2.2]octane; bromide The title compound was synthesised according to method c. The yield of the final step was 390 mg, 84%. $^1$H-NMR (DMSO-$d_6$): δ 1.55-1.75 (m, 2 H), 1.88 (m, 2H), 2.17 (s, 1H), 3.14 (m, 1H), 3.22 (s, 3H), 3.29-3.55 (m, 10H), 3.78 (m, 2H), 3.90 (m, 1H), 4.89 (s, 2H), 4.99 (m, 1H), 7.17-7.35 (m, 10H); MS [M-Br]$^+$: 439.

EXAMPLE 56

3-(R)(Benzylphenylcarbamoyloxy)-1-phenethyl-1-azoniabicyclo[2.2.2octane; bromide The title compound was synthesised according to method c. The yield of the final step was 200 mg, 65%. $^1$H-NMR (DMSO-$d_6$): δ 1.55-1.75 (m, 2H), 1.90 (m, 2H), 2.19 (s, 1H), 3.00 (m, 2H), 3.10 (m, 1H), 3.31-3.51 (m, 6H), 3.90 (m, 1H), 4.91 (s, 2H), 5.04 (m, 1H), 7.18-7.37 (m, 15H). MS [M-Br]$^+$: 441; mp 81° C.

EXAMPLE 57

3-(R)(Benzylphenylcarbamoyloxy)-1-(3-thiophen-2-ylpropyl)-1-azoniabicyclo[2.2.2]octane; bromide The title compound was synthesised according to method c. The yield of the final step was 970 mg, 82%. $^1$H-NMR (DMSO-$d_6$): δ 1.55-1.69 (m, 2H), 1.85-2.04 (m, 4H), 2.18 (s, 1H), 2.83 (m, 2H), 3.01 (m, 1H), 3.20-3.44 (m, 6H), 3.85 (m, 1 H), 4.92 (s, 2H), 5.00 (m, 1H), 6.94-7.00 (m, 2 H), 7.19-7.40 (m, 11H). MS [M-Br]$^+$: 461; mp 95° C.

EXAMPLE 58

3-(R)(Benzylphenylcarbamoyloxy)-1-(3-phenylpropyl)-1-azoniabicyclo[2.2.2]octane; bromide The title compound was synthesised according to method c. The yield of the final step was 880 mg, 79%. $^1$ H-NMR (DMSO-$d_6$): δ 1.55-1.69 (m, 2H), 1.85-2.00 (m, 4H), 2.18 (s, 1H), 2.59 (m, 2H), 3.04 (m, 1H), 3.23-3.44 (m, 6H), 3.85 (m, 1H), 4.92 (s, 2H), 5.02 (m, 1H), 7.18-7.36 (m, 15H). ); MS [M-Br]$^+$: 455; mp 101° C.

EXAMPLE 59

3-(R)(Benzylphenylcarbamoyloxy)-1-(2-phenoxyethyl)-1-azoniabicyclo[2.2.2]octane; bromide The title compound was synthesised according to method c. The yield of the final step was 360 mg, 67%. $^1$H-NMR (DMSO-$d_6$): δ 1.5-1.73 (m, 2H), 1.89 (m, 2H), 2.20 (s, 1H), 3.23 (m, 1H), 3.46-3.72 (m, 6H), 4.02 (m, 1H), 4.43 (m, 2H), 4.92 (s, 2H), 5.03 (m, 1H), 7.01 (m, 3H), 7.17-7.38 (m, 12H); MS [M-Br]$^+$: 457; mp 117° C.

EXAMPLE 60

3-(R)(Benzylphenylcarbamoyloxy)-1-[3-(3-cyanophenoxy)propyl]-1-azoniabicyclo[2.2.2]octane; trifluoroacetate The title compound was synthesised according to method d. The yield of the final step was 16 mg, 36%; MS [M-CF$_3$COO]$^+$: 496.

EXAMPLE 61

3-(R)(Benzylphenylcarbamoyloxy)-1-[3-(naphthalen-1-yloxy)propyl]-1-azoniabicyclo[2.2.2]octane; trifluoroacetate The title compound was synthesised according to method d. The yield of the final step was 10 mg, 21%; MS [M-CF$_3$COO]$^+$: 521.

EXAMPLE 62

3-(R)(Benzylphenylcarbamoyloxy)-1-[3-(methylphenylamino)propyl]-1azoniabicyclo[2.2.2]octane; trifluoroacetate The title compound was synthesised according to method d. The yield of the final step was 12 mg, 28%; MS [M-CF$_3$COO]$^+$: 484.

EXAMPLE 63

3-(R)(Benzylphenylcarbamoyloxy)-1-(3-phenylsulfanylpropyl)-1-azoniabicyclo[2.2.2]octane; trifluoroacetate The title compound was synthesised according to method d. The yield of the final step was 8 mg, 18%; $^1$H-NMR (DMSO-d$_6$): δ 1.45-2.00 (m, 6H), 2.17 (bs, 1H), 3.00 (m, 2H), 3.28-3.41 (m, 7H), 3.83 (m, 1H), 4.91 (s, 2H), 4.98 (m, 1H), 7.18-7.41 (m, 15H); MS [M-CF$_3$COO]$^+$: 487.

EXAMPLE 64

3-(R)(Benzylphenylcarbamoyloxy)-1-(4-oxo-4-phenylbutyl)-1-azoniabicyclo[2.2.2]octane; trifluoroacetate The title compound was synthesised according to method d. The yield of the final step was 10 mg, 23%; $^1$H-NMR (DMSO-d$_6$): δ 1.50-2.06 (m, 6H), 2.20 (bs, 1H), 3.13-3.47 (m, 9H), 3.89 (m, 1H), 4.93 (s, 2H), 5.02 (m, 1H), 7.19-7.38 (m, 10H), 7.54-7.70 (m, 3H), 7.98-8.00 (m, 2H); MS [M-CF$_3$COO]$^+$: 483.

EXAMPLE 65

3-(R)(Benzylphenylcarbamoyloxy)-1-[3-(2,4,6-trimethylphenoxy)propyl]-1azoniabicyclo[2.2.2]octane; trifluoroacetate The title compound was synthesised according to method d. The yield of the final step was 14 mg, 30%; $^1$H-NMR (DMSO-d$_6$): δ 1.50-2.20 (m, 7H), 2.19 (s, 9H), 3.16-3.52 (m, 7H), 3.73 (m, 2H), 3.92 (m, 1H), 4.93 (s, 2H), 5.03 (m, 1H), 6.83 (s, 2H), 7.19-7.38 (m, 10H); MS [(M-CF$_3$COO]$^+$: 513.

EXAMPLE 66

3-(R)(Benzylphenylcarbamoyloxy)-1-[3-(2-chlorophenoxy)propyl]-1-azoniabicyclo[2.2.2]octane; trifluoroacetate The title compound was synthesised according to method d. The yield of the final step was 14 mg, 31%; MS [M-CF$_3$COO]$^+$: 506.

EXAMPLE 67

3-(R)(Benzylphenylcarbamoyloxy)-1-[3-(3-trifluoromethylphenoxy)propyl]-1-azoniabicyclo[2.2.2] octane; trifluoroacetate The title compound was synthesised according to method d. The yield of the final step was 14 mg, 29%; $^1$H-NMR (DMSO-d$_6$): δ 1.50-2.00 (m, 4H), 2.08-2.20 (m, 3H), 3.12-3.50 (m, 7H), 3.90 (m, 1H), 4.14 (m, 2H), 4.93 (s, 2H), 5.03 (m, 1H), 7.19-7.38 (m, 13H), 7.54-7.59 (m, 1H). MS [M-CF$_3$COO]$^+$: 539.

EXAMPLE 68

3-(R)(Benzylphenylcarbamoyloxy)-1-[3-(biphenyl-4-yloxy)propyl]-1-azoniabicyclo[2.2.2]octane; trifluoroacetate The title compound was synthesised according to method d. The yield of the final step was 12 mg, 24%; $^1$H-NMR (DMSO-d$_6$): δ 1.50-2.20 (m, 7H), 3.14 (bs, 1H), 3.28-3.52 (m, 6H), 3.91 (m, 1H), 4.10 (m, 2H), 4.93 (s, 2H), 5.03 (m, 1H), 7.03-7.08 (m, 2H), 7.18-7.47 (m, 13H), 7.61-7.65 (m, 4H); MS [M-CF$_3$COO]$^+$: 547.

EXAMPLE 69

3-(R)(Benzylphenylcarbamoyloxy)-1-[3-(2,4difluorophenoxy)propyl]-1-azoniabicyclo[2.2.2]octane; trifluoroacetate The title compound was synthesised according to method d. The yield of the final step was 10 mg, 22%; $^1$H-NMR (DMSO-d$_6$): δ 1.5-2.19 (m, 7H), 3.10 (bs, 1H), 3.28-3.51 (m,6H), 3.90 (m, 1H), 4.10 (m, 2H), 4.93 (s, 2H), 5.02 (m, 1H), 7.02-7.09 (m, 1H), 7.19-7.37 (m, 12H); MS [M-CF$_3$COO]$^+$: 507.

EXAMPLE 70

3-(R)(Benzylphenylcarbamoyloxy)-1-[3-(4-methoxyphenoxy)propyl]-1-azoniabicyclo[2.2.2]octane; trifluoroacetate The title compound was synthesised according to method d. The yield of the final step was 10 mg, 22%; $^1$H-NMR (DMSO-d$_6$): 1.50-2.19 (m, 7H), 3.11 (bs, 1H), 3.28-3.51 (m, 6H), 3.70 (s,3H), 3.89 (m, 1H), 3.94-3.99 (m, 2H), 4.93 (s, 2H), 5.02 (m, 1H), 6.85-6.92 (m, 4H), 7.19-7.38 (m, 10H); MS [M-CF$_3$COO]$^+$: 501.

EXAMPLE 71

3-(R)(Benzylphenylcarbamoyloxy)-1-[3-(5,6,7,8-tetrahydronaphthalen-2-yloxy)propyl]-1-azoniabicyclo[2.2.2]octane; trifluoroacetate The title compound was synthesised according to method d. The yield of the final step was 10 mg, 21%; $^1$H-NMR (DMSO-$d_6$): δ 1.50-1.71 (m, 6H), 1.87-2.19 (m, 5H), 2.63-2.68 (m, 4H), 3.10 (bs, 1H), 3.28-3.50 (m, 6H), 3.88 (m, 1H), 3.98 (m, 2H), 4.93 (s, 2H), 5.02 (m, 1H), 6.63-6.70 (m, 2H), 6.95-6.98 (d, 1H), 7.19-7.38 (m, 10H); MS [M-CF$_3$COO]$^+$: 525.

EXAMPLE 72

1-[3-Benzo[1,3]dioxol-5-yloxy)propyl]-3-(R)(benzylphenylcarbamoyloxy)-1-azoniabicyclo[2.2.2]octane; trifluoroacetate The title compound was synthesised according to method d. The yield of the final step was 12 mg, 26%; MS [M-CF$_3$COO]$^+$: 515.

EXAMPLE 73

3-(R)(Benzylphenylcarbamoyloxy)-1-[3-(2-carbamoylphenoxy)propyl]-1azoniabicyclo[2.2.2]octane; trifluoroacetate The title compound was synthesised according to method d. The yield of the final step was 10 mg, 22%; $^1$H-NMR (DMSO-$d_6$): δ 1.50-2.27 (m, 7H), 3.09 (bs, 1H), 3.28-3.48 (m, 6H), 3.88 (m, 1H), 4.14 (m, 2H), 4.93 (s, 2H), 5.04 (m, 1H), 7.02-7.15 (m, 2H), 7.19-7.38 (m, 10H), 7.44-7.50 (m, 1H), 7.55(bs, NH$_2$), 7.69-7.72 (dd, 1H); MS [M-CF$_3$COO]$^+$: 514.

EXAMPLE 74

3-(R)(Benzylphenylcarbamoyloxy)-1-[3-(3-dimethylaminophenoxy)propyl]-1-azoniabicyclo[2.2.2]octane; trifluoroacetate The title compound was synthesised according to method d. The yield of the final step was 12 mg, 26%; MS [M-CF$_3$COO]$^+$: 514.

EXAMPLE 75

1-[3-(4-Acetylaminophenoxy)propyl]-3-(R)(benzylphenylcarbamoyloxy)-1-azoniabicyclo[2.2.2]octane; trifluoroacetate The title compound was synthesised according to method d. The yield of the final step was 12 mg, 25%; $^1$H-NMR (DMSO-$d_6$): δ 1.50-1.92 (m, 4H), 2.01 (s, 3H), 2.04-2.20 (m, 3H), 3.12 (bs, 1H), 3.28-3.51 (m, 6H), 3.89 (m, 1H), 4.00 (m, 2H), 4.93 (s, 2H), 5.02 (m, 1H), 6.86-6.91 (m, 2H), 7.19-7.38 (m, 10H), 7.48-7.53 (m, 2H), 9.85 (s,NH); MS [M-CF$_3$COO]$^+$: 528.

EXAMPLE 76

3-(R)(Benzylphenylcarbamoyloxy)-1-[3-(4-methoxycarbonylphenoxy)propyl]-1-azoniabicyclo[2.2.2]octane; trifluoroacetate The title compound was synthesised according to method d. The yield of the final step was 12 mg, 25%; $^1$H-NMR (DMSO-$d_6$): δ 1.50-2.20 (m, 7H), 3.12 (bs, 1H), 3.29-3.51 (m, 6H), 3.82 (s, 3H), 3.87-3.93 (m, 1H), 4.14 (m, 2H), 4.93 (s, 2H), 5.03(m, 1H), 7.04-7.09 (m, 2H), 7.19-7.38 (m, 10H), 7.92-7.96 (m, 2H); MS [M-CF$_3$COO]$^+$: 529.

EXAMPLE 77

3-(R)(Benzylphenylcarbamoyloxy)-1-[3-(4-nitrophenoxy)propyl]-1-azoniabicyclo[2.2.2]octane; trifluoroacetate The title compound was synthesised according to method d. The yield of the final step was 12 mg, 26%; $^1$H-NMR (DMSO-$d_6$): δ 1.50-2.27 (m, 7H), 3.12 (bs, 1H), 3.29-3.51 (m, 6H), 3.87-3.94 (m, 1H), 4.21 (m, 2H), 4.93 (s, 2H), 5.03 (m, 1H), 7.14-7.38 (m, 12H), 8.22-8.28 (m, 2H); MS [M-CF$_3$COO]$^+$: 516.

EXAMPLE 78

3-(R)(Benzylphenylcarbamoyloxy)-1-[3-(4-hydroxymethylphenoxy)propyl]-1-azoniabicyclo[2.2.2]octane; trifluoroacetate The title compound was synthesised according to method d. The yield of the final step was 10 mg, 22%; MS [M-CF$_3$COO]$^+$: 501.

EXAMPLE 79

Benzylphenylcarbamic acid 1-azabicyclo[2.2.2]oct-3-(S)yl ester

The title compound was synthesised according to method a. The yield of the final step was 1000 mg, 23%; $^1$H-NMR (DMSO-$_6$): δ 1.14-1.57 (m, 4H), 1.83 (bs, 1H), 2.43-2.61 (m, 5H), 2.61-3.01 (m, 1H), 4.64 (m, 1H), 4.89 (s, 2H), 7.16-7.35 (m, 10H). MS [M+1]$^+$: 337.

EXAMPLE 80

3-(S)(Benzylphenylcarbamoyloxy)-1-(3-phenylpropyl)-1-azoniabicyclo[2.2.2]octane; bromide The title compound was synthesised according to method c. The yield of the final step was 660 mg, 83%. $^1$H-NMR (DMSO-$d_6$) δ 1.40-2.00 (m, 6H), 2.18 (bs, 1H), 2.59 (m, 2H), 2.95-3.44 (m, 7H), 3.84 (m, 1H), 4.92 (s, 2H), 5.00 (m, 1H), 7.19-7.36 (m, 15H). MS [M-Br]$^+$: 455; mp: 64° C.

EXAMPLE 81

3-(R)(Butylphenylcarbamoyloxy)-1-methyl-1-azoniabicyclo[2.2.2]octane; trifluoroacetate The title compound was synthesised according to method d. The yield of the final step was 16 mg, 30%; MS [M-CF$_3$COO]$^+$: 317.

EXAMPLE 82

3-(R)(Butylphenylcarbamoyloxy)-1-(4-methylpent-3-enyl)-1-azoniabicyclo[2.2.2]octane; trifluoroacetate The title compound was synthesised according to method d. The yield of the final step was 18 mg, 27%; MS [M-CF$_3$COO]$^+$: 385.

EXAMPLE 83

3-(R)(Butylphenylcarbamoyloxy)-1-(3-phenoxypropyl)-1-azoniabicyclo[2.2.2]octane; trifluoroacetate The title compound was synthesised according to method d. The yield of the final step was 21 mg, 28%; MS [M-CF$_3$COO]$^+$: 437.

EXAMPLE 84

3-(R)(Butylphenylcarbamoyloxy)-1-(3-phenylallyl)-1-azoniabicyclo[2.2.2]octane; bromide The title compound was synthesised according to method c. The yield of the final step was 182 mg, 48%; $^1$H-NMR (DMSO-d$_6$): δ 0.84 (m, 3H), 1.25 (m, 2H), 1.40 (m, 2H), 1.70-1.91 (m, 4H), 2.20 (s, 1H), 3.2-3.4 (m, 6 H), 3.64 (m, 2H), 3.88 (m, 1H), 3.88-4.07 (d, 2H), 4.97 (m, 1H), 6.45 (m, 1H), 6.83-6.88 (d, 1H), 7.23-7.45 (m, 7H), 7.60 (m, 2H); MS [M-Br]$^+$: 419; mp: 144° C.

EXAMPLE 85

1-Allyl-3-(R)(butylphenylcarbamoyloxy)-1-azoniabicyclo[2.2.2]octane; bromide

The title compound was synthesised according to method c. The yield of the final step was 200 mg, 72%; $^1$H-NMR (DMSO-d$_6$): δ 0.85 (m, 3H), 1.21-1.34 (m, 3H), 1.40-1.45 (m, 2H), 1.70-2.18 (m, 4H), 3.15-3.40 (m,5H), 3.61-3.67 (m, 2H), 3.82 (m, 1H), 3.92-3.94 (m, 2H), 4.95 (m, 1H), 5.62 (m, 2H), 5.97-6.01 (m, 1H), 7.26-7.44 (m, 5H); MS [M-Br]$^+$: 343; mp: 141° C.

EXAMPLE 86

3-(R)(Butylphenylcarbamoyloxy)-1-(2-hydroxyethyl)-1azoniabicyclo[2.2.2]octane; trifluoroacetate The title compound was synthesised according to method d. The yield of the final step was 13 mg, 19%; MS [M-CF$_3$COO]$^+$: 347.

EXAMPLE 87

3-(R)(Butylphenylcarbamoyloxy)-1-isopropyl-1-azoniabicyclo[2.2.2]octane; trifluoroacetate The title compound was synthesised according to method d. The yield of the final step was 20 mg, 29%; MS [M-CF$_3$COO]$^+$: 345.

EXAMPLE 88

3-(R)(Butylphenylcarbamoyloxy)-1-propyl-1-azoniabicyclo[2.2.2]octane; trifluoroacetate The title compound was synthesised according to method d. The yield of the final step was 16 mg, 23%; MS [M-CF$_3$COO]$^+$: 345.

EXAMPLE 89

3-(R)(Butylphenylcarbamoyloxy)-1-(3-cyanopropyl)-1-azoniabicyclo[2.2.2]octane; trifluoroacetate The title compound was synthesised according to method d. The yield of the final step was 15 mg, 20%; MS [M-CF$_3$COO]$^+$: 370.

EXAMPLE 90

3-(R)(Butylphenylcarbamoyloxy)-1-cyclopropylmethyl-1-azoniabicyclo[2.2.2]octane; trifluoroacetate The title compound was synthesised according to method d. The yield of the final step was 2 mg, 3%; MS [M-CF$_3$COO]$^+$: 357.

EXAMPLE 91

3-(R)(Butylphenylcarbamoyloxy)-1-(2-ethoxyethyl)-1-azoniabicyclo[2.2.2]octane; trifluoroacetate The title compound was synthesised according to method d. The yield of the final step was 19 mg, 25%; MS [M-CF$_3$COO]$^+$: 375.

EXAMPLE 92

3-(R)(Butylphenylcarbamoyloxy)-1-(4-ethoxycarbonylbutyl)-1-azoniabicyclo[2.2.2]octane; trifluoroacetate The title compound was synthesised according to method d. The yield of the final step was 12 mg, 14%; MS [M-CF$_3$COO]$^+$: 431.

EXAMPLE 93

3-(R)(Butylphenylcarbamoyloxy)-1-(3-hydroxypropyl)-1-azoniabicyclo[2.2.2]octane; trifluoroacetate The title compound was synthesised according to method d. The yield of the final step was 12 mg, 17%; MS [M-CF$_3$COO]$^+$: 361.

EXAMPLE 94

3-(R)(Butylphenylcarbamoyloxy)-1-(3-pyrrol-1-ylpropyl)-1-azoniabicyclo[2.2.2]octane; trifluoroacetate The title compound was synthesised according to method d. The yield of the final step was 19 mg, 23%; MS [M-CF$_3$COO]$^+$: 410.

EXAMPLE 95

1-(4-Acetoxybutyl)-3-(R)(butylphenylcarbamoyloxy)-1-azoniabicyclo[2.2.2]octane; trifluoroacetate The title compound was synthesised according to method d. The yield of the final step was 10 mg, 12%; MS [M-CF$_3$COO]$^+$: 417.

EXAMPLE 96

3-(R)(Butylphenylcarbamoyloxy)-1-(4-oxo-4-thiophen-2-ylbutyl)-1-azoniabicyclo[2.2.2]octane; trifluoroacetate The title compound was synthesised according to method d. The yield of the final step was 17 mg, 19%; MS [M-CF$_3$COO]$^+$: 455.

EXAMPLE 97

3-(R)(Butylphenylcarbamoyloxy)-1-(4-phenylbutyl)-1-azoniabicyclo[2.2.2]octane; trifluoroacetate The title compound was synthesised according to method d. The yield of the final step was 17 mg, 20%; MS [M-CF$_3$COO]$^+$: 435.

EXAMPLE 98

3-(R)(Butylphenylcarbamoyloxy)-1-[3-(3-hydroxyphenoxy)propyl]-1-azoniabicyclo[2.2.2]octane; trifluoroacetate The title compound was synthesised according to method d. The yield of the final step was 21 mg, 23%; MS [M-CF$_3$COO]$^+$: 453.

EXAMPLE 99

3-(R)(Butylphenylcarbamoyloxy)-1-heptyl-1-azoniabicyclo[2.2.2]octane; trifluoroacetate The title compound was synthesised according to method d. The yield of the final step was 17 mg, 21%; MS [M-CF$_3$COO]$^+$: 401.

EXAMPLE 100

1-(2-Benzyloxyethyl)-3-(R)(butylphenylcarbamoyloxy)-1-azoniabicyclo[2.2.2]octane; trifluoroacetate The title compound was synthesised according to method d. The yield of the final step was 22 mg, 25%; MS [M-CF$_3$COO]$^+$: 437.

EXAMPLE 101

3-(R)(Butylphenylcarbamoyloxy)-1-phenethyl-1-azoniabicyclo[2.2.2]octane; bromide The title compound was synthesised according to method c. The yield of the final step was 330 mg 82%; $^1$H-NMR (DMSO-d$_6$): δ 0.83 (m, 3H), 1.27-1.34 (m, 2H), 1.41-1.48 (m, 3H), 1.60-2.23 (m, 4H), 2.96-3.47 (m, 7H), 3.57-3.71 (m, 4H), 3.92 (m, 1H), 4.98 (m, 1H), 7.25-7.45 (m, 10H); MS [M-Br]$^+$: 407; mp: 139° C.

EXAMPLE 102

3-(R)(Butylphenylcarbamoyloxy)-1-[2-(2-methoxyethoxy)ethyl]-1-azoniabicyclo[2.2.2]octane; bromide The title compound was synthesised according to method c. The yield of the final step was 520 mg, 81%; $^1$H-NMR (DMSO-d$_6$): δ 0.82 (m, 3H), 1.24-1.31 (m, 2H), 1.39-1.47 (m, 2H), 1.70-2.20 (m, 5 H), 3.26 (s, 3H), 3.35-3.70 (m, 13H), 3.82-3.86 (m, 3H), 4.94 (m, 1H), 7.26-7.44 (m, 5 H); MS [M-Br]$^+$: 405.

EXAMPLE 103

Butyl-(4-fluorophenyl)carbamic acid 1-azabicyclo[2.2.2]oct-3-(R)yl ester

The title compound was synthesised according to method a. The yield of the final step was 1650 mg, 24%; $^1$H-NMR (DMSO-d$_6$): δ 0.82 (m, 3H), 1.20-1.54 (m, 8H), 1.83 (m, 1H), 2.49-2.70) (m, 5H), 3.02-3.09 (m, 1H), 3.36-3.63 (m, 2H), 4.59 (m, 1H), 7.19-7.35 (m, 4H); MS [M+1]$^+$: 321.

EXAMPLE 104

3-(R)(Butylphenylcarbamoyloxy)-1-[3-(4-fluorophenoxy)propyl]-1-azoniabicyclo[2.2.2]octane; chloride The title compound was synthesised according to method c. The yield of the final step was 390 mg, 75%; $^1$H-NMR (DMSO-d$_6$): δ 0.82 (m, 3H), 1.26-1.31 (m, 2H), 1.40-1.48 (m, 2H), 1.70-2.17 (m,5H), 3.20-3.7 (m, 11H), 3.86 (m, 1H), 4.02 (m, 2H), 4.94 (m, 1H), 6.95-7.00 (m, 2H), 7.12-7.18 (m, 2H), 7.26-7.44 (m, 5H); MS [M-Cl]$^+$: 455; mp: 126° C.

EXAMPLE 105

3-(R)(Butylphenylcarbamoyloxy)-1-(2-phenoxyethyl)-1-azoniabicyclo[2.2.2]octane; bromide The title compound was synthesised according to method c. The yield of the final step was 260 mg, 53%; $^1$H-NMR (DMSO-d$_6$): δ 0.84 (m, 3H), 1.23-1.30 (m, 2H), 1.39-1.48 (m, 2H), 1.70-2.20 (m, 5H), 3.20-3.72 (m, 9H), 3.99 (m, 1H), 4.44 (m, 2H), 4.95 (m, 1H), 7.01 (m, 3H), 7.24-7.40 (m, 7H); MS [M-Br]$^+$: 423; mp: 153° C.

EXAMPLE 106

3-(R)(Butylphenylcarbamoyloxy)-1-(3-thiophen-2-ylpropyl)-1-azoniabicyclo[2.2.2]octane; bromide The title compound was synthesised according to method c. The yield of the final step was 1100 mg, 62%; $^1$H-NMR (DMSO-d$_6$): δ 0.84 (m,3H), 1.24-1.31 (m, 2H), 1.42 (m, 2H), 1.60-2.21 (m, 7H), 2.85 (m, 2H), 3.0-3.50 (m, 7H), 3.60-3.69 (m, 2H), 3.85 (m, 1H), 4.93 (m, 1H), 6.95-7.00 (m, 2H), 7.28-7.43 (m, 6H); MS [M-Br]$^+$: 427; mp: 127° C.

EXAMPLE 107

3-(R)(Butylphenylcarbamoyloxy)-1-(3-phenylpropyl)-1-azoniabicyclo[2.2.2]octane; bromide The title compound was synthesised according to method c. The yield of the final step was 280 mg, 56%; $^1$H-NMR (DMSO-d$_6$): δ 0.84 (m, 3H), 1.23-1.33 (m, 2H), 1.43 (m, 2H), 1.60-2.20 (m, 7H), 2.59 (m, 2H), 3.00-3.78 (m, 9H), 3.84 (m, 1H), 4.92 (m, 1H), 7.20-7.42 (m, 10H); MS [M-Br]$^+$: 421; mp: 120° C.

EXAMPLE 108

Phenylthiophen-2-ylmethylcarbamic acid 1-azabicyclo[2.2.2]oct-3-(R)yl ester

The title compound was synthesised according to method a. The yield of the final step was 310 mg, 10%; $^1$H-NMR (DMSO-d$_6$): δ 1.10-1.60 (m, 4 H), 1.87 (s, 1H), 2.46-2.63 (m, 5H), 3.04-3.33 (m, 1H), 4.66 (m, 1H), 5.01 (s, 2H), 6.87-6.94 (m, 2H), 7.20-7.43 (m, 6H); MS [M+1]$^+$: 343.

EXAMPLE 109

1-Methyl-3-(R)(phenylthiophen-2-ylmethylcarbamoyloxy)-1-azoniabicyclo[2.2.2]octane; bromide The title compound was synthesised according to method c. The yield of the final step was 160 mg, 80%; $^1$H-NMR (DMSO-d$_6$): 1.65-2.00 (m, 4H), 2.20 (s, 1 H), 2.98 (s, 3H), 3.32-3.52 (m, 5H), 3.85-3.92 (m, 1H), 4.98-5.04 (m, 3H), 6.94 (m, 2H), 7.24-7.45 (m, 6H); MS [M-Br]$^+$: 357.

EXAMPLE 110

1-(3-Phenoxypropyl)-3-(R)(phenylthiophen-2-ylmethylcarbamoyloxy)1-azoniabicyclo[2.2.2]octane; trifluoroacetate The title compound was synthesised-according to method d. The yield of the final step was 16 mg, 42%; MS [M-CF$_3$COO]$^+$: 477.

EXAMPLE 111

1-(3-Phenylpropyl)-3-(R)(phenylthiophen-2-ylmethylcarbamoyloxy)-1-azoniabicyclo[2.2.2]octane; trifluoroacetate The title compound was synthesised according to method d. The yield of the final step was 13 mg, 35%; $^1$H-NMR (DMSO-d$_6$): δ 1.72-2.3 (m, 7H), 2.58 (m, 2H), 3.00-3.48 (m, 7H), 3.84 (m, 1H), 5.04 (m, 3H), 6.92-6.94 (m, 2H), 7.20-7.43 (m, 11H); MS [M-CF$_3$COO]$^+$: 461.

EXAMPLE 112

1-(3-Phenylallyl)-3-(R)(phenylthiophen-2-ylmethylcarbamoyloxy)-1-azoniabicyclo[2.2.2]octane; trifluoroacetate The title compound was synthesised according to method d. The yield of the final step was 4 mg, 11%; MS [M-CF$_3$COO]$^+$: 459.

EXAMPLE 113

1-(2-Benzyloxyethyl)-3-(R)(phenylthiophen-2-ylmethylcarbamoyloxy)-1-azoniabicyclo[2.2.2]octane; trifluoroacetate The title compound was synthesised according to method d. The yield of the final step was 14 mg, 37%; MS [M-CF$_3$COO]$^+$: 477.

EXAMPLE 114

1-[3-(3-Hydroxyphenoxy)propyl]-3-(R)(phenylthiophen-2-ylmethylcarbamoyloxy)-1-azoniabicyclo[2.2.2]octane; trifluoroacetate The title compound was synthesised according to method d. The yield of the final step was 11 mg, 28%, MS [M-CF$_3$COO]$^+$: 493.

EXAMPLE 115

1-Heptyl-3-(R)(phenylthiophen-2-ylmethylcarbamoyloxy)-1-azoniabicyclo[2.2.2]octane; trifluoroacetate The title compound was synthesised according to method d. The yield of the final step was 13 mg, 37%; MS [M-CF$_3$COO]$^+$: 441.

EXAMPLE 116

3-(R)(phenylthiophen-2-ylmethylcarbamoyloxy)-1-(3-thiophen-2-ylpropyl)-1-azoniabicyclo[2.2.2]octane; bromide The title compound was synthesised according to method c. The yield of the final step was 140 mg, 48%; $^1$H-NMR (DMSO-d$_6$): δ 1.40-2.30 (m, 7H), 2.83 (m, 2H), 3.00-3.60 (m, 7H), 3.88 (m, 1H), 5.04 (m, 3H), 6.93-6.99 (m, 4H), 7.28-7.43 (m, 7H); MS [M-Br]$^+$: 467.

EXAMPLE 117

1-(2-Phenoxyethyl)-3-(R)(phenylthiophen-2-ylmethylcarbamoyloxy)-1-azoniabicyclo[2.2.2]octane; bromide The title compound was synthesised according to method c. The yield of the final step was 510 mg, 80%; $^1$H-NMR (DMSO-d$_6$): δ 1.40-2.30 (m, 5H), 3.20-3.73 (m, 7H), 4.05 (m, 1H), 4.44 (bs, 2H), 5.04 (m, 3H), 6.91-7.04 (m, 5H), 7.24-7.41 (m, 8H); MS [M-Br]$^+$: 463; mp: 133° C.

EXAMPLE 118

1-Allyl-3-(R)(phenylthiophen-2-ylmethylcarbamoyloxy)-1-azoniabicyclo[2.2.2]octane; bromide The title compound was synthesised according to method c. The yield of the final step was 360 mg, 66%; $^1$H-NMR (DMSO-d$_6$): δ 1.40-2.30 (m, 5H), 3.00-3.41 (m, 5H), 3.81-3.92 (m, 3H), 5.04 (m, 3H), 5.61 (m, 2H), 5.93-6.05 (m, 1H), 6.93-6.96 (m, 2H), 7.24-7.46 (m, 6H); MS [M-Br]$^+$: 383; mp: 110° C.

EXAMPLE 119

Phenethylphenylcarbamic acid 1-azabicyclo[2.2.2]oct-3-(R)yl ester

The title compound was synthesised according to method a. The yield of the final step was 1400 mg, 17%; $^1$H-NMR (DMSO-d$_6$): δ 1.10-1.60 (m, 4H), 1.83 (s, 1H), 2.40-2.70 (m, 5H), 2.78 (m, 2H), 3.00-3.08 (m, 1H), 3.87 (m, 2H), 4.58 (m, 1H), 7.16-7.40 (m, 10H); MS [M+1]$^+$: 351.

EXAMPLE 120

1-Methyl-3-(R)(phenethylphenylcarbamoyloxy)-1-azoniabicyclo[2.2.2]octane; bromide The title compound was synthesised according to method c. The yield of the final step was 140 mg, 73%; $^1$H-NMR (DMSO-d$_6$): δ 1.40-2.30 (m, 5H), 2.80 (m, 2H), 2.94 (s, 3H), 3.10-3.50 (m, 5H), 3.78-3.95 (m, 3H), 4.89 (m, 1H), 7.16-7.41 (m, 10H); MS [M-Br]$^+$: 365; mp: 203° C.

EXAMPLE 121

1-Allyl-3-(R)(phenethylphenylcarbamoyloxy)-1-azoniabicyclo[2.2.2]octane; trifluoroacetate The title compound was synthesised according to method d. The yield of the final step was 11 mg, 35%; MS [M-CF$_3$COO]$^+$: 391.

EXAMPLE 122

3-(R)(Phenethylphenylcarbamoyloxy)-1-(3-phenoxypropyl)-1-azoniabicyclo[2.2.2]octane; trifluoroacetate The title compound was synthesised according to method d. The yield of the final step was 16 mg, 41%; MS [M-CF$_3$COO]$^+$: 485.

EXAMPLE 123

3-(R)(Phenethylphenylcarbamoyloxy)-1-(2-phenoxyethyl)-1-azoniabicyclo[2.2.2]octane; trifluoroacetate The title compound was synthesised according to method d. The yield of the final step was 15 mg, 40%; $^1$H-NMR (DMSO-d$_6$): δ 1.45-2.18 (m, 5H), 2.81 (m, 2H), 3.28-3.70 (m, 7H), 3.80-4.02 (m, 3H), 4.43 (m, 2H), 4.95 (m, 1H), 6.98-7.04 (m, 2H), 7.16-7.40 m, 13H); MS [M-CF$_3$COO]$^+$: 471.

EXAMPLE 124

3-(R)(Phenethylphenylcarbamoyloxy)-1-(3-phenylpropyl)-1-azoniabicyclo[2.2.2]octane; trifluoroacetate The title compound was synthesised according to method d. The yield of the final step was 14 mg, 37%; $^1$H-NMR (DMSO-d$_6$): δ 1.45-2.20 (m, 7H), 2.59 (m, 2H), 2.81 (m, 2H), 3.05-3.5 (m, 7H), 3.78-3.89 (m, 3H), 4.91 (m, 1H), 7.17-7.42 (m, 15H); MS [M-CF$_3$COO]$^+$: 469.

EXAMPLE 125

3-(R)(Phenethylphenylcarbamoyloxy)-1-(3-phenylallyl)-1-azoniabicyclo[2.2.2]octane; trifluoroacetate The title compound was synthesised according to method d. The yield of the final step was 4 mg, 11%; MS [M-CF$_3$COO]$^+$: 467

EXAMPLE 126

1-(2-Benzyloxyethyl)-3-(R)(phenethylphenylcarbamoyloxy)-1-azoniabicyclo[2.2.2]octane; trifluoroacetate The title compound was synthesised according to method d. The yield of the final step was 14 mg, 36%; MS [M-CF$_3$COO]$^+$: 485.

EXAMPLE 127

1-[3-(3-Hydroxyphenoxy)propyl]-3-(R)(phenethylphenylcarbamoyloxy)-1-azoniabicyclo[2.2.2]octane; trifluoroacetate The title compound was synthesised according to method d. The yield of the final step was 14 mg, 35%; $^1$H-NMR (DMSO-d$_6$): δ 1.45-2.20 (m, 7H), 2.82 (m, 2H), 3.05-3.50 (m, 7H), 3.83-3.99 (m, 5H), 4.94 (m, 1H), 6.33-6.39 (m, 3H), 7.04-7.09 (m, 1H), 7.18-7.44(m, 10H), 9.49 (s, OH); MS [M-CF$_3$COO]$^+$: 501.

EXAMPLE 128

1-Heptyl-3-(R)(phenethylphenylcarbamoyloxy)-1-azoniabicyclo[2.2.2]octane; trifluoroacetate The title compound was synthesised according to method d. The yield of the final step was 15 mg, 42%; $^1$H-NMR (DMSO-d$_6$): δ 0.88 (m, 3H), 1.28 (m, 8H), 1.55-2.20 (m, 7H), 2.82 (m, 2H), 3.00-3.50 (m, 7H), 3.68-3.89 (m, 3H), 4.92 (m, 1H), 7.18-7.43 (m, 10H); MS [M-CF$_3$COO]$^+$: 449.

EXAMPLE 129

3-(R)(Phenethylphenylcarbamoyloxy)-1-(3-thiophen-2-ylpropyl)-1-azoniabicyclo[2.2.2]octane; trifluoroacetate The title compound was synthesised according to method d. The yield of the final step was 15 mg, 39%; MS [M-CF$_3$COO]$^+$: 475.

EXAMPLE 130

Pentylphenylcarbamic acid 1-azabicyclo[2.2.2]oct-3-(R)yl ester

The title compound was synthesised according to method a. The yield of the final step was 620 mg, 9%; $^1$H-NMR (DMSO-d$_6$): δ 0.83 (m, 3H), 1.22-1.30 (m, 5H), 1.43-1.56 (m, 5H), 1.83 (s, 1H), 2.42-2.65 (m, 5H), 3.01-3.06 (m, 1 H), 3.59-3.65 (m, 2H), 4.49 (m, 1H), 7.22-7.41 (m, 5 H); MS [M+1]$^+$: 317.

EXAMPLE 131

1-Methyl-3-(R)(pentylphenylcarbamoyloxy)-1-azoniabicyclo[2.2.2]octane; bromide

The title compound was synthesised according to method c. The yield of the final step was 130 mg, 68%, $^1$H-NMR (DMSO-d$_6$): δ 0.81 (m, 3H), 1.21 (m, 5H), 1.45-2.20 (m, 6H), 2.93 (s, 3H), 3.10-3.70 (m, 7H), 3.80 (m, 1H), 4.88 (m, 1H), 7.24-7.41 (m, 5H); MS [M-Br]⁺: 331.

EXAMPLE 132

1-Allyl-3-(R)(pentylphenylcarbamoyloxy)-1-azoniabicyclo[2.2.2]octane; trifluoroacetate The title compound was synthesised according to method d. The yield of the final step was 10 mg, 35%; $^1$H-NMR (DMSO-d$_6$): δ 0.83 (m, 3H), 1.21-1.28 (m, 4H), 1.46 (m, 3H), 1.54-1.91 (m, 3H), 2.30 (m, 1H), 3.28-3.41 (m, 5H), 3.78-3.92 (m, 5H), 4.94 (m, 1H), 5.54-5.64 (m, 2H), 5.98 (m, 1H), 7.26-7.43 (m, 5H); MS [M-CF$_3$COO]⁺: 357.

EXAMPLE 133

3-(R)(Pentylphenylcarbamoyloxy)-1-(3-phenoxypropyl)-1-azoniabicyclo[2.2.2]octane; trifluoroacetate The title compound was synthesised according to method d. The yield of the final step was 13 mg, 36%; MS [M-CF$_3$COO]⁺: 451.

EXAMPLE 134

3-(R)(Pentylphenylcarbamoyloxy)-1-(2-phenoxyethyl)-1-azoniabicyclo[2.2.2]octane; trifluoroacetate The title compound was synthesised according to method d. The yield of the final step was 14 mg, 40%; $^1$H-NMR (DMSO-d$_6$): δ 0.82 (m, 3H), 1.23 (m, 4H), 1.46 (m, 3H), 1.54-1.91 (m, 3H), 2.25 (s, 1H), 3.28-3.70 (m, 9H), 3.98 (m, 1H), 4.43 (m, 2H), 4.95 (m, 1H), 6.98-7.04 (m, 3H), 7.23-7.4 (m, 7H); MS [M-CF$_3$COO]⁺: 437.

EXAMPLE 135

3-(R)(Pentylphenylcarbamoyloxy)-1-(3-phenylpropyl)-1-azoniabicyclo[2.2.2]octane; trifluoroacetate The title compound was synthesised according to method d. The yield of the final step was 13 mg, 37%; $^1$H-NMR (DMSO-d$_6$): δ 0.82 (m, 3H), 1.20-1.25 (m, 5H), 1.44 (m, 3H), 1.68-2.13 (m, 7H), 2.58 (m, 2H), 3.00-3.41 (m, 5H), 3.54-3.69 (m, 2H), 3.79-3.85 (m, 1H), 4.92 (m, 1H), 7.20-7.42 (m, 10H); MS [M-CF$_3$COO]⁺: 435.

EXAMPLE 136

3-(R)(Pentylphenylcarbamoyloxy)-1-(3-phenylallyl)-1-azoniabicyclo[2.2.2]octane; trifluoroacetate The title compound was synthesised according to method d. The yield of the final step was 4 mg, 12%; MS [M-CF$_3$COO]⁺: 433.

EXAMPLE 137

1-(2-Benzyloxyethyl)-3-(R)(pentylphenylcarbamoyloxy)-1-azoniabicyclo[2.2.2]octane; trifluoroacetate The title compound was synthesised according to method d. The yield of the final step was 15 mg, 42%; MS [M-CF$_3$COO]⁺: 451.

EXAMPLE 138

1-[3-(3-Hydroxyphenoxy)propyl]-3-(R)(pentylphenylcarbamoyloxy)-1-azoniabicyclo[2.2.2]octane; trifluoroacetate The title compound was synthesised according to method d. The yield of the final step was 12 mg 32%; MS [M-CF$_3$COO]⁺: 467.

EXAMPLE 139

1-Heptyl-3-(R)(pentylphenylcarbamoyloxy)-1-azoniabicyclo]2.2.2]octane; trifluoroacetate The title compound was synthesised according to method d. The yield of the final step was 15 mg, 45%; MS [M-CF$_3$COO]⁺: 415.

EXAMPLE 140

3-(R)(Pentylphenylcarbamoyloxy)-1-(3-thiophen-2-ylpropyl)-1-azoniabicyclo[2.2.2]octane; trifluoroacetate The title compound was synthesised according to method d. The yield of the final step was 13 mg, 37%; $^1$H-NMR (DMSO-d$_6$): δ 0.82 (m, 3H), 1.22-1.26 (m, 5H), 1.46 (m, 3H), 1.60-2.14 (m, 7H), 2.82 (m, 2H), 3.20-3.41 (m, 5H), 3.50-3.70 (m, 2H), 3.82 (m, 1H), 4.92 (m, 1H), 6.93-6.99 (m, 2H), 7.25-7.43 (m, 6H); MS M CF$_3$COO]⁺: 441.

EXAMPLE 141

Pent-4-enylphenylcarbamic acid 1-azabicyclo[2.2.2]oct-3-(R)yl ester

The title compound was synthesised according to method a The yield of the final step was 690 mg, 14%; $^1$H-NMR (DMSO-d$_6$): δ 1.10-1.60 (m, 6H), 1.84 (bs, 1H), 1.97-2.04 (m, 2H), 2.45-2.65 (m, 5H), 3.02-3.10 (m, 1H), 3.29-3.66 (m, 2H), 4.59 (m, 1H), 4.61-5.00 (m, 2H), 5.70-5.84 (m, 1H), 7.22-7.42 (m, 5H); MS [M+1]⁻: 315.

EXAMPLE 142

1-Allyl-3-(R)(pent-4-enylphenylcarbamoyloxy)-1-azoniabicyclo[2.2.2]octane; trifluoroacetate The title compound was synthesised according to method d. The yield of the final step was 10 mg, 35%; MS [M-CF$_3$COO]⁺: 355.

EXAMPLE 143

3-(R)(Pent-4-enylphenylcarbamoyloxy)-1-(3-phenoxypropyl)-1-azoniabicyclo[2.2.2]octane; trifluoroacetate The title compound was synthesised according to method d. The yield of the final step was 15 mg, 42%; $^1$H-NMR (DMSO-d$_6$): δ 1.50-2.20 (m, 11H), 3.23-3.47 (m, 7H), 3.56-3.73 (m, 2H), 3.87 (m, 1H), 4.03 (m, 2H), 4.92-4.95 (m, 2H), 5.00 (m, 1H), 5.70-5.82 (m, 1H), 6.93-6.99 (m, 2H), 7.26-7.44 (m, 8H); MS [M-CF$_3$COO]⁺: 449.

EXAMPLE 144

3-(R)(Pent-4-enylphenylcarbamoyloxy)-1-(2-phenoxyethyl)-1-azoniabicyclo[2.2.2]octane; trifluoroacetate The title compound was synthesised according to method d. The yield of the final step was 13 mg, 37%; $^1$H-NMR (DMSO-d$_6$): δ 1.55 (m, 2H), 1.65-2.20 (m, 7H), 3.28-3.75 (m, 9H), 3.98 (m, 1H), 4.43 (bs, 2H), 4.92-4.99 (m, 3H), 5.70-5.83 (m, 1H), 6.98-7.04 (m, 3H), 7.24-7.40 (m, 7H); MS [M-CF$_3$COO]$^+$; 435.

EXAMPLE 145

3-(R)(Pent-4-enylphenylcarbamoyloxy)-1-(3-phenylpropyl)-1-azoniabicyclo[2.2.2]octane; trifluoroacetate The title compound was synthesised according to method d. The yield of the final step was 13 mg, 37%; $^1$H-NMR (DMSO-d$_6$): δ 1.56 (m, 3H), 1.70-2.14 (m, 8H), 2.58 (m, 2H), 3.19-3.41 (m, 7H), 3.56-3.71 (m, 2H), 3.81 (m, 1H), 4.92-4.99 (m, 3H), 5.70-5.83 (m 1H), 7.20-7.43 (m, 10H); MS [M-CF$_3$COO]$^+$: 433.

EXAMPLE 146

3-(R)(Pent-4-enylphenylcarbamoyloxy)-1-(3-phenylallyl)-1-azoniabicyclo[2.2.2]octane; trifluoroacetate The title compound was synthesised according to method d. The yield of the final step was 4 mg, 12%; MS [M-CF$_3$COO]$^+$: 431.

EXAMPLE 147

1-(2-Benzyloxyethyl)-3-(R)(pent-4-enylphenylcarbamoyloxy)-1-azoniabicyclo[2.2.2]octane; trifluoroacetate The title compound was synthesised according to method d. The yield of the final step was 16 mg, 44%; MS [M-CF$_3$COO]$^+$: 449.

EXAMPLE 148

1-[3-(3-Hydroxyphenoxy)propyl]-3-(R)(pent-4-enylphenylcarbamoyloxy)-1-azoniabicyclo[2.2.2]octane; trifluoroacetate The title compound was synthesised according to method d. The yield of the final step was 12 mg, 32%; MS [M-CF$_3$COO]$^+$: 465.

EXAMPLE 149

1-Heptyl-3-(R)(pent-4-enylphenylcarbamoyloxy)-1-azoniabicyclo[2.2.2]octane; trifluoroacetate The title compound was synthesised according to method d. The yield of the final step was 3 mg, 9%; MS [M-CF$_3$COO]$^+$: 413.

EXAMPLE 150

1-Methyl-3-(R)(pent-4-enylphenylcarbamoyloxy)-1-azoniabicyclo[2.2.2]octane; trifluoroacetate The title compound was synthesised according to method d. The yield of the final step was 13 mg, 49%; MS [M-CF$_3$COO]$^+$: 429.

EXAMPLE 151

3-(R)(Pent-4-enylphenylcarbamoyloxy)-1-(3-thiophen-2-ylpropyl)-1-azoniabicyclo[2.2.2]octane; trifluoroacetate The title compound was synthesised according to method d. The yield of the final step was 15 mg, 43%; $^1$H-NMR (DMSO-d$_6$): δ 1.40-2.20 (m, 11H), 2.82 (m,2H), 3.05-3.5 (m, 7H), 3.58-3.86 (m, 3H), 4.92-4.95 (m, 2H) 5.00 (m, 1H), 5.70-5.84 (m, 1H), 6.93-7.00 (m, 2H), 7.26-7.44 (m, 6H); MS [M-CF$_3$COO]$^+$: 439.

EXAMPLE 152

Phenylthiophen-3-ylmethylcarbamic acid 1-azabicyclo[2.2.2]oct-3-(R)yl ester

The title compound was synthesised according to method a. The yield of the final step was 2000 mg, 15%; $^1$H-NMR (DMSO-d$_6$): δ 1.10-1.60 (m, 4H), 1.84 (bs, 1H), 2.46-2.62 (m, 5H), 3.02-3.10 (m, 1H), 4.62-4.67 (m, 1H), 4.84 (s, 2H), 6.99 (m, 1H), 7.18-7.36 (m, 6H), 7.47-7.50 (m, 1H); MS [M+1]$^+$: 343.

EXAMPLE 153

1-Allyl-3-(R)(phenylthiophen-3-ylmethylcarbamoyloxy)-1-azoniabicyclo[2.2.2]octane; trifluoroacetate The title compound was synthesised according to method d. The yield of the final step was 8 mg, 26%; $^1$H-NMR (DMSO-d$_6$): δ 1.45-2.00 (m, 4H), 2.21 (bs, 1H), 3.04-3.42 (m, 5H), 3.78-3.91 (m, 3H), 4.87 (s, 2H), 5.02 (m, 1H), 5.54-5.64 (m, 2H), 5.91-6.02 (m, 1H), 7.00-7.02 (m, 1H), 7.22-7.39 (m, 6H), 7.50-7.52 (m, 1H); MS [M-CF$_3$COO]$^+$: 383.

EXAMPLE 154

1-(3-Phenoxypropyl)-3-(R)(phenylthiophen-3-ylmethylcarbamoyloxy)-1-azoniabicyclo[2.2.2]octane; trifluoroacetate The title compound was synthesised according to method d. The yield of the final step was 12 mg, 31%; MS [M-CF$_3$COO]$^+$: 477.

EXAMPLE 155

1-(3-Phenylpropyl)-3-(R)(phenylthiophen-3-ylmethylcarbamoyloxy)-1-azoniabicyclo[2.2.2]octane; trifluoroacetate The title compound was synthesised according to method d. The yield of the final step was 15 mg, 41%; $^1$H-NMR (DMSO-d$_6$): δ 1.45-2.18 (m, 7H), 2.59 (m, 2H), 3.02-3.44 (m, 7H), 3.84 (m, 1H), 4.87 (s, 2H), 4.99 (m, 1H), 7.00 (m, 1H), 7.21-7.38 (m, 11H), 7.47-7.50 (m, 1H); MS [M-CF$_3$COO]$^+$: 461.

EXAMPLE 156

1-(3-Phenylallyl)-3-(R)(phenylthiophen-3-ylmethyl-carbamoyloxy)-1-azoniabicyclo[2.2.2]octane; trifluoroacetate The title compound was synthesised according to method d. The yield of the final step was 4 mg, 11%; MS [M-CF$_3$COO]$^+$: 459.

EXAMPLE 157

1-(2-Benzyloxyethyl)-3-(R)(phenylthiophen-3-ylmethylcarbamoyloxy)-1-azoniabicyclo[2.2.2]octane; trifluoroacetate The title compound was synthesised according to method d. The yield of the final step was 16 mg, 42%; MS [M-CF$_3$COO]$^+$: 477.

EXAMPLE 158

1-[3-(3-Hydroxyphenoxy)propyl]-3-(R)(phenylthiophen-3-ylmethylcarbamoyloxy)-1-azoniabicyclo[2.2.2]octane; trifluoroacetate The title compound was synthesised according to method d. The yield of the final step was 13 mg, 33%; MS [M-CF$_3$COO]$^+$: 493.

EXAMPLE 159

1-Methyl-3-(R)(phenylthiophen-3-ylmethylcarbamoyloxy)-1-azoniabicyclo[2.2.2]octane; trifluoroacetate The title compound was synthesised according to method d. The yield of the final step was 12 mg, 42%; MS [M-CF$_3$COO]$^+$: 357.

EXAMPLE 160

3-(R)(Phenylthiophen-3-ylmethylcarbamoyloxy)-1-(3-thiophen-2-ylpropyl)-1-azoniabicyclo[2.2.2]octane; bromide The title compound was synthesised according to method c. The yield of the final step was 500 mg, 78%; $^1$H-NMR (DMSO-d$_6$): δ 1.45-2.19 (m, 7H), 2.83 (m, 2H), 3.04-3.13 (m, 1H), 3.19-3.46 (m, 6H), 3.83-3.90 (m, 1H). 4.88 (s, 2H), 4.99 (m, 1H), 6.94 (m, 3H), 7.20-7.40 (m, 7H), 7.49 (m, 1H); MS [M-Br]$^+$: 467; mp: 110° C.

EXAMPLE 161

3-(R)(Phenylthiophen-3-ylmethylcarbamoyloxy)-1-(2-phenoxyethyl)-1-azoniabicyclo[2.2.2]octane;bromide The title compound was synthesised according to method c. The yield of the final step was 350 mg, 63%; $^1$H-NMR (DMSO-d$_6$): δ 1.45-2.20 (m, 5H), 3.27 (m, 1H), 3.40-3.80 (m, 6H), 4.00-4.06 (m, 1H), 4.44 (bs, 2H), 4.87 (s, 2H), 5.02 (m, 1H), 6.99-7.04 (m, 4H), 7.20-7.38 (m, 8H), 7.48 (m, 1H); MS [M-Br]$^+$: 463; mp: 131° C.

EXAMPLE 162

Butylthiophen-2-ylmethylcarbamic acid 1-azabicyclo[2.2.2]oct-3-(R)yl ester

The title compound was synthesised according to method a. The yield of the final step was 1300 mg, 29%; $^1$H-NMR (DMSO-d$_6$): δ 0.85 (m, 3H), 1.19-1.68 (m, 8H), 1.92 (m, 1H), 2.49-2.64 (m, 5H), 3.05-3.22 (m, 3H), 4.56-4.62 (m, 3H), 6.95-7.04 (m, 2H), 7.42-7.44 (m, 1H); MS [M+1]$^+$: 323.

EXAMPLE 163

1-Allyl-3-(R)(butylthiophen-2-ylmethylcarbamoyloxy)-1-azoniabicyclo[2.2.2]octane; trifluoroacetate The title compound was synthesised according to method d. The yield of the final step was 10 mg, 23%; $^1$H-NMR (DMSO-d$_6$): δ 0.86 (m, 3H), 1.20-1.26 (m, 2H), 1.42-1.49 (m, 2H), 1.58-2.05 (m, 4H), 2.32 (bs, 1H), 3.20-3.41 (m, 7H), 3.74-3.94 (m, 3H), 4.51-4.72 (m, 2H), 4.99 (m, 1H), 5.55-5.64 (m, 2H), 5.87-6.10 (m, 1H), 6.99 (m, 1H), 7.08 (m, 1H), 7.46 (m, 1H); MS [M-CF$_3$COO]$^+$: 363.

EXAMPLE 164

3-(R)(Butylthiophen-2-ylmethylcarbamoyloxy)-1-(3-phenylpropyl)-1-azoniabicyclo[2.2.2]octane; trifluoroacetate The title compound was synthesised according to method d. The yield of the final step was 13 mg, 25%; $^1$H-NMR (DMSO-d$_6$): δ 0.85 (m, 3H), 1.19-1.26 (m, 2H),1.41-1.50 (m, 2H), 1.75-2.10 (m, 6H), 2.30 (bs, 1H), 2.59 (m, 2H), 3.10-3.50 (m, 9H), 3.83 (m, 1 H), 4.50-4.74 (m, 2H), 4.97 (m, 1H), 6.97 (m, 1H), 7.07 (m, 1H), 7.20-7.35 (m, 5H), 7.43 (m, 1H); MS [M-CF$_3$COO]$^+$: 441.

EXAMPLE 165 bis-Thiophen-2-ylmethylcarbamic acid 1-azabicyclo[2.2.2]oct-3-(R)yl ester

The title compound was synthesised according to method a. The yield of the final step was 340 mg, 7%; $^1$H-NMR (DMSO-d$_6$): δ 1.28-1.31 (m, 1H), 1.45-1.72 (m, 3H), 1.94-1.97 (m, 1H), 2.49-2.71 (m, 5H), 3.06-3.14 (m, 1H), 4.50-4.57 (m, 4H),4.62-4.69 (m, 1H), 6.96-7.06 (m, 4H), 7.44-7.46 (m, 2H); MS [M+1]$^+$: 363.

EXAMPLE 166

1-Allyl-3-(R)(bis-thiophen-2-ylmethylcarbamoyloxy)-1-azoniabicyclo[2.2.2]octane; trifluoroacetate The title compound was synthesised according to method d. The yield of the final step was 9 mg, 19%; $^1$H-NMR (DMSO-d$_6$): δ 1.70-2.06 (m, 4H), 2.35 (bs, 1H), 3.25-3.50 (m, 5H), 3.80-3.94 (m, 3H), 4.54-4.71 (m, 4H), 5.10 (m, 1H), 5.55-5.65 (m, 2H), 5.87-6.10 (m, 1H), 6.98-7.01 (m, 2H); 7.06-7.10 (m, 2H), 7.47-7.48 (m, 2H); MS [M-CF$_3$COO]$^+$: 403.

EXAMPLE 167

3-(R)(bis-thiophen-2-ylmethylcarbamoyloxy)-1-(3-phenylpropyl)-1-azoniabicyclo[2.2.2]octane; bromide The title compound was synthesised according to method c. The yield of the final step was 690 mg, 82%; $^1$H-NMR (DMSO-d$_6$): δ 1.78-2.10 (m, 6H), 2.34 (bs, 1H), 2.53-2.63 (m, 2H), 3.23-3.48 (m, 7H), 3.88 (m, 1H), 4.53-4.74 (m, 4H), 5.05 (m, 1H), 6.98-7.01 (m, 2H), 7.02-7.11 (m, 2H), 7.21-7.37 (m, 5H), 7.44-7.48 (m, 2H); MS [M-Br]$^+$: 481.

EXAMPLE 168

Furan-2-ylmethyl-2-thiophen-2-ylmethylcarbamic acid 1-azabicyclo[2.2.2]oct-3-(R)yl ester The title compound was synthesised according to method a. The yield of the final step was 700 mg, 10%; $^1$H-NMR (DMSO-d$_6$): δ 1.10-1.34 (m, 1H), 1.44-1.67 (m, 3H), 1.93 (bs, 1H), 2.50-2.70 (m, 5H), 3.05-3.12 (m, 1H), 3.37-4.40 (m, 2H), 4.57-4.66 (m, 3H), 6.26-6.42 (m, 2H), 6.95-7.03 (m, 2H), 7.45 (m, 1H), 7.61 (m, 1H); MS [M+1]$^+$: 347.

EXAMPLE 169

1-Allyl-3-(R)(furan-2-ylmethylthiophen-2-ylmethylcarbamoyloxy)-1-azoniabicyclo[2.2.2]octane; trifluoroacetate The title compound was synthesised according to method d. The yield of the final step was 7 mg, 15%; MS [M-CF$_3$COO]$^+$: 387.

EXAMPLE 170

3-(R)(Furan-2-ylmethylthiophen-2-ylmethylcarbamoyloxy)-1-(3-phenylpropyl)-1-azoniabicyclo[2.2.2]octane; trifluoroacetate The title compound was synthesised according to method d. The yield of the final step was 11 mg, 20%; $^1$H-NMR (DMSO-d$_6$): δ 1.70-2.10 (m, 6H), 2.31 (bs, 1H), 2.59 (m, 2H), 3.15-3.50 (m, 7H), 3.84 (m, 1H), 4.36-4.56 (m, 4H), 5.03 (m, 1H), 6.32-6.44 (m, 2H), 6.92-7.08 (m, 2H), 7.20-7.35 (m, 5H), 7.41-7.46 (m, 1H), 7.59-7.62 m, 1H); MS [M-CF$_3$COO]$^+$: 465.

EXAMPLE 171

Allylthiophen-2-ylmethylcarbamic acid 1-azabicyclo[2.2.2]oct-3-(R)yl ester

The title compound was synthesised according to method a. The yield of the final step was 3220 mg, 30%; $^1$H-NMR (DMSO-d$_6$): δ 1.20-1.33 (m, 1H), 1.45-1.80 (m, 3H), 1.93 (bs, 1H), 2.49-2.72 (m, 5H), 3.05-3.09 (m, 1H), 3.81-3.83 (m, 2H), 3.83-4.55 (m, 3H), 5.14 (m, 2H), 5.70-5.82 (m, 1H), 6.96-7.04 (m, 2H), 7.44-7.45 (m, 1H); MS [M+1]$^+$: 307.

EXAMPLE 172

1-Allyl-3-(R)(allylthiophen-2-ylmethylcarbamoyloxy)-1-azoniabicyclo[2.2.2]octane; trifluoroacetate The title compound was synthesised according to method d. The yield of the final step was 10 mg, 24%; $^1$H-NMR (DMSO-d$_6$): δ 1.80-2.10 (m, 4H), 2.32 (bs, 1H), 3.20-3.50 (m, 5H), 3.75-3.94 (m, 5H), 4.5-4.69 (m, 2H), 5.01 (m, 1H), 5.10-5.23 (m, 2H), 5.51-5.65 (m, 2H), 5.70-5.85 (m, 1H), 5.90-6.08 (m, 1H), 6.95-7.10 (m, 2H), 7.47 (m, 1H); MS [M-CF$_3$COO]$^+$: 347.

EXAMPLE 173

3-(R)(Allylthiophen-2-ylmethylcarbamoyloxy)-1-(3-phenylpropyl)-1-azoniabicyclo[2.2.2]octane; trifluoroacetate The title compound was synthesised according to method d. The yield of the final step was 11 mg, 22%; $^1$H-NMR (DMSO-d$_6$): δ 1.74-2.10 m, 6H), 2.31 (bs, 1H), 2.59 (m, 2H), 3.16-3.56 (m, 7H), 3.76-3.90 (m, 3H), 4.48-4.71 (m, 2H), 4.99 (m, 1H), 5.11-5.23 (m, 2H), 5.72-5.83 (m, 1H), 6.98 (m, 1H), 7.06-7.07(m, 1H), 7.20-7.35 (m, 5H), 7.44 (m, 1H); MS [M-CF$_3$COO]$^+$: 425.

EXAMPLE 174

1-Allyl-3-(R)(cyclopentylthiophen-2-ylmethylcarbamoyloxy)-1-azoniabicyclo[2.2.2]octane; trifluoroacetate The title compound was synthesised according to method d. The yield of the final step was 10 mg, 22%; $^1$H-NMR (DMSO d): δ 1.40-2.05 (m, 12H), 2.27 (bs, 1H), 3.03,3.42 (m, 5H),3.70-3.95 (m, 3H), 4.15-4.35 (m, 1H), 5.58 (m, 2H), 4.99 (m, 1H), 5.54-5.65 (m, 2H), 5.87-6.10 (m, 1H), 6.97 (m, 1H), 7.03 (m, 1H), 7.41-7.43 (m, 1H); MS [M-CF$_3$COO]$^+$: 375.

EXAMPLE 175

3-(R)(Cyclopentylthiophen-2-ylmethylcarbamoyloxy)-1-(3-phenylpropyl)-1-azoniabicyclo[2.2.2]octane; trifluoroacetate The title compound was synthesised according to method d. The yield of the final step was 13 mg, 24%; $^1$H-NMR (DMSO-d$_6$): δ 1.40-2.10 (m, 14H), 2.25 (bs, 1H), 2.58 (m, 2H), 2.95-3.50 (m, 7H), 3.81 (m, 1H), 4.26 (m, 1H), 4.50-4.70 (m, 2H), 4.97 (m, 1H), 6.93 (m, 1H), 7.03 (m, 1H), 7.20-7.40 (m, 6H); MS [M-CF$_3$COO]$^+$: 453.

EXAMPLE 176

Furan-2-ylmethylphenylcarbamic acid 1-azabicyclo[2.2.2]oct-3-(R)yl ester

The title compound was synthesised according to method a. The yield of the final step was 1400 mg, 18%; $^1$H-NMR (DMSO-d$_6$): δ 1.19-1.60 (m, 4H), 1.84 (bs, 1H), 2.44-2.57 (m, 5H), 3.01-3.09 (m, 1H), 4.63 (m, 1H), 4.82 (s, 2H), 6.21 (m, 1H), 6,36 (m, 1H), 7.20-7.37 (m, 5H), 7.59 (m, 1H); MS [M+1]$^+$; 327.

EXAMPLE 177

1-Allyl-3-(R)(furan-2-ylmethylphenylcarbamoyloxy)-1-azoniabicyclo[2.2.2]octane; trifluoroacetate The title compound was synthesised according to method d. The yield of the final step was 7 mg, 16%; $^1$H-NMR (DMSO-d$_6$): δ; MS [M-CF$_3$COO]$^+$: 367.

EXAMPLE 178

3-(R)(Furan-2-ylmethylphenylcarbamoyloxy)-1-(3-phenylpropyl)-1-azoniabicyclo[2.2.2]octane; trifluoroacetate The title compound was synthesised according to method d. The yield of the final step was 11 mg, 21%; $^1$H-NMR (DMSO-$d_6$): δ 1.65-2.10 (m, 6H), 2.19 (bs, 1H), 2.59 (m, 2H), 3.10-3.50 (m, 7H), 3.83 (m, 1H), 4.85 (bs, 2H), 4.98 (m, 1H), 6.26 (m, 1H), 6.36 (m, 1H), 7.20-7.39 (m, 10H), 7.59 (m, 1H); MS [M-CF$_3$COO]$^+$: 445.

EXAMPLE 179 bis-Furan-2-ylmethylcarbamic acid 1-azabicyclo[2.2.2]oct-3-(R)yl ester

The title compound was synthesised according to method a. The yield of the final step was 2100 mg, 22%; $^1$H-NMR (DMSO-$d_6$): δ 1.20-1.70 (m, 4H), 1.89 (bs, 1H), 2.45-2.71 (m, 5H), 3.00-3.12 (m, 1H), 4.40 (m, 4H), 4.62 (m, 1H), 6.22-6.40 (m, 4H), 7.59 (m, 2H); MS [M+1]$^+$: 331.

EXAMPLE 180

1-Allyl-3-(R)(bis-furan-2-ylmethylcarbamoyloxy)-1-azoniabicyclo[2.2.2]octane; trifluoroacetate The title compound was synthesised according to method d. The yield of the final step was 7 mg, 16%; $^1$H-NMR (DMSO-$d_6$): δ; MS [M-CF$_3$COO]$^+$: 371.

EXAMPLE 181

3-(R)(bis-furan-2-ylmethylcarbamoyloxy)-1-(3-phenylpropyl)-1-azoniabicyclo[2.2.2]octane; trifluoroacetate The title compound was synthesised according to method d. The yield of the final step was 11 mg; 20%; $^1$H-NMR (DMSO-$d_6$): δ 1.70-2.10 (m, 6H), 2.29 (bs, 1H), 2.59 (m, 2H), 3.10-3.50 (m, 7H), 3.82 (m, 1H), 4.32-4.54 (m, 4H), 5.01 (m, 1H), 6.29-6.41 (m, 4H), 7.20-7.35 (m, 5H), 7.57-7.61 (m, 2H); MS [M-CF$_3$COO]$^+$: 449.

EXAMPLE 182

Benzylphenylcarbamic acid 1-azabicyclo[2.2.2]oct-4-yl ester

The title compound was synthesised according to method a. The yield of the final step was 2.56 mg, 1%, as formate; $^1$H-NMR (DMSO-$d_6$): δ 1.81 (m, 6H), 2.83 (m, 6H), 4.81 (s, 2H), 7.14-7.32 (m, 10H), 8.24. (s, 1H); MS [M-HCOO]$^+$: 337

The following examples illustrate pharmaceutical compositions according to the present invention and procedures for their preparation.

EXAMPLE 183

Preparation of a Pharmaceutical Composition: Tablets

Formulation:

| Compound of the present invention | 5.0 mg |
|---|---|
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the compound of the present invention was mixed with 340.8 g of lactose and 85.2 g of microcrystalline cellulose. The mixture was subjected to compression moulding using a roller compactor to give a flake-like compressed material. The flake-like compressed material was pulverized using a hammer mill, and the pulverized material was screened through a 20 mesh screen. A 4.5 g portion of light silicic anhydride and 4.5 g of magnesium stearate were added to the screened material and mixed. The mixer product was subjected to a tablets making machine equipped with a die/punch system of 7.5 mm in diameter, thereby obtaining 3,000 tablets each having 150 mg in weight

EXAMPLE 184

Preparation of a Pharmaceutical Composition: Tablets Coated

Formulation:

| Compound of the present invention | 5.0 mg |
|---|---|
| Lactose | 95.2 mg |
| Corn starch | 40.8 mg |
| Polyvinylpyrrolidone | 7.5 mg |
| Magnesium stearate | 1.5 mg |
| Hydroxypropylcellulose | 2.3 mg |
| Polyethylene glycol | 0.4 mg |
| Titanium dioxide | 1.1 mg |
| Purified talc | 0.7 mg |

Using a fluidized bed granulating machine, 15 g of the compound of the present invention was mixed with 285.6 g of lactose and 122.4 g of corn starch. Separately, 22.5 g of polyvinylpyrrolidone was dissolved in 127.5 g of water to prepare a binding solution. Using a fluidized bed granulating machine, the binding solution was sprayed on the above mixture to give granulates. A 4.5 g portion of magnesium stearate was added to the obtained granulates and mixed. The obtained mixture was subjected to a tablet making machine equipped with a die/punch biconcave system of 6.5 mm in diameter, thereby obtaining 3,000 tablets, each having 150 mg in weight Separately, a coating solution was prepared by suspending 6.9 g of hydroxypropylmethylcellulose 2910, 1.2 g of polyethylene glycol 6000, 3.3 g of titanium dioxide and 2.1 g of purified talc in 72.6 g of water. Using a High Coated, the 3,000 tablets prepared above were coated with the coating solution to give film-coated tablets, each having 154.5 mg in weight.

EXAMPLE 185

Preparation of a Pharmaceutical Composition: Liquid Inhalant

Formulation:

| Compound of the present invention | 400 μg |
|---|---|
| Physiological saline | 1 ml |

A 40 mg portion of the compound of the present invention was dissolved in 90 ml of physiological saline, and the solution was adjusted to a total volume of 100 ml with the same saline solution, dispensed in 1 ml portions into 1 ml capacity ampoule and then sterilized at 115° for 30 minutes to give liquid inhalant.

EXAMPLE 186

Preparation of a Pharmaceutical Composition: Powder Inhalant

Formulation:

| Compound of the present invention | 200 μg |
|---|---|
| Lactose | 4,000 μg |

A 20 g portion of the compound of the present invention was uniformly mixed with 400 g of lactose, and a 200 mg portion of the mixture was packed in a powder inhaler for exclusive use to produce a powder inhalant.

EXAMPLE 187

Preparation of a Pharmaceutical Composition: Inhalation Aerosol

Formulation:

| Compound of the present invention | 200 μg |
|---|---|
| Dehydrated (Absolute) ethyl alcohol USP | 8,400 μg |
| 1,1,1,2-Tetrafluoroethane (HFC-134A) | 46,810 μg |

The active ingredient concentrate is prepared by dissolving 0.0480 g of the compound of the present invention in 2.0160 g of ethyl alcohol. The concentrate is added to an appropriate filling apparatus. The active ingredient concentrate is dispensed into aerosol container, the headspace of the container is purged with Nitrogen or HFC-134A vapour (purging ingredients should not contain more than 1 ppm oxygen) and is sealed with valve. 11.2344 g of HFC-134A propellant is then pressure filled into the sealed container.

The invention claimed is:
1. A compound of formula (I)

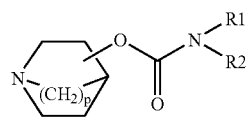

(I)

wherein
R1 represents a group chosen from phenyl, 2-furyl, 3-furyl, 2-thienyl, 3-thienyl, furan-2-ylmethyl, furan-3-ylmethyl, thiophen-2-ylmethyl, and thiophen-3-ylmethyl;

R2 represents a group chosen from optionally substituted lower alkyl, optionally substituted lower alkenyl, optionally substituted lower alkynyl, saturated or unsaturated cycloalkyl, saturated or unsaturated cycloalkylmethyl, phenyl, benzyl, phenethyl, furan-2-ylmethyl, furan-3-ylmethyl, thiophen-2-ylmethyl, thiophen-3-ylmethyl, pyridyl, and pyridylmethyl; wherein the carbocyclic moieties in the cycloalkyl, cycloalkylmethyl, phenyl, benzyl or phenethyl groups are optionally bridged or fused to another saturated, unsaturated or aromatic carbocyclic moiety or to a cyclic moiety comprising carbon atoms and 1 or 2 oxygen atoms;

wherein the cyclic groups present in R1 and R2 are optionally substituted by one, two or three, which may be identical or different, substituents chosen from halogen; straight or branched, optionally substituted lower alkyl; hydroxy; straight or branched, optionally substituted lower alkoxy; —SH; straight or branched optionally substituted lower alkylthio; nitro; cyano; —NR'R"; —CO$_2$R'; —C(O)—NR'R"; —N(R''')C(O)—R'; and —N(R''')—C(O)NR'R"; wherein R', R" and R''', which maybe identical or different, are each independently chosen from a hydrogen atom, and a straight or branched, optionally substituted lower alkyl group, or R' and R" together with the atom to which they are attached form a cyclic group; and p is 1 or 2 and the carbamate group is attached at positions 2, 3 or 4 of the azabicyclic ring;

wherein when the cyclic group present in R1 is unsubstituted or has only one substituent, R2 has at least one substituent;

wherein when
p is 2;
the carbamate group is attached at position 3 of the azabicyclic ring; and
R1 is a phenyl group, which is optionally substituted with one or two, identical or different, substituents chosen from chlorine, fluorine, bromine, methyl, hydroxy and cyano;
then R2 cannot be one of: unsubstituted cyclopropylmethyl; unsubstituted cyclobutylmethyl; unsubstituted cyclopentylmethyl; cyclohexylmethyl optionally substituted with a methyl or an isopropenyl group; unsubstituted cyclohexenyl; unsubstituted norbornenyl; unsubstituted bicycle[2,2,1]heptanyl; unsubstituted benzo[1,3]dioxolyl; unsubstituted 2,3-dihydrobenzo[1,4]dioxinyl; unsubstituted benzyl; a benzyl group which is substituted with one or two, identical or different, substituents chosen from fluorine, chlorine, bromine, methoxy, methyl, trifluoromethyl, ethyl, tertbutyl, hydroxy, hydroxymethyl, cyano, aminocarbonyl, trifluoromethoxy, benzyloxy, and isopropyloxy; or a benzyl group which is substituted with three fluorine atoms;

or a pharmaceutically acceptable salt thereof or a stereoisomer thereof with the proviso that the compound of formula (I) is not one of Diphenylcarbamic acid 1-azabicyclo[2.2.2]oct-3-yl ester, Ethylphenylcarbamic acid 1-azabicyclo[2.2.2]oct-3-yl ester, Quinuclidin-3-yl benzo[d][1,3]dioxol-5-ylmethyl(phenyl) carbamate, or Quinuclidin-3-yl(2,3-dihydrobenzo[b][1,4]dioxin-6-yl) methyl(m-tolyl)carbamate.

2. A compound of formula (II)

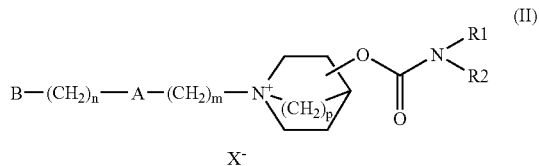

wherein
- R1 represents a group chosen from phenyl, 2-furyl, 3-furyl, 2-thienyl, 3-thienyl, furan-2-ylmethyl, furan-3-ylmethyl, thiophen-2-ylmethyl, and thiophen-3-ylmethyl;
- R2 represents a group chosen from optionally substituted lower alkyl, optionally substituted lower alkenyl, optionally substituted lower alkynyl, saturated or unsaturated cycloalkyl, saturated or unsaturated cycloalkylmethyl, phenyl, benzyl, phenethyl, furan-2-ylmethyl, furan-3-ylmethyl, thiophen-2-ylmethyl, thiophen-3-ylmethyl, pyridyl, and pyridylmethyl; wherein the carbocyclic moieties in the cycloalkyl, cycloalkylmethyl, phenyl, benzyl or phenethyl groups are optionally bridged or fused to another saturated, unsaturated or aromatic carbocyclic moiety or to a cyclic moiety comprising carbon atoms and 1 or 2 oxygen atoms;
- wherein the cyclic groups present in R1 and R2 are optionally substituted by one, two or three, which may be identical or different, substituents chosen from halogen; straight or branched, optionally substituted lower alkyl; hydroxy; straight or branched, optionally substituted lower alkoxy; —SH; straight or branched optionally substituted lower alkylthio; nitro; cyano; NR'R", —CO$_2$R', —C(O)—NR'R", —N(R''')C(O)—R', and —N(R''')—C(O)NR'R" groups, wherein R', R" and R''', which may be identical or different, are each independently chosen from a hydrogen atom and a straight or branched, optionally substituted lower alkyl group, or R'and R" together with the atom to which they are attached form a cyclic group;
- p is 1 or 2 and the carbamate group is attached at positions 2, 3 or 4 of the azabicyclic ring;
- m is an integer ranging from 0 to 8;
- n is an integer ranging from 0 to 4;
- A represents a group chosen from —CH$_2$—; —CH=CR'—; —CR'=CH—; —CR'R"—; —C(O)—, —O—, —S—, —S(O)—, —S(O)$_2$— and —NR'—, wherein R'and R", which may be identical or different, are each independently chosen from a hydrogen atom and a straight or branched, optionally substituted lower alkyl group, or R'and R"together with the atom to which they are attached form a cyclic group;
- B represents a hydrogen atom, or a group chosen from straight or branched, optionally substituted lower alkyl; hydroxy; straight or branched, optionally substituted lower alkoxy; cyano; nitro; —CH=CR'R"; —C(O)OR'; —OC(O)R'; —SC(O)R'; —C(O)NR'R"; —NR'C(O)OR"; —NR'C(O)NR"; cycloalkyl; phenyl; naphthanelyl; 5,6,7,8-tetrahydronaphthanelyl; benzo[1,3]dioxolyl; heteroaryl; and heterocyclyl; wherein R'and R", which may be identical or different, are each independently chosen from a hydrogen atom and a straight or branched, optionally substituted lower alkyl group, or R' and R" together with the atom to which they are attached form a cyclic group; and
- wherein the cyclic groups represented by B are optionally substituted by one, two or three, identical or different, substituents chosen from halogen; hydroxy; straight or branched, optionally substituted lower alkyl; phenyl; —OR'; —SR'; —NR'R"; —NHCOR'; —CONR'R"; —CN; —NO$_2$; and —COOR'; wherein R' and R" are each independently chosen from a hydrogen atom, or a straight or branched, optionally substituted lower alkyl group, or R' and R" together with the atom to which they are attached form a cyclic group; and
- X$^-$ represents a pharmaceutically acceptable anion of a mono or polyvalent acid;
- wherein when the cyclic group present in R1 is unsubstituted or has only one substituent, R2 has at least one substituent;

wherein when
- p is 2;
- the carbamate group is attached at position 3 of the azoniabicyclic ring having (3R)-configuration;
- R1 is a phenyl group which is optionally substituted with a fluorine atom or a methyl group;
- R2 is an unsubstituted cyclohexylmethyl group or a benzyl group which is optionally substituted with one or three fluorine atoms; and
- X$^-$ is iodine;

then, the sequence B—(CH$_2$)$_n$-A-(CH$_2$)$_m$— cannot be a methyl group;

or a stereoisomer thereof; or a mixture of stereoisomers thereof, or a mixture of at least one stereoisomer of a compound of formula (II) and at least one stereoisomer of a compound of formula (I)

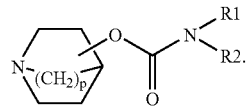

3. The compound of claim 1 wherein when R2 is not substituted, the cyclic group present in R1 has at least two substituents.

4. The compound of claim 1, wherein R1 represents a group chosen from 2-furyl, 3-furyl, 2-thienyl, 3-thienyl, furan-2-ylmethyl, furan-3-ylmethyl, thiophen-2-ylmethyl; and thiophen-3-ylmethyl;
- wherein the cyclic group present in R1 is optionally substituted by one, two, or three, identical or different, substituents chosen from halogen; straight or branched, optionally substituted lower alkyl; hydroxy; straight or branched, optionally substituted lower alkoxy; —SH; straight or branched optionally substituted lower alkylthio; nitro; cyano; —NR'R"; —CO$_2$R'; —C(O)—NR'R"; —N(R''')C(O)—R'; and —N(R''')—C(O)NR'R";
- wherein R', R" and R''' each independently represents a hydrogen atom or a straight or branched, optionally substituted lower alkyl group or R' and R" together with the atom to which they are attached form a cyclic group.

5. The compound of claim 1, wherein R2 represents an optionally substituted group chosen from lower alkyl, lower alkenyl, lower alkynyl, saturated or unsaturated cycloalkyl, phenyl, phenethyl, furan-2-ylmethyl, furan-3-ylmethyl, thiophen-2-ylmethyl, thiophen-3-ylmethyl, pyridyl, pyridylmethyl, and a saturated or unsaturated cycloalkylmethyl which has at least one substituent and is chosen from substituted cyclopropylmethyl, substituted cyclobutylmethyl and substituted cyclopentylmethyl;
- wherein the substituents of the cyclic group present in R2 are one, two or three, identical or different, substituents chosen from halogen; straight or branched, optionally substituted lower alkyl; hydroxy; straight or branched, optionally substituted lower alkoxy; —SH; straight or branched optionally substituted lower alkylthio; nitro; cyano; —NR'R"; —CO$_2$R'; —C(O)—NR'R"; —N(R''')C(O)—R'; and —N(R''')—C(O)NR'R";

wherein R', R" and R''' each independently represents a hydrogen atom or a straight or branched, optionally substituted lower alkyl group or R' and R" together with the atom to which they are attached form a cyclic group.

6. The compound of claim 2, wherein the compound is not one of:
(3R)-3-(Benzylphenylcarbamoyloxy)-1-methyl-1-azoniabicyclo[2.2.2]octane iodide;
(3R)-3-[(4-Fluorobenzyl)phenylcarbamoyloxy]-1-methyl-1-azoniabicyclo[2.2.2]octane iodide;
(3 R)-3-(Benzyl-o-tolylcarbamoyloxy)-1-methyl-1-azoniabicyclo[2.2.2]octane iodide
(3R)-1-Methyl-3-[o-tolyl-(2,4,5-trifluorobenzyl)carbamoyloxy]-1-azoniabicyclo[2.2.2]octane iodide;
(3R)-3-[(4-Fluorobenzyl)-m-tolylcarbamoyloxy]-1-methyl-1-azoniabicyclo[2.2.2]octane iodide;
(3R)-3-[Benzyl-(2-fluorophenyl)carbamoyloxy]-1-methyl-1-azoniabicyclo[2.2.2]octane iodide; or
(3R)-3-[Cyclohexylmethyl-(2-fluorophenyl)carbamoyloxy]-1-methyl-1-azoniabicyclo[2.2.2]octane iodide.

7. The compound of claim 2, wherein R1 represents a group chosen from phenyl, 2-thienyl, 3-thienyl, thiophen-2-ylmethyl, thiophen-3-ylmethyl, furan-2-ylmethyl, and furan-3-ylmethyl, wherein the cyclic group present in R1 is optionally substituted with one, two, or three, identical or different, substituents chosen from fluorine, chlorine, bromine, methyl, methoxy, trifluoromethyl, ethyl, tert-butyl, hydroxy, and cyano.

8. The compound of claim 7, wherein R1 represents a group chosen from phenyl, 2-fluorophenyl, 3-flurorophenyl, 4-fluorophenyl, 3-methylphenyl, 4-methylphenyl, 2,5-difluorophenyl, 2,6-difluorophenyl, 2,4,5-trifluorophenyl, 5-methylfuran-2-ylmethyl, 4-fluoro-2-methylphenyl, 3-fluoro-4-methoxyphenyl, 3-methyl-thiophen-2-ylmethyl, 4,5-dimethyl-thiophen-2-ylmethyl, thiophen-3-ylmethyl, 5-methyl-furan-2-ylmethyl, 5-methyl-2-trifluoromethyl-furan-3-ylmethyl, and 2, 5-dimethyl-furan-3-ylmethyl.

9. The compound of claim 2, wherein R2 represents a group chosen from pent-4-enyl, pentyl, butyl, allyl, benzyl, thiophen-2-ylmethyl, thiophen-3-ylmethyl, furan-2-ylmethyl, furan-3-ylmethyl, phenethyl, cyclopentyl, cyclohexyl, and cyclohexylmethyl, wherein the cyclic group present in R2 is optionally substituted with one, two, or three, identical or different, substituents chosen from fluorine, chlorine, bromine, methyl, methoxy, trifluoromethyl, ethyl, tert-butyl, hydroxy, and cyano.

10. The compound of claim 9, wherein R2 represents a group chosen from 3-fluorobenzyl, 2,4,5-trifluorobenzyl, 3,4,5-trifluorobenzyl, 5-bromothiophen-2-ylmethyl, 3,4-dimethoxyphenylethyl, 3-methylthiophen-2-ylmethyl, thiophen-3-ylmethyl, 4-bromo-5-methylthiophen-2-ylmethyl, 4,5-dimethylfuran-2-ylmethyl, furan-3-ylmethyl, 2-fluoro-4-methoxybenzyl, 2-(4-fluorophenyl)ethyl, butyl, pent-4-enyl, and cyclopentyl.

11. The compound of claim 2, wherein
A is —CH$_2$—;
m and n are both 0;
B represents a group chosen from straight or branched, optionally substituted lower alkyl; hydroxy; straight or branched, optionally substituted lower alkoxy; cyano; nitro; —CH=CR'R"; —C(O)OR'; —OC(O)R; —SC(O)R'; —C(O)NR'R"; —NR'C(O)OR"; —NR'C(O)NR"; cycloalkyl; phenyl; naphthanelyl; 5,6,7,8-tetrahydronaphthanelyl; benzo[1,3]dioxolyl; heteroaryl; and heterocyclyl; and R' and R" are each independently chosen from a hydrogen atom and a straight or branched, optionally substituted lower alkyl group, or R' and R" together with the atom to which they are attached form a cyclic group;

and wherein the cyclic groups represented by B are optionally substituted by one, two or three, identical or different, substituents chosen from halogen; hydroxyl; straight or branched, optionally substituted lower alkyl; phenyl; —OR'; —SR'; —NR'R"; —NHCOR'; —CONR'R"; —CN, —NO$_2$ and —COOR'; wherein R' and R" are each independently chosen from a hydrogen atom, or a straight or branched, optionally substituted lower alkyl group, or R' and R" together with the atom to which they are attached form a cyclic group.

12. The compound of claim 2, wherein
A is —CH$_2$—;
B represents a hydrogen atom, or a group chosen from straight or branched, optionally substituted lower alkyl; hydroxy; straight or branched, optionally substituted lower alkoxy; cyano; nitro; —CH=CR'R"; —C(O)OR'; —OC(O)R'; —SC(O)R'; —C(O)NR'R"; —NR'C(O)OR"; —NR'C(O)NR"; cycloalkyl; phenyl; naphthanelyl; 5,6,7,8-tetrahydronaphthanelyl; benzo[1,3]dioxolyl; heteroaryl; and heterocyclyl;

wherein R' and R" are each independently chosen from a hydrogen atom and a straight or branched, optionally substituted lower alkyl group, or R' and R" together with the atom to which they are attached form a cyclic group;

and wherein the cyclic group represented by B is optionally substituted by one, two or three, identical or different, substituents chosen from halogen; hydroxy; straight or branched, optionally substituted lower alkyl; phenyl; —OR'; —SR'; —NR'R"; —NHCOR'; —CONR'R"; —CN; —NO$_2$; and —COOR'; wherein R' and R" are each independently chosen from a hydrogen atom, or a straight or branched, optionally substituted lower alkyl group, or R' and R" together with the atom to which they are attached form a cyclic group; and at least one of m or n is not 0.

13. The compound of claim 2, wherein B represents a thiophen-2-yl group or a phenyl group which is optionally substituted with one, two, or three, identical or different, substituents chosen from halogen atoms and hydroxy, methyl, —CH$_2$OH, —OMe, —NMe$_2$, —NHCOMe, —CONH$_2$, —CN, —NO$_2$, —COOMe, and —CF$_3$ groups.

14. The compound of claim 13, wherein B represents a group chosen from phenyl, 4-fluorophenyl, 3-hydroxyphenyl, and thiophen-2-yl.

15. The compound of claim 2, wherein n=0 or 1; m is an integer ranging from 1 to 6; and A represents a group chosen from —CH$_2$—, —CH=CH—, —CO—, —NMe—, —O—, and —S—.

16. The compound of claim 15, wherein m is an integer equal to 1, 2 or 3 and A represents a group chosen from —CH$_2$—, —CH=CH—, and —O—.

17. The compound of claim 2, wherein B—(CH$_2$)$_n$—A-(CH$_2$)$_m$— represents a group chosen from 3-phenoxypropyl, 2-phenoxyethyl, 3-phenylallyl, phenethyl, 3-phenylpropyl, 3-(3-hydroxyphenoxy)propyl, 3-(4-fluorophenoxy)propyl, 3-thiophen-2-ylpropyl, allyl, heptyl, 3-cyanopropyl, and methyl.

18. The compound of claim 2, wherein X⁻ represents anion chosen from chloride, bromide, trifluoroacetate, and methanesulphonate.

19. The compound of claim 1, wherein p is 2.

20. The compound of claim 1, wherein the azabicyclic ring is substituted in the 3-position.

21. The compound of claim 20, wherein the carbon at the 3-position of the azabicyclic ring has R configuration.

22. The compound of claim 20, wherein the carbon at the 3-position of the azabicyclic ring has S configuration.

23. The compound of claim 1, wherein the compound of formula (I) is a single isomer.

24. The compound of claim 1, chosen from:
- [2-(3,4-Dimethoxyphenyl)ethyl]-(5-methylfuran-2-ylmethyl)carbamic acid (3R)-1-azabicyclo[2.2.2]oct-3-yl ester;
- (5-Bromothiophen-2-ylmethyl)-(2,4,5-trifluorophenyl)carbamic acid (3R)-1-azabicyclo[2.2.2]oct-3-yl ester;
- (4-Fluoro-2-methylphenyl)-(3-methylthiophen-2-ylmethyl)carbamic acid (3R)-1-azabicyclo[2.2.2]oct-3-yl ester;
- (3-Fluoro-4-methoxyphenyl)thiophen-3-ylmethylcarbamic acid (3R)-1-azabicyclo[2.2.2]oct-3-yl ester
- Thiophen-3-ylmethyl-(2,4,5-trifluorobenzyl)carbamic acid (3R)-1-azabicyclo[2.2.2]oct-3-yl ester;
- (4-Bromo-5-methylthiophen-2-ylmethyl)-(3-methylthiophen-2-ylmethyl)carbamic acid (3R)-1-azabicyclo[2.2.2]oct-3-yl ester;
- (4, 5-Dimethylfuran-2-ylmethyl)-(5-methylfuran-2-ylmethyl)carbamic acid (3R)-1-azabicyclo[2.2.2]oct-3-yl ester;
- Furan-3-ylmethyl-(5-methyl-2-trifluoromethylfuran-3-ylmethyl)carbamic acid (3R)-1-azabicyclo[2.2.2]oct-3-yl ester;
- (2,5-Dimethylfuran-3-ylmethyl)-(2-fluoro-4-methoxybenzyl)carbamic acid (3R)-1-azabicyclo[2.2.2]oct-3-yl ester;
- [2-(4-Fluorophenyl)ethyl]-(3-methylthiophen-2-ylmethyl)carbamic acid (3R)-1-azabicyclo[2.2.2]oct-3-yl ester;
- Butyl-(2, 5-difluorophenyl)carbamic acid (3R)-1-azabicyclo[2.2.2]oct-3-yl ester;
- (2,6-Difluorophenyl)pent-4-enylcarbamic acid (3R)-1-aza-bicyclo[2.2.2]oct-3-yl ester;
- Cyclopentyl-(4,5-dimethylthiophen-2-ylmethyl)carbamic acid (3R)-1-azabicyclo[2.2.2]oct-3-yl ester; and
- (5-Ethylthiophen-2-ylmethyl)-(3-methylthiophen-2-ylmethyl)carbamic acid (3R)-1-azabicyclo[2.2.2]oct-3-yl ester.

25. The compound of claim 2, chosen from:
- (3R)-3-[(3-Fluorobenzyl)-(3-fluorophenyl)carbamoyloxy)-1-(2-phenoxyethyl)-1-azoniabicyclo[2.2.2]octane bromide;
- (3R)-3-[(3-Fluorobenzyl)-(3-fluorophenyl)carbamoyloxy]-1-(3-phenylpropyl)-1-azoniabicyclo[2.2.2]octane bromide;
- (3R)-1-(2-Phenoxyethyl)-3-[m-tolyl-(2,4,5-trifluorobenzyl)carbamoyloxy]-1-azoniabicyclo[2.2.2]octane bromide;
- (3R)-1-(3-Phenylpropyl)-3-[m-tolyl-(2,4,5-trifluorobenzyl)carbamoyloxy]-1-azoniabicyclo[2.2.2]octane bromide;
- (3R)-3-[(3-Fluorophenyl)-(3,4,5-trifluorobenzyl)carbamoyloxy]-1-(2-phenoxyethyl)-1-azoniabicyclo[2.2.2]octane bromide;
- (3R)-1-Allyl-3-[[2-(3,4-dimethoxyphenyl)ethyl]-(5-methylfuran-2-ylmethyl)carbamoyloxy]-1-azoniabicyclo[2.2.2]octane bromide;
- (3R)-3-[(5-Bromothiophen-2-ylmethyl)-(2,4,5-trifluorophenyl)carbamoyloxy]-1-(3-phenoxypropyl)-1-azoniabicyclo[2.2.2]octane trifluoroacetate;
- (3R)-3-[[2-(3,4-dimethoxyphenyl)ethyl]-(5-methylfuran-2-ylmethyl)carbamoyloxy]-1-(4-ethoxycarbonylbutyl)-1-azoniabicyclo[2.2.2]octane trifluoroacetate;
- (3R)-3-[(4-Fluoro-2-methylphenyl)-(3-methylthiophen-2-ylmethyl)carbamoyloxy]-1-(2-phenoxyethyl)-1-azoniabicyclo[2.2.2]octane trifluoroacetate;
- (3R)-3-[(3-Fluoro-4-methoxyphenyl)thiophen-3-ylmethylcarbamoyloxy]-1-(3-phenylallyl)-1-azoniabicyclo[2.2.2]octane trifluoroacetate;
- (3R)-1-Phenethyl-3-[thiophen-3-ylmethyl-(2,4,5-trifluorobenzyl)carbamoyloxyl-1-azoniabicyclo[2.2.2]octane trifluoroacetate;
- (3R)-3-[(4-Bromo-5-methylthiophen-2-ylmethyl)-(3-methylthiophen-2-ylmethyl)carbamoyloxy]-1-(3-phenylpropyl)-1-azoniabicyclo[2.2.2]octane trifluoroacetate;
- (3R)-3-[(4,5-Dimethylfuran-2-ylmethyl)-(5-methylfuran-2-ylmethyl)carbamoyloxy]-1-[3-(3-hydroxyphenoxy)propyl]-1-azoniabicyclo[2.2.2]octane trifluoroacetate;
- (3R)-1-[3-(4-Fluorophenoxy)propyl]-3-[furan-3-ylmethyl-(5-methyl-2-trifluoromethylfuran-3-ylmethyl)carbamoyloxy]-1-azoniabicyclo[2.2.2]octane trifluoroacetate;
- (3R)-3-[(2,5-Dimethylfuran-3-ylmethyl)-(2-fluoro-4-methoxybenzyl)carbamoyloxy]-1-(3-thiophen-2-ylpropyl)-1-azoniabicyclo[2.2.2]octane trifluoroacetate;
- (3R)-1-Allyl-3-[2-(4-fluorophenyl)ethyl]-(3-methylthiophen-2-ylmethyl)carbamoyloxy]-1-azoniabicyclo[2.2.2]octane trifluoroacetate;
- (3R)-3-[Butyl-(2,5-difluorophenyl)carbamoyloxy]-1-heptyl-1-azoniabicyclo[2.2.2]octane trifluoroacetate;
- (3R)-1-(3-cyanopropyl)-3-[(2,6-difluorophenyl)pent-4-enylcarbamoyloxy]-1-azoniabicyclo[2.2.2]octane trifluoroacetate;
- (3R)-3-[Cyclopentyl-(4,5-dimethylthiophen-2-ylmethyl)carbamoyloxy]-1-methyl-1-azoniabicyclo[2.2.2}octane trifluoroacetate;
- (3R)-3-[(3-Fluorophenyl)-(3,4,5-trifluorobenzyl)carbamoyloxy]-1-(3-phenylpropyl)-1-azoniabicyclo[2.2.2]octane bromide;
- (3R)-3-[(5-Ethylthiophen-2-ylmethyl)-(3-methylthiophen-2-ylmethyl)carbamoyloxy]-1-(3-phenylpropyl)-1-azoniabicyclo[2.2.2]octane bromide;
- (3R)-3-[[2-(3,4-dimethoxyphenyl)ethyl]-(5-methylfuran-2-ylmethyl)carbamoyloxy]-1-(4-ethoxycarbonylbutyl)-1-azoniabicyclo[2.2.2]octane formate;
- (3R)-3-[(4-Fluoro-2-methylphenyl)-(3-methylthiophen-2-ylmethyl)carbamoyloxy]-1-(2-phenoxyethyl)-1-azoniabicyclo[2.2.2]octane bromide;
- (3R)-3-[(3-Fluoro-4-methoxyphenyl)thiophen-3-ylmethylcarbamoyloxy]-1-(3-phenylallyl)-1-azoniabicyclo[2.2.2]octane bromide; and
- (3R)-1-Allyl-3-[2-(4-fluorophenyl)ethyl]-(3-methylthiophen-2-ylmethyl)carbamoyloxy]-1-azoniabicyclo[2.2.2]octane bromide.

26. A pharmaceutical composition comprising at least one compound of claim 1, and at least one pharmaceutically acceptable carrier or diluent.

27. A pharmaceutical composition comprising at least one compound of claim 2, and at least one pharmaceutically acceptable carrier or diluent.

* * * * *

UNITED STATES PATENT AND TRADEMARK OFFICE
CERTIFICATE OF CORRECTION

PATENT NO. : 7,435,742 B2  Page 1 of 3
APPLICATION NO. : 10/518496
DATED : October 14, 2008
INVENTOR(S) : Maria Prat Quinones et al.

It is certified that error appears in the above-identified patent and that said Letters Patent is hereby corrected as shown below:

In claim 1, column 56, line 23, "maybe" should read --may be--.

In claim 1, column 56, line 48, "bicycle[2,2,1]heptanyl;" should read --bicyclo[2,2,1]heptanyl;--.

In claim 2, column 57, line 48, "R'and" should read --R' and--.

In claim 2, column 57, line 51, "R'and R"together" should read --R' and R" together--.

In claim 2, column 57, line 60, "R'and" should read --R' and--.

In claim 6, column 59, lines 17-18, "(3 R)-3-(Benzyl-o-tolylcarbamoyloxy)-1-methyl-1-azoniabicyclo[2.2.2]octane iodide" should read --(3R)-3-(Benzyl-o-tolylcarbamoyloxy)-1-methyl-1-azoniabicyclo[2.2.2]octane iodide;--.

In claim 8, column 59, line 43, "2, 5-dimethyl-furan-3-ylmethyl." should read --2,5-dimethyl-furan-3-ylmethyl.--.

In claim 24, column 61, line 15, "(3R)-1 -azabicyclo[2.2.2]oct-3-yl" should read --(3R)-1-azabicyclo[2.2.2]oct-3-yl--.

In claim 24, column 61, lines 17-18, "(5-Bromothiophen-2-ylmethyl)-(2,4,5-trifiuorophenyl)carbamic acid (3R)-1-azabicyclo[2.2.2joct-3-yl" should read --(5-Bromothiophen-2-ylmethyl)-(2,4,5-trifluorophenyl)carbamic acid (3R)-1-azabicyclo[2.2.2]oct-3-yl--.

In claim 24, column 61, lines 19-20, "(4-Fluoro-2-methylphenyl)-(3-methythiophen-2-ylmethyl)carbamic" should read --(4-Fluoro-2-methylphenyl)-(3-methylthiophen-2-ylmethyl)carbamic--.

In claim 24, column 61, line 23, "ester" should read --ester;--.

In claim 24, column 61, lines 29-30, "(4, 5-Dimethylfuran-2-ylmethyl)-(5-methylfuran-2-ylmethyl)carbamic" should read --(4,5-Dimethylfuran-2-ylmethyl)-(5-methylfuran-2-ylmethyl)carbamic--.

In claim 24, column 61, line 41, "Butyl-(2, 5-difluorophenyl)carbamic" should read --Butyl-(2,5-difluorophenyl)carbamic--.

UNITED STATES PATENT AND TRADEMARK OFFICE
CERTIFICATE OF CORRECTION

PATENT NO.       : 7,435,742 B2
APPLICATION NO.  : 10/518496
DATED            : October 14, 2008
INVENTOR(S)      : Maria Prat Quinones et al.

It is certified that error appears in the above-identified patent and that said Letters Patent is hereby corrected as shown below:

In claim 24, column 61, line 48, "(3R)-1 -azabicyclo[2.2.2]oct-3-yl" should read --(3R)-1-azabicyclo[2.2.2]oct-3-yl--.

In claim 25, column 61, lines 63-65, "(3R)-3-[(3-Fluorophenyl)-(3,4,5-trifluorobenzyl)carbamoyloxy]-1-(2-phenoxyethyl)-1 -azoniabicyclo[2.2.2]octane" should read --(3R)-3-[(3-Fluorophenyl)-(3,4,5-trifluorobenzyl)carbamoyloxy]-1-(2-phenoxyethyl)-1-azoniabicyclo[2.2.2]octane--.

In claim 25, column 62, lines 4-6, "(3R)-3-[(5-Bromothiophen-2-ylmethyl)-(2,4,5-trifluorophenyl)carbamoyloxy]-1-(3-phenoxypropyl)-1-azoniabicyclo[2.2.2joctane" should read --(3R)-3-[(5-Bromothiophen-2-ylmethyl)-(2,4,5-trifluorophenyl)carbamoyloxy]-1-(3-phenoxypropyl)-1-azoniabicyclo[2.2.2]octane--.

In claim 25, column 62, lines 13-15, "(3R)-3-[(3-Fluoro-4-methoxyphenyl)thiophen-3-ylmethylcarbamoyloxy]-1-(3-phenylallyl)-1 -azoniabicyclo[2.2.2]octane" should read --(3R)-3-[(3-Fluoro-4-methoxyphenyl)thiophen-3-ylmethylcarbamoyloxy]-1-(3-phenylallyl)-1-azoniabicyclo[2.2.2]octane--.

In claim 25, column 62, lines 16-17, "(3R)-1-Phenethyl-3-[thiophen-3-ylmethyl-(2,4,5-trifluorobenzyl)carbamoyloxyl-1 -azoniabicyclo[2.2.2]octane" should read --(3R)-1-Phenethyl-3-[thiophen-3-ylmethyl-(2,4,5-trifluorobenzyl)carbamoyloxyl-1-azoniabicyclo[2.2.2]octane--.

In claim 25, column 62, lines 28-30, "(3R)-3-[(2,5-Dimethylfuran-3-ylmethyl)-(2-fluoro-4-methoxybenzyl)carbamoyloxy]- 1-(3-thiophen-2-ylpropyl)-1-azoniabicyclo[2.2.2]octane" should read --(3R)-3-[2,5-Dimethylfuran-3-ylmethyl)-(2-fluoro-4-methoxybenzyl)carbamoyloxy]-1-(3-thiophen-2-ylpropyl)-1-azoniabicyclo[2.2.2]octane--.

In claim 25, column 62, lines 31-33, "(3R)-1-Allyl-3-[2-(4-fluorophenyl)ethyl]-(3-methylthiophen-2-ylmethyl)carbamoyloxy]-1 -azoniabicyclo[2.2.2]octane" should read --(3R)-1-Allyl-3-[2-(4-fluorophenyl)ethyl]-(3-methylthiophen-2-ylmethyl)carbamoyloxy]-1-azoniabicyclo[2.2.2]octane--.

In claim 25, column 62, lines 38-40, "(3R)-3-[Cyclopentyl-(4,5-dimethylthiophen-2-ylmethyl)carbamoyloxy]-1-methyl-1-azoniabicyclo[2.2.2]octane" should read --(3R)-3-[Cyclopentyl-(4,5-dimethylthiopen-2-ylmethyl)carbamoyloxy]-1-methyl-1-azoniabicyclo[2.2.2]octane--.

UNITED STATES PATENT AND TRADEMARK OFFICE
CERTIFICATE OF CORRECTION

PATENT NO. : 7,435,742 B2
APPLICATION NO. : 10/518496
DATED : October 14, 2008
INVENTOR(S) : Maria Prat Quinones et al.

It is certified that error appears in the above-identified patent and that said Letters Patent is hereby corrected as shown below:

In claim 25, column 62, lines 55-57, "(3R)-1 -Allyl-3-[2-(4-fluorophenyl)ethyl]-(3-methylthiophen-2-ylmethyl)carbamoyloxy]-1-azoniabicyclo[2.2.2]octane" should read --(3R)-1-Allyl-3-[2-(4-fluorophenyl)ethyl]-(3-methylthiophen-2-ylmethyl)carbamoyloxy]-1-azoniabicyclo[2.2.2]octane--.

Signed and Sealed this

Sixth Day of January, 2009

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,435,742 B2 | Page 1 of 1 |
| APPLICATION NO. | : 10/518496 | |
| DATED | : October 14, 2008 | |
| INVENTOR(S) | : Prat Quinones et al. | |

It is certified that error appears in the above-identified patent and that said Letters Patent is hereby corrected as shown below:

On the cover page,

[*] Notice:   Subject to any disclaimer, the term of this patent is extended or adjusted under 35 U.S.C. 154(b) by 296 days Delete the phrase "by 296 days" and insert -- by 594 days --

Signed and Sealed this

Twenty-seventh Day of April, 2010

David J. Kappos
*Director of the United States Patent and Trademark Office*